US010577633B2

(12) United States Patent
Bomble et al.

(10) Patent No.: US 10,577,633 B2
(45) Date of Patent: Mar. 3, 2020

(54) ENZYME SCAFFOLDS AND METHODS OF USE

(71) Applicant: Alliance for Sustainable Energy, LLC, Golden, CO (US)

(72) Inventors: Yannick J. Bomble, Arvada, CO (US); Michael E. Himmel, Littleton, CO (US); Jeffrey Linger, Denver, CO (US); Roman Brunecky, Arvada, CO (US); John Aikens, La Grange, IL (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 133 days.

(21) Appl. No.: 15/467,340

(22) Filed: Mar. 23, 2017

(65) Prior Publication Data

US 2017/0275653 A1    Sep. 28, 2017

Related U.S. Application Data

(60) Provisional application No. 62/312,158, filed on Mar. 23, 2016, provisional application No. 62/312,220, filed on Mar. 23, 2016.

(51) Int. Cl.

| | |
|---|---|
| *C12P 7/18* | (2006.01) |
| *C12N 11/00* | (2006.01) |
| *C12N 9/04* | (2006.01) |
| *C12N 9/02* | (2006.01) |
| *C12N 9/10* | (2006.01) |
| *C12N 15/62* | (2006.01) |
| *C12N 11/18* | (2006.01) |
| *C07K 14/195* | (2006.01) |
| *C12N 11/06* | (2006.01) |
| *C12P 7/42* | (2006.01) |

(52) U.S. Cl.
CPC .............. *C12P 7/18* (2013.01); *C07K 14/195* (2013.01); *C12N 9/0006* (2013.01); *C12N 9/0008* (2013.01); *C12N 9/0036* (2013.01); *C12N 9/1022* (2013.01); *C12N 11/00* (2013.01); *C12N 11/06* (2013.01); *C12N 11/18* (2013.01); *C12N 15/62* (2013.01); *C12P 7/42* (2013.01); *C12Y 101/01006* (2013.01); *C12Y 101/01076* (2013.01); *C12Y 101/01086* (2013.01); *C12Y 102/01* (2013.01); *C12Y 102/01003* (2013.01); *C12Y 106/03* (2013.01); *C12Y 106/03001* (2013.01); *C12Y 202/01006* (2013.01)

(58) Field of Classification Search
CPC .............. C12P 7/18; C12Y 106/03001; C12Y 102/01003; C12Y 202/01006; C12Y 101/01076; C12Y 106/03; C12Y 101/01006; C12Y 102/01; C12Y 101/01086; C07K 14/195; C12N 9/0008; C12N 9/0006; C12N 9/0036; C12N 11/06; C12N 15/62; C12N 11/18; C12N 9/1022; C12N 11/00

See application file for complete search history.

(56) References Cited

U.S. PATENT DOCUMENTS 4,952,501 A    8/1990 Jasin et al.

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Branden et al. (Introduction to Protein Structure, Garland Publishing Inc., New York, p. 247, 1991.*
Kim et al., Journal of Biotechnology 192:192-196, 2014.*
UniProtKB accession No. Q06851 (CIPA_CLOTH), 2019.*
An et al., "Reversible Compartmentalization of de Novo Purine Biosynthetic Complexes in Living Cells", Science, 2008, vol. 320, No. 5872, pp. 103-106.
Bagnara-Tardif et al., "Sequence Analysis of a Gene Cluster Encoding Cellulases from *Clostridium cellulolyticum*", Gene, Sep. 1992, vol. 119, No. 1, pp. 17-28.
Bayer et al., "Adherence of Clostridium thermocellum to Cellulose", Journal of Bacteriology, Nov. 1983, vol. 156, No. 2, pp. 818-827.
Bayer et al., "Ultrastructure of the Cell Surface Cellulosome of *Clostridium thermocellum* and Its Interaction with Cellulose", Journal of Bacteriology, Sep. 1986, vol. 167, pp. 828-836.
Bayer et al., "Cellulosomes-Structure and Ultrastructure", Journal of Structural Biology, Dec. 1998, vol. 124, Nos. 1-2 pp. 221-245.
Bayer et al., "Cellulose, Cellulases and Cellulosomes", Current Opinion in Structural Biology, Oct. 1998, vol. 8, No. 5, pp. 548-557.
Bayer et al., "The Cellulosomes: Multienzyme Machines for Degradation of Plant Cell Wall Polysaccharides", Annual Review of Microbiology, 2004, vol. 58, pp. 521-554.
Bayer et al., "From Cellulosomes to Cellulosomics", The Chemical Record, Dec. 2008, vol. 8, No. 6, pp. 364-377.
Béguin et al., "The Cellulosome: An Exocellular, Multiprotein Complex Specialized in Cellulose Degradation", Critical Reviews in Biochemistry and Molecular Biology, 1996, vol. 31, No. 3, pp. 201-236.
Bhat et al., Isolation of Four Major Subunits from *Clostridium thermocellum* Cellulosome and their Synergism in the Hydrolysis of Crystalline Cellulose, International Journal of Biological Macromolecules, 1994, vol. 16, pp. 335-342.

(Continued)

*Primary Examiner* — Delia M Ramirez
(74) *Attorney, Agent, or Firm* — John C. Stolpa; Alexandra M. Hall

(57) ABSTRACT

Polypeptide scaffolds comprising enzymatic proteins are provided. The enzymatic polypeptide scaffolds comprise heterologous enzymes to form a heterologous metabolic pathway, and can be targeted to a substrate through a surface anchoring domain. The enzymatic polypeptide scaffolds leverage the high specificity and affinity protein/protein interaction between the cohesins and dockerins of microorganismal cellulosomes to form custom enzymatic arrays.

8 Claims, 20 Drawing Sheets

Specification includes a Sequence Listing.

(56) References Cited

OTHER PUBLICATIONS

Bomble et al., "Modeling the Self-Assembly of the Cellulosome Enzyme Complex", Journal of Biological Chemistry, Feb. 2011, vol. 286, No. 7, pp. 5614-5623.
Bozell et al., "Technology Development for the Production of Biobased Products from Biorefinery Carbohydrates—the US Department of Energy's "Top 10" revisited", Green Chemistry, 2010, vol. 12, No. 4, pp. 539-554.
Carvalho et al., "Evidence for a dual binding mode of dockerin modules to cohesins", Proceedings of the National Academy of Sciences of the United States of America, Feb. 2007, vol. 104, No. 9, pp. 3089-3094.
Caspi et al., "*Thermobifida fusca* Family-6 Cellulases as Potential Designer Cellulosome Components", Biocatalysis and Biotransformation, 2006, vol. 24, pp. 3-12.
Cha et al., "Effect of Multiple Copies of Cohesins on Cellulase and Hemicellulase Activities of *Clostridium cellulovorans* Mini-Cellulosomes", Journal of Microbioogy and Biotechnology, 2007, vol. 17, No. 11, pp. 1782-1788.
Ciruela et al., "Synergistic Interaction of the Cellulosome Integrating Protein (CipA) from *Clostridium thermocellum* with a Cellulosomal Endoglucanase", FEBS Letters, 1998, vol. 422, pp. 221-224.
Cornillot et al., "Physical and Genetic Map of the Clostridium Acetobutylicum ATCC 824 Chromosome", Journal of Bacteriology, Dec. 1997, vol. 179, No. 23, pp. 7426-7434.
Demain et al., "Cellulase, Clostridia, and Ethanol", Microbiology and Molecular Biology Reviews, Mar. 2005, vol. 69, No. 1, pp. 124-154.
Demishtein et al., "Characterization of a Dockerin-Based Affinity Tag: Application for Purification of a Broad Variety of Target Proteins", Journal of Molecular Recognition, Nov./Dec. 2010, vol. 23, No. 6, pp. 525-535.
DiCosimo et al., "Industrial Use of Immobilized Enzymes", The Royal Society of Chemistry—Review Article, 2013, vol. 42, pp. 6437-6474.
Ding et al., "A Scaffoldin of the *Bacteroides cellulosolvens* Cellulosome That Contains 11 Type II Cohesins", Journal of Bacteriology, Sep. 2000, vol. 182, No. 17, pp. 4915-4925.
Doi, "Cellulases of Mesophilic Microorganisms: Cellulosome and Noncellulosome Produce", Annals fo the New York Academy of Sciences, Mar. 2008, vol. 1125, pp. 267-279.
Dueber et al., "Synthetic Protein Scaffolds Provide Modular Control Over Metabolic Flux", Nature Biotechnology, 2009, vol. 27, No. 8, pp. 753-759.
Fierobe et al., "Degradation of Cellulose Substrates by Cellulosome Chimeras Substrate Targeting Versus Proximity of Enzyme Components", The Journal of Biological Chemistry, Dec. 2002, vol. 277, No. 51, pp. 49621-49630.
Fierobe et al., "Action of Designer Cellulosomes on Homogeneous Versus Complex Substrates", The Journal of Biological Chemistry, Apr. 2005, vol. 280, No. 16, pp. 16325-16334.
Fortas et al., "New insight into the structure and function of Hfq C-terminus", Bioscience Reports, Apr. 2015, vol. 35, No. 2, e00190, pp. 1-9.
Fujino et al., "Organization of a *Clostridium thermocellum* Gene Cluster Encoding the Cellulosomal Scaffolding Protein CipA and a Protein Possibly Involved in Attachment of the Cellulosome to the Cell Surface", Journal of Bacteriology, Apr. 1993, vol. 175, No. 7, pp. 1891-1899.
Gavin et al., "Functional Organization of the Yeast Proteome by Systematic Analysis of Protein Complexes", Nature, Jan. 2002, vol. 415, pp. 141-147.
Gerwig et al., "The Nature of the Carbohydrate-peptide Linkage Region in Glycoproteins from the Cellulosomes of *Clostridium thermocellum* and *Bacteroides cellulosolvens*", Journal of Biological Chemistry, Dec. 1993, vol. 268, No. 36, pp. 26956-26990.

Gilbert et al., "Cellulosomes: Microbial Nanomachines that Display Plasticity in Quaternary Structure", Molecular Microbiology, Mar. 2007, vol. 63, No. 6, pp. 1568-1576.
Haimovitz et al., "Cohesin-Dockerin Microarray: Diverse Specificities Between Two Complementary Families of Interacting Protein Modules", Proteomics, Jan. 2008, vol. 8, vol. 5, pp. 968-979.
Hamberg et al., "Elaborate Cellulosome Architecture of *Acetivibrio cellulolyticu* revealed by Selective Screening of Cohesin-Dockerin Interactions", Peer J., 2014, pp. 1-21.
Han et al., "Effect of Carbon Source on the Cellulosomal Subpopulations of *Clostridium cellulovorans*", Microbiology, May 2005, vol. 151, pp. 1491-1497.
Henikoff et al., "Amino Acid Substitution Matrices from Protein Blocks", Proceedings of the National Academy of Sciences of the United States of America, Nov. 1992, vol. 89, No. 22. pp. 10915-10919.
Himmel et al., "Microbial Enzyme Systems for Biomass Conversion: Emerging Paradigms", Biofuels, Mar. 2010, vol. 1, No. 2, pp. 323-341.
Jindou et al., "Cellulosome Gene Cluster Analysis for Gauging the Diversity of the Ruminal Cellulolytic Bacterium *Ruminococcus flavefaciens*", FEMS Microbiology Letters, Aug. 2008, vol. 285, pp. 188-194.
Kakiuchi et al., "Cloning and DNA Sequencing of the Genes Encoding *Clostridium josui* Scaffolding Protein CipA and Cellulase CelD and Identification of Their Gene Products as Major Components of the Cellulosome", Journal of Bacteriology, Aug. 1998, vol. 180, No. 16, pp. 4303-4308.
Kataeva et al., "Interaction Between *Clostridium thermocellum* Endoglucanase CelD and Polypeptides Derived from the Cellulosome-integrating Protein CipA: Stoichiometry and Cellulolytic Activity of the Complexes", Biochemical Journal, Sep. 1997, vol. 326, No. 2, pp. 617-624.
Kosugi et al., "Xylanase and Acetyl Xylan Esterase Activities of XynA, a Key Subunit of the *Clostridium cellulovorans* Cellulosome for Xylan Degradation", Applied and Environmental Microbiology, Dec. 2002, vol. 68, No. 12, pp. 6399-6402.
Lamed et al., "Cellulosomes from *Clostridium thermocellum*", Methods in Enzymology, 1988, vol. 160, pp. 472-482.
Leibovitz et al., "A New Type of Cohesin Domain that Specifically Binds the Dockerin Domain of the *Clostridium thermocellum* Cellulosome-Integrating Protein CipA", Journal of Bacteriology, Jun. 1996, vol. 178, No. 11, pp. 3077-3084.
Lynd et al., "Microbial Cellulose Utilization: Fundamentals and Biotechnology", Microbiology and Molecular Biology Reviews, Dec. 2002, vol. 66, No. 3, pp. 506-577.
Mayer et al., "Macromolecular Organization of the Cellulolytic Enzyme Complex of *Clostridium thermocellum* as Revealed by Electron Microscopy", Applied and Environmental Microbiology, Dec. 1987, vol. 53, No. 12, pp. 2785-2792.
Mechaly et al., "Cohesin-Dockerin Interaction in Cellulosome Assembly: A Single Hydroxyl Group of a Dockerin Domain Distinguishes Between Nonrecognition and High Affinity Recognition", Journal of Biological Chemistry, 2001, vol. 276, No. 13, pp. 9883-9888.
Mingardon et al., "Exploration of New Geometries in Cellulosome-Like Chimeras", Applied and Environmental Microbiology, Nov. 2007, vol. 73, No. 22, pp. 7138-7149.
Morag et al., "Unorthodox Intrasubunit Interactions in the Cellulosome of *Clostridium thermocellum*", Applied Biochemistry and Biotechnology, Jun. 1992, vol. 33, No. 3, pp. 205-217.
Morag et al., "Dissociation of the cellulosome of *Clostridium thermocellum* under nondenaturing conditions", Journal of Biotechnology, Nov. 1996, vol. 51, No. 3, pp. 235-242.
Pagès et al., "Role of Scaffolding Protein CipC of *Clostridium cellulolyticum* in Cellulose Degradation", Journal of Bacteriology, May 1997, vol. 179, No. 9, pp. 2810-2816.
Pagès et al., "Species-Specificity of the Cohesin-Dockerin Interaction Between *Clostridium thermocellum* and *Clostridium cellulolyticum*: Prediction of Specificity Determinants of the Dockerin Domain", Proteins: Structure, Function, and Genetics, Dec. 1997, vol. 29, No. 4, pp. 517-527.
Pagès et al., "Sequence Analysis of Scaffolding Protein CipC and ORFXp, a New Cohesin-Containing Protein in *Clostridium cel-*

(56) References Cited

OTHER PUBLICATIONS

*lulolyticum*: Comparison of Various Cohesin Domains and Subcellular Localization of ORFXp", Journal of Bacteriology, Mar. 1999, vol. 181, No. 6, pp. 1801-1810.

Pohlschröder et al., "Multicomplex Cellulase-Xylanase System of *Clostridium papyrosolvens* C7", Journal of Bacteriology, Jan. 1994, vol. 176, No. 1, pp. 70-76.

Raman et al., "Impact of Pretreated Switchgrass and Biomass Carbohydrates on *Clostridium thermocellum* ATCC 27405 Cellulosome Composition: A Quantitative Proteomic Analysis", PLOS One, Apr. 2009, vol. 4, No. 4, e5271, pp. 1-13.

Rincon et al., "Novel Organization and Divergent Dockerin Specificities in the Cellulosome System of *Ruminococcus flavefaciens*", Journal of Bacteriology, Feb. 2003, vol. 185, No. 3, pp. 703-713.

Rincon et al., "Unconventional Mode of Attachment of the *Ruminococcus flavefaciens* Cellulosome to the Cell Surface", Journal of Bacteriology, Nov. 2005, vol. 187, No. 22, pp. 7569-7578.

Sabathé et al., "Characterization of the Cellulolytic Complex (cellulosome) of *Clostridium acetobutylicum*", FEMS Microbiology Letters, Nov. 2002, vol. 217, No. 1, pp. 15-22.

Salamitou et al., "Involvement of separate domains of the cellulosomal protein S1 of *Clostridium thermocellu* in binding to cellulose and in anchoring of catalytic subunits to the cellulosome", FEBS Letters, Jun. 1992, vol. 304, No. 1, pp. 89-92.

Salamitou et al., "Recognition Specificity of the Duplicated Segments Present in *Clostridium thermocellum* Endoglucanase CelD and in the Cellulosome-Integrating Protein CipA", Journal of Bacteriology, May 1994, vol. 176, No. 10, pp. 2822-2827.

Schulte, "Protein Complexes Challenges and Opportunities for Drug Discovery", Logopharm GmbH, Germany, 2008, pp. 1-3.

Shoseyov et al., "Primary Sequence Analysis of *Clostridium cellulovorans* Cellulose Binding Protein A", Proceedings of the National Academy of Sciences of the United States of America, Apr. 1992, vol. 89, pp. 3483-3487.

Stahl et al., "Single-molecule dissection of the high-affinity cohesin-dockerin complex", Proceedings of the National Academy of Sciences of the United States of America, 2012, vol. 109, No. 50, pp. 20431-20436.

Stevens et al., "Bisulfite as Scavenger for Enhanced Biotechnological Production of 3-hydroxypropionaldehyde by *Lactobacillus reuteri*", Biochemical Engineering Journal, 2013, vol. 79, pp. 239-245.

Warnecke et al., "Organic Acid Toxicity, Tolerance, and Production in *Escherichia coli* Biorefining Applications", Microbial Cell Factories, 2005, vol. 4, No. 25, pp. 1-8.

Wu et al., "Two Components of an Extracellular Protein Aggregate of *Clostridium thermocellum* Together Degrade Crystalline Cellulose", Biochemistry, Mar. 1988, vol. 27, pp. 1703-1709.

Xu et al., "A Novel *Acetivibrio cellulolyticus* Anchoring Scaffoldin That Bears Divergent Cohesins", Journal of Bacteriology, Sep. 2004, vol. 186, No. 17, pp. 5782-5789.

Yaron et al., "Expression, Purification and Bubunit-binding Properties of Cohesins 2 and 3 of the *Clostridium thermocellum* Cellulosome", FEBS Letters, Feb. 1995, vol. 360, No. 2, pp. 121-124.

Zhao et al., "Binding of S-Layer Homology Modules From *Clostridium thermocellum* SdbA to Peptidoglycans", Applied Microbiology and Biotechnology, Apr. 2006, vol. 70, No. 4, pp. 464-469.

Bitinaite et al., "FokI dimerization is required for DNA cleavage", Proceedings of the National Academy of Sciences of the United States of America, Sep. 1998, vol. 95, No. 18, pp. 10570-10575.

Blair et al., "Molecular mechanisms of antibiotic resistance", Nature Reviews—Microbiology, Jan. 2015, vol. 13, No. 1, pp. 42-51.

Gaj et al., "ZFN, Talen and CRISPR/Cas-based methods for genome engineering", Trends in Biotechnology, Jul. 2013, vol. 31, No. 7, pp. 397-405.

He et al., "Thymic stromal lymphopoietin", Annals of the New York Academy of Sciences, Jan. 2010, vol. 1183, pp. 13-24.

Huang et al., "Splase: A new class IIs zinc-finger restriction endonuclease with specificity for Sp1 binding sites", Journal of Protein Chemistry, Jul. 1996, vol. 15, No. 5, pp. 481-489.

Kim et al., "Chimeric restriction endonuclease", Proceedings of the National Academy of Sciences of the United States of America, Feb. 1994, vol. 91, No. 3, pp. 883-887.

Kim et al., "Hybrid restriction enzymes: zinc finger fusions to Fok I cleavage domain", Proceedings of the National Academy of Sciences of the United States of America, Feb. 26, 1996, vol. 93, No. 3, pp. 1156-1160.

Liu et al., "Antibiotic Sensitivity Profiles Determined with an Escherichia coli Gene Knockout Collection: Generating an Antibiotic Bar Code", Antimicrobial Agents and Chemotherapy, Apr. 2010, vol. 54, No. 4, pp. 1393-1403.

Pandey et al., "Cloning of a receptor subunit required for signaling by thymic stromal lymphopoietin", Nature Immunology, Jul. 2000, vol. 1, No. 1, pp. 59-64.

Roberts et al., "Restriction endonucleases", CRC Critical Reviews in Biochemistry, Nov. 1976, vol. 4, No. 2, pp. 123-164.

Rochman et al., "Thymic stromal lymphopoietin: a new cytokine in asthma", Current Opinion in Pharmacology, Apr. 2008, vol. 8, No. 3, pp. 249-254.

Skowron et al., "Atypical DNA-binding properties of class-IIS restriction endonucleases: evidence for recognition of the cognate sequence by a FokI monomer", Gene, Mar. 1993, vol. 125, No. 1, pp. 1-10.

Soumelis et al., "Human epithelial cells trigger dendritic cell mediated allergic inflammation by producing TSLP", Nature Immunology, Jul. 2002, vol. 3, No. 7, pp. 673-680.

Soumelis et al., "Human thymic stromal lymphopoietin: a novel epithelial cell-derived cytokine and a potential key player in the induction of allergic inflammation", Springer Seminars in Immunopathology, Nov. 2003, vol. 25, Nos. 3-4, pp. 325-333.

Sugisaki et al., "New restriction endonucleases from Flavobacterium okeanokoites (FokI) and Micrococcus luteus (MluI)", Gene, Dec. 1981, vol. 16, Nos. 1-3, pp. 73-78.

Ungerer et al., "Cpf1 Is a Versatile Tool for CRISPR Genome Editing Across Diverse Species of Cyanobacteria", Scientific Reports, Dec. 2016, vol. 6, No. 39681, pp. 1-9.

Waddington et al., "A Broad Overview and Review of CRISPR-Cas Technology and Stem Cells", Current Stem Cell Reports, Mar. 2016, vol. 2, No. 1, pp. 9-20.

Wah et al., "Structure of the multimodular endonuclease FokI bound to DNA", Nature, Jul. 1997, vol. 388, pp. 97-100.

Wah et al., "Structure of FokI has implications for DNA cleavage", Proceedings of the National Academy of Sciences of the United States of America, Sep. 1998, vol. 95, No. 18, pp. 10564-10569.

Watanabe et al., "Hassall's corpuscles instruct dendritic cells to induce CD4+CD25+ regulatory T cells in human thymus", Nature, Aug. 2005, vol. 436, No. 7054, pp. 1181-1185.

Waugh et al., "Single amino acid substitutions uncouple the DNA binding and strand scission activities of Fok I endonuclease" Proceedings of the National Academy of Sciences of the United States of America, Oct. 1993, vol. 90, No. 20, pp. 9596-9600.

Yonezawa et al., "DNA binding mode of class-IIS restriction endonuclease FokI revealed by DNA footprinting analysis", Biochimica et Biophysica Acta (BBA)—Gene Structure and Expression, Oct. 1994, vol. 1219, No. 2, pp. 369-379.

Zhang et al., "Constitutive and inducible thymic stromal lymphopoietin expression in human airway smooth muscle cells: role in chronic obstructive pulmonary disease", American Journal of Physiology—Lung Cellular and Molecular Physiology, Aug. 2007, vol. 293, No. 2, pp. 375-382.

Zhong et al., "Site-directed mutagenesis reveals a unique requirement for tyrosine residues in IL-7Ra and TSLPR cytoplasmic domains in TSLP-dependent cell proliferation", BMC Immunology, 2010, vol. 11, No. 5, pp. 1-11.

\* cited by examiner

SEQUENCE LISTING

```
<160> NUMBER OF SEQ ID NOS: 39

<210> SEQ ID NO 1
<211> LENGTH: 58
<212> TYPE: PRT
<213> ORGANISM: Artificial Sequence
<220> FEATURE:
<223> OTHER INFORMATION: Synthetic linker polypeptide

<400> SEQUENCE: 1

Thr Pro Thr Pro Thr Ala Thr Pro Ala Pro Thr Val Thr Pro Thr Pro
1               5                   10                  15

Thr Pro Ala Pro Thr Pro Thr Pro Thr Pro Thr Pro Thr Ala Thr Pro
            20                  25                  30

Thr Pro Thr Pro Thr Pro Thr Pro Thr Ala Thr Pro Thr Val Thr Ala
        35                  40                  45

Thr Pro Thr Pro Thr Pro Ser Ser Thr Pro
    50                  55

<210> SEQ ID NO 2
<211> LENGTH: 8
<212> TYPE: PRT
<213> ORGANISM: Artificial Sequence
<220> FEATURE:
<223> OTHER INFORMATION: Synthetic linker polypeptide

<400> SEQUENCE: 2

Thr Asn Lys Pro Val Ile Glu Gly
1               5

<210> SEQ ID NO 3
<211> LENGTH: 37
<212> TYPE: PRT
<213> ORGANISM: Artificial Sequence
<220> FEATURE:
<223> OTHER INFORMATION: Synthetic linker polypeptide

<400> SEQUENCE: 3
```

```
Gly Gly Gly Ser Gly Gly Gly Ser Glu Gly Gly Gly Ser Glu Gly Gly
1               5                   10                  15

Gly Ser Glu Gly Gly Ser Glu Gly Gly Ser Glu Gly Gly
            20                  25                  30

Ser Gly Gly Gly Ser
            35

<210> SEQ ID NO 4
<211> LENGTH: 19
<212> TYPE: PRT
<213> ORGANISM: Artificial Sequence
<220> FEATURE:
<223> OTHER INFORMATION: Synthetic linker polypeptide

<400> SEQUENCE: 4

Thr Thr Val Pro Thr Thr Ser Pro Thr Thr Thr Pro Pro Glu Pro Thr
1               5                   10                  15

Ile Thr Pro

<210> SEQ ID NO 5
<211> LENGTH: 20
<212> TYPE: PRT
<213> ORGANISM: Artificial Sequence
<220> FEATURE:
<223> OTHER INFORMATION: Synthetic linker polypeptide

<400> SEQUENCE: 5

Thr Thr Ser Thr Thr Thr Thr Thr Val Thr Thr Thr Ser Thr Thr Thr
1               5                   10                  15

Thr Thr Val Thr
            20

<210> SEQ ID NO 6
<211> LENGTH: 37
<212> TYPE: PRT
<213> ORGANISM: Artificial Sequence
<220> FEATURE:
<223> OTHER INFORMATION: Synthetic linker polypeptide
<220> FEATURE:
<221> NAME/KEY: REPEAT
<222> LOCATION: (14)..(18)
<223> OTHER INFORMATION: Residues 14 - 18 can be repeated between 1 and
      200 times

<400> SEQUENCE: 6

Gly Gly Gly Ser Gly Gly Gly Ser Glu Gly Gly Gly Ser Glu Gly Gly
1               5                   10                  15

Gly Ser Glu Gly Gly Ser Glu Gly Gly Ser Glu Gly Gly Ser Glu Gly Gly Gly
            20                  25                  30

Ser Gly Gly Gly Ser
            35

<210> SEQ ID NO 7
<211> LENGTH: 37
<212> TYPE: PRT
<213> ORGANISM: Artificial Sequence
<220> FEATURE:
<223> OTHER INFORMATION: Synthetic linker polypeptide

<400> SEQUENCE: 7

Gly Gly Gly Ser Gly Gly Gly Ser Glu Gly Gly Gly Ser Glu Gly Gly
1               5                   10                  15

Gly Ser Glu Gly Gly Gly Ser Glu Gly Gly Gly Ser Glu Gly Gly Gly
```

20                  25                  30

Ser Gly Gly Gly Ser
         35

<210> SEQ ID NO 8
<211> LENGTH: 607
<212> TYPE: PRT
<213> ORGANISM: Klebsiella pneumoniae

<400> SEQUENCE: 8

Met Pro Leu Ile Ala Gly Ile Asp Ile Gly Asn Ala Thr Thr Glu Val
1               5                   10                  15

Ala Leu Ala Ser Asp Tyr Pro Gln Ala Arg Ala Phe Val Ala Ser Gly
            20                  25                  30

Ile Val Ala Thr Thr Gly Met Lys Gly Thr Arg Asp Asn Ile Ala Gly
        35                  40                  45

Thr Leu Ala Ala Leu Glu Gln Ala Leu Ala Lys Thr Pro Trp Ser Met
    50                  55                  60

Ser Asp Val Ser Arg Ile Tyr Leu Asn Glu Ala Ala Pro Val Ile Gly
65                  70                  75                  80

Asp Val Ala Met Glu Thr Ile Thr Glu Thr Ile Thr Glu Ser Thr
                85                  90                  95

Met Ile Gly His Asn Pro Gln Thr Pro Gly Gly Val Gly Val Gly Val
            100                 105                 110

Gly Thr Thr Ile Ala Leu Gly Arg Leu Ala Thr Leu Pro Ala Ala Gln
        115                 120                 125

Tyr Ala Glu Gly Trp Ile Val Leu Ile Asp Asp Ala Val Asp Phe Leu
    130                 135                 140

Asp Ala Val Trp Trp Leu Asn Glu Ala Leu Asp Arg Gly Ile Asn Val
145                 150                 155                 160

Val Ala Ala Ile Leu Lys Lys Asp Asp Gly Val Leu Val Asn Asn Arg
                165                 170                 175

Leu Arg Lys Thr Leu Pro Val Val Asp Glu Val Thr Leu Leu Glu Gln
            180                 185                 190

Val Pro Glu Gly Val Met Ala Ala Val Glu Val Ala Ala Pro Gly Gln
        195                 200                 205

Val Val Arg Ile Leu Ser Asn Pro Tyr Gly Ile Ala Thr Phe Phe Gly
    210                 215                 220

Leu Ser Pro Glu Glu Thr Gln Ala Ile Val Pro Ile Ala Arg Ala Leu
225                 230                 235                 240

Ile Gly Asn Arg Ser Ala Val Val Leu Lys Thr Pro Gln Gly Asp Val
                245                 250                 255

Gln Ser Arg Val Ile Pro Ala Gly Asn Leu Tyr Ile Ser Gly Glu Lys
            260                 265                 270

Arg Arg Gly Glu Ala Asp Val Ala Glu Gly Ala Glu Ala Ile Met Gln
        275                 280                 285

Ala Met Ser Ala Cys Ala Pro Val Arg Asp Ile Arg Gly Glu Pro Gly
    290                 295                 300

Thr His Ala Gly Gly Met Leu Glu Arg Val Arg Lys Val Met Ala Ser
305                 310                 315                 320

Leu Thr Gly His Glu Met Ser Ala Ile Tyr Ile Gln Asp Leu Leu Ala
                325                 330                 335

Val Asp Thr Phe Ile Pro Arg Lys Val Gln Gly Gly Met Ala Gly Glu
            340                 345                 350

```
Cys Ala Met Glu Asn Ala Val Gly Met Ala Ala Met Val Lys Ala Asp
            355                 360                 365
Arg Leu Gln Met Gln Val Ile Ala Arg Glu Leu Ser Ala Arg Leu Gln
        370                 375                 380
Thr Glu Val Val Gly Gly Val Glu Ala Asn Met Ala Ile Ala Gly
385                 390                 395                 400
Ala Leu Thr Thr Pro Gly Cys Ala Ala Pro Leu Ala Ile Leu Asp Leu
                405                 410                 415
Gly Ala Gly Ser Thr Asp Ala Ala Ile Val Asn Ala Glu Gly Gln Ile
            420                 425                 430
Thr Ala Val His Leu Ala Gly Ala Gly Asn Met Val Ser Leu Leu Ile
        435                 440                 445
Lys Thr Glu Leu Gly Leu Glu Asp Leu Ser Leu Ala Glu Ala Ile Lys
    450                 455                 460
Lys Tyr Pro Leu Ala Lys Val Glu Ser Leu Phe Ser Ile Arg His Glu
465                 470                 475                 480
Asn Gly Ala Val Glu Phe Phe Arg Glu Ala Leu Ser Pro Ala Val Phe
                485                 490                 495
Ala Lys Val Val Tyr Ile Lys Glu Gly Glu Leu Val Pro Ile Asp Asn
            500                 505                 510
Ala Ser Pro Leu Glu Lys Ile Arg Leu Val Arg Arg Gln Ala Lys Glu
        515                 520                 525
Lys Val Phe Val Thr Asn Cys Leu Arg Ala Leu Arg Gln Val Ser Pro
    530                 535                 540
Gly Gly Ser Ile Arg Asp Ile Ala Phe Val Val Leu Val Gly Gly Ser
545                 550                 555                 560
Ser Leu Asp Phe Glu Ile Pro Gln Leu Ile Thr Glu Ala Leu Ser His
                565                 570                 575
Tyr Gly Val Val Ala Gly Gln Gly Asn Ile Arg Gly Thr Glu Gly Pro
            580                 585                 590
Arg Asn Ala Val Ala Thr Gly Leu Leu Leu Ala Gly Gln Ala Asn
        595                 600                 605

<210> SEQ ID NO 9
<211> LENGTH: 506
<212> TYPE: PRT
<213> ORGANISM: Klebsiella pneumoniae

<400> SEQUENCE: 9

Met Arg Tyr Ala His Pro Gly Gln Pro Gly Ala Val Val Ser Phe Lys
1               5                   10                  15
Ser Ala Tyr Gly Asn Phe Ile Asp Gly Arg Phe Val Glu Pro Leu Ser
            20                  25                  30
Gly Glu Phe Phe Met Asn Thr Ser Pro Val Asp Gly Cys Asn Ile Ala
        35                  40                  45
Gln Phe Pro Arg Ser Asp Ala Arg Asp Ile Asp Phe Ala Leu Asp Ala
    50                  55                  60
Ala His Arg Ala Ala Pro Ala Trp Gly Lys Thr Ser Val Gln Gln Arg
65                  70                  75                  80
Ser Arg Leu Leu Leu Gln Val Ala Asp Arg Ile Glu Gln His Leu Glu
                85                  90                  95
Tyr Leu Ala Val Ala Glu Ser Trp Asp Asn Gly Lys Pro Ile Arg Glu
            100                 105                 110
Thr Leu Asn Ala Asp Leu Pro Leu Ala Val Asp His Phe Arg Tyr Phe
        115                 120                 125
```

```
Ala Gly Cys Leu Arg Ala Gln Glu Gly Ser Thr Ala Glu Ile Asp Glu
            130                 135                 140

Thr Thr Val Ala Tyr His Phe His Glu Pro Leu Gly Val Val Gly Gln
145                 150                 155                 160

Ile Ile Pro Trp Asn Phe Pro Leu Leu Met Ala Ala Trp Lys Leu Ala
                165                 170                 175

Pro Ala Leu Ala Ala Gly Asn Cys Val Val Leu Lys Pro Ala Glu Gln
            180                 185                 190

Thr Pro Leu Ser Ile Thr Leu Leu Glu Leu Ile Gly Asp Leu Phe
        195                 200                 205

Pro Ala Gly Val Leu Asn Val Val Gln Gly Phe Gly Lys Glu Ala Gly
210                 215                 220

Glu Ala Leu Ala Thr Ser Lys Arg Ile Ala Lys Leu Ala Phe Thr Gly
225                 230                 235                 240

Ser Thr Pro Val Gly Arg His Ile Leu Ala Cys Ala Ala Glu Asn Ile
                245                 250                 255

Ile Pro Cys Thr Val Glu Leu Gly Gly Lys Ser Pro Asn Ile Tyr Phe
            260                 265                 270

Ala Asp Val Met Asp Gly Glu Glu Phe Ile Glu Lys Ala Val Glu
        275                 280                 285

Gly Leu Val Leu Gly Phe Phe Asn Gln Gly Glu Val Cys Thr Cys Pro
290                 295                 300

Ser Arg Ala Leu Ile His Glu Ser Ile Tyr Glu Pro Phe Met Ala Arg
305                 310                 315                 320

Val Met Glu Lys Val Ala Gln Ile Arg Arg Gly Asp Pro Leu Asp Thr
                325                 330                 335

Asp Thr Met Ile Gly Ala Gln Ala Ser Arg Gln Gln Phe Asp Lys Ile
            340                 345                 350

Leu Ser Tyr Ile Gln Ile Ala Arg Glu Glu Gly Gly Gln Ile Leu Thr
        355                 360                 365

Gly Gly Glu Arg Ala Ala Ile Ala Pro Ala Leu Asp Asn Gly Phe Tyr
370                 375                 380

Ile Gln Pro Thr Leu Ile Lys Gly Arg Asn Asp Met Arg Ser Phe Gln
385                 390                 395                 400

Glu Glu Ile Phe Gly Pro Val Ile Gly Val Thr Thr Phe Lys Asp Glu
                405                 410                 415

Ala Glu Ala Leu Ala Ile Ala Asn Glu Thr Gln Phe Gly Leu Gly Ala
            420                 425                 430

Gly Val Trp Thr Arg Asp Thr Asn Leu Ala Tyr Arg Met Gly Arg Gly
        435                 440                 445

Ile Lys Ala Gly Arg Val Trp Thr Asn Cys Tyr His Val Tyr Pro Ala
450                 455                 460

His Ala Ala Phe Gly Gly Tyr Lys Gln Ser Gly Val Gly Arg Glu Thr
465                 470                 475                 480

His Lys Met Ala Leu Asp Ala Tyr Gln Gln Thr Lys Asn Leu Leu Val
                485                 490                 495

Ser Tyr Gly Thr Ala Pro Leu Gly Leu Phe
        500                 505
```

<210> SEQ ID NO 10
<211> LENGTH: 446
<212> TYPE: PRT
<213> ORGANISM: Lactococcus lactis

<400> SEQUENCE: 10

```
Met Lys Ile Val Val Ile Gly Thr Asn His Ala Gly Ile Ala Thr Ala
1               5                   10                  15

Asn Thr Leu Leu Glu Gln Tyr Pro Gly His Glu Ile Val Met Ile Asp
            20                  25                  30

Arg Asn Ser Asn Met Ser Tyr Leu Gly Cys Gly Thr Ala Ile Trp Val
        35                  40                  45

Gly Arg Gln Ile Glu Lys Pro Asp Glu Leu Phe Tyr Ala Lys Ala Glu
    50                  55                  60

Asp Phe Glu Ala Lys Gly Val Lys Ile Leu Thr Glu Thr Glu Val Ser
65                  70                  75                  80

Glu Ile Asp Phe Ala Asn Lys Val Tyr Ala Lys Thr Lys Ser Asp
                85                  90                  95

Asp Glu Ile Ile Glu Ala Tyr Asp Lys Leu Val Leu Ala Thr Gly Ser
                100                 105                 110

Arg Pro Ile Ile Pro Asn Leu Pro Gly Lys Asp Leu Lys Gly Ile His
            115                 120                 125

Phe Leu Lys Leu Phe Gln Glu Gly Gln Ala Ile Asp Ala Glu Phe Ala
130                 135                 140

Lys Glu Lys Val Lys Arg Ile Ala Val Ile Gly Ala Gly Tyr Ile Gly
145                 150                 155                 160

Thr Glu Ile Ala Glu Ala Ala Lys Arg Arg Gly Lys Glu Val Leu Leu
                165                 170                 175

Phe Asp Ala Glu Asn Thr Ser Leu Ala Ser Tyr Tyr Asp Glu Glu Phe
            180                 185                 190

Ala Lys Gly Met Asp Glu Asn Leu Ala Gln His Gly Ile Glu Leu His
        195                 200                 205

Phe Gly Glu Leu Ala Lys Glu Phe Lys Ala Asn Glu Glu Gly Tyr Val
    210                 215                 220

Ser Gln Ile Val Thr Asn Lys Ala Thr Tyr Asp Val Asp Leu Val Ile
225                 230                 235                 240

Asn Cys Ile Gly Phe Thr Ala Asn Ser Ala Leu Ala Ser Asp Lys Leu
                245                 250                 255

Ala Thr Phe Lys Asn Gly Ala Ile Lys Val Asp Lys His Gln Gln Ser
            260                 265                 270

Ser Asp Pro Asp Val Tyr Ala Val Gly Asp Val Ala Thr Ile Tyr Ser
        275                 280                 285

Asn Ala Leu Gln Asp Phe Thr Tyr Ile Ala Leu Ala Ser Asn Ala Val
    290                 295                 300

Arg Ser Gly Ile Val Ala Gly His Asn Ile Gly Gly Lys Glu Leu Glu
305                 310                 315                 320

Ser Val Gly Val Gln Gly Ser Asn Gly Ile Ser Ile Phe Gly Tyr Asn
                325                 330                 335

Met Thr Ser Thr Gly Leu Ser Val Lys Ala Ala Lys Lys Leu Gly Leu
            340                 345                 350

Glu Val Ser Phe Ser Asp Phe Glu Asp Lys Gln Lys Ala Trp Phe Leu
        355                 360                 365

His Glu Asn Asn Asp Ser Val Lys Ile Arg Ile Val Tyr Glu Thr Lys
    370                 375                 380

Ser Arg Arg Ile Ile Gly Ala Gln Leu Ala Ser Lys Ser Glu Ile Ile
385                 390                 395                 400

Ala Gly Asn Ile Asn Met Phe Ser Leu Ala Ile Gln Glu Lys Lys Thr
                405                 410                 415
```

```
Ile Asp Glu Leu Ala Leu Leu Asp Leu Phe Phe Leu Pro His Phe Asn
                420                 425                 430

Ser Pro Tyr Asn Tyr Met Thr Val Ala Ala Leu Asn Ala Lys
            435                 440                 445

<210> SEQ ID NO 11
<211> LENGTH: 141
<212> TYPE: PRT
<213> ORGANISM: Acetivibrio cellulolyticus

<400> SEQUENCE: 11

Pro Ser Gly Ser Asp Leu Gln Val Asp Ile Gly Ser Thr Ser Gly Lys
1               5                   10                  15

Ala Gly Ser Val Val Ser Val Pro Ile Thr Phe Thr Asn Val Pro Lys
            20                  25                  30

Ser Gly Ile Tyr Ala Leu Ser Phe Arg Thr Asn Phe Asp Pro Gln Lys
        35                  40                  45

Val Thr Val Ala Ser Ile Asp Ala Gly Ser Leu Ile Glu Asn Ala Ser
    50                  55                  60

Asp Phe Thr Thr Tyr Tyr Asn Asn Glu Asn Gly Phe Ala Ser Met Thr
65                  70                  75                  80

Phe Glu Ala Pro Val Asp Arg Ala Arg Ile Ile Asp Ser Asp Gly Val
                85                  90                  95

Phe Ala Thr Ile Asn Phe Lys Val Ser Asp Ser Ala Lys Val Gly Glu
            100                 105                 110

Leu Tyr Asn Ile Thr Thr Asn Ser Ala Tyr Thr Ser Phe Tyr Tyr Ser
        115                 120                 125

Gly Thr Asp Glu Ile Lys Asn Val Val Tyr Asn Asp Gly
    130                 135                 140

<210> SEQ ID NO 12
<211> LENGTH: 77
<212> TYPE: PRT
<213> ORGANISM: Acetivibrio cellulolyticus

<400> SEQUENCE: 12

Met Ala Lys Phe Ile Tyr Gly Asp Val Asp Gly Asn Gly Ser Val Arg
1               5                   10                  15

Ile Asn Asp Ala Val Leu Ile Arg Asp Tyr Val Leu Gly Lys Ile Asn
            20                  25                  30

Glu Phe Pro Tyr Glu Tyr Gly Met Leu Ala Ala Asp Val Asp Gly Asn
        35                  40                  45

Gly Ser Ile Lys Ile Asn Asp Ala Val Leu Val Arg Asp Tyr Val Leu
    50                  55                  60

Gly Lys Ile Phe Leu Phe Pro Val Glu Glu Lys Glu Glu
65                  70                  75

<210> SEQ ID NO 13
<211> LENGTH: 151
<212> TYPE: PRT
<213> ORGANISM: Clostridium cellulolyticum

<400> SEQUENCE: 13

Thr Val Leu Pro Lys Asp Ile Pro Gly Asp Ser Leu Lys Val Thr Val
1               5                   10                  15

Gly Thr Ala Asn Gly Lys Pro Gly Asp Thr Val Thr Val Pro Val Thr
            20                  25                  30
```

Phe Ala Asp Val Ala Lys Met Lys Asn Val Gly Thr Cys Asn Phe Tyr
            35                  40                  45

Leu Gly Tyr Asp Ala Ser Leu Leu Glu Val Val Ser Val Asp Ala Gly
 50                  55                  60

Pro Ile Val Lys Asn Ala Ala Val Asn Phe Ser Ser Ala Ser Asn
 65                  70                  75                  80

Gly Thr Ile Ser Phe Leu Phe Leu Asp Asn Thr Ile Thr Asp Glu Leu
                 85                  90                  95

Ile Thr Ala Asp Gly Val Phe Ala Asn Ile Lys Phe Lys Leu Lys Ser
                100                 105                 110

Val Thr Ala Lys Thr Thr Thr Pro Val Thr Phe Lys Asp Gly Gly Ala
            115                 120                 125

Phe Gly Asp Gly Thr Met Ser Lys Ile Ala Ser Val Thr Lys Thr Asn
130                 135                 140

Gly Ser Val Thr Ile Asp Pro
145                 150

<210> SEQ ID NO 14
<211> LENGTH: 64
<212> TYPE: PRT
<213> ORGANISM: Clostridium cellulolyticum

<400> SEQUENCE: 14

Val Ile Val Tyr Gly Asp Tyr Asn Asn Asp Gly Asn Val Asp Ser Thr
 1               5                  10                  15

Asp Phe Ala Gly Leu Lys Lys Tyr Ile Met Ala Ala Asp His Ala Tyr
             20                  25                  30

Val Lys Asn Leu Asp Val Asn Leu Asp Asn Glu Val Asn Ala Phe Asp
             35                  40                  45

Leu Ala Ile Leu Lys Lys Tyr Leu Leu Gly Met Val Ser Lys Leu Glu
     50                  55                  60

<210> SEQ ID NO 15
<211> LENGTH: 127
<212> TYPE: PRT
<213> ORGANISM: Bacteroides cellulosolvens

<400> SEQUENCE: 15

Gln Ile Gly Asp Val Lys Ala Asn Gln Gly Asp Thr Val Ile Val Pro
 1               5                  10                  15

Ile Thr Phe Asn Glu Val Pro Val Met Gly Val Asn Asn Cys Asn Phe
             20                  25                  30

Thr Leu Ala Tyr Asp Lys Asn Ile Met Glu Phe Ile Ser Ala Asp Ala
             35                  40                  45

Gly Asp Ile Val Thr Leu Pro Met Ala Asn Tyr Ser Tyr Asn Met Pro
     50                  55                  60

Ser Asp Gly Leu Val Lys Phe Leu Tyr Asn Asp Gln Ala Gln Gly Ala
 65                  70                  75                  80

Met Ser Ile Lys Glu Asp Gly Thr Phe Ala Asn Val Lys Phe Lys Ile
                 85                  90                  95

Lys Gln Ser Ala Ala Phe Gly Lys Tyr Ser Val Gly Ile Lys Ala Ile
                100                 105                 110

Gly Ser Ile Ser Ala Leu Ser Asn Ser Lys Leu Ile Pro Ile Glu
            115                 120                 125

<210> SEQ ID NO 16
<211> LENGTH: 82

```
<212> TYPE: PRT
<213> ORGANISM: Bacteroides cellulosolvens

<400> SEQUENCE: 16

Pro Lys Gly Thr Ala Thr Val Leu Tyr Gly Asp Val Asn Asp Gly
1               5                   10                  15

Asn Val Asp Ser Asp Asp Tyr Ala Tyr Met Arg Gln Trp Leu Ile Gly
                20                  25                  30

Met Ile Ala Asp Phe Pro Gly Gly Asp Ile Gly Leu Ala Asn Ala Asp
            35                  40                  45

Val Asp Gly Asp Gly Asn Val Asp Ser Asp Asp Tyr Ala Tyr Met Arg
        50                  55                  60

Gln Trp Leu Ile Gly Met Ile Ser Glu Phe Pro Ala Glu Gln Lys Ala
65                  70                  75                  80

Leu Glu

<210> SEQ ID NO 17
<211> LENGTH: 119
<212> TYPE: PRT
<213> ORGANISM: Clostridium thermocellum

<400> SEQUENCE: 17

Val Glu Ile Pro Val Tyr Phe Arg Gly Val Pro Ser Lys Gly Ile Ala
1               5                   10                  15

Asn Cys Asp Phe Val Phe Arg Tyr Asp Pro Asn Val Leu Glu Ile Ile
                20                  25                  30

Gly Ile Asp Pro Gly Asp Ile Ile Val Asp Pro Asn Pro Thr Lys Ser
            35                  40                  45

Phe Asp Thr Ala Ile Tyr Pro Asp Arg Lys Ile Ile Val Phe Leu Phe
        50                  55                  60

Ala Glu Asp Ser Gly Thr Gly Ala Tyr Ala Ile Thr Lys Asp Gly Val
65                  70                  75                  80

Phe Ala Lys Ile Arg Ala Thr Val Lys Ser Ser Ala Pro Gly Tyr Ile
                85                  90                  95

Thr Phe Asp Glu Val Gly Gly Phe Ala Asp Asn Asp Leu Val Glu Gln
            100                 105                 110

Lys Val Ser Phe Ile Asp Gly
        115

<210> SEQ ID NO 18
<211> LENGTH: 67
<212> TYPE: PRT
<213> ORGANISM: Clostridium thermocellum

<400> SEQUENCE: 18

Met Gly Ser Gly Asp Val Asn Asp Gly Lys Val Asn Ser Thr Asp
1               5                   10                  15

Ala Val Ala Leu Lys Arg Tyr Val Leu Arg Ser Gly Ile Ser Ile Asn
                20                  25                  30

Thr Asp Asn Ala Asp Leu Asn Glu Asp Gly Arg Val Asn Ser Thr Asp
            35                  40                  45

Leu Gly Ile Leu Lys Arg Tyr Ile Leu Lys Glu Ile Asp Thr Leu Pro
        50                  55                  60

Tyr Lys Asn
65

<210> SEQ ID NO 19
```

<211> LENGTH: 140
<212> TYPE: PRT
<213> ORGANISM: Ruminococcus flavefaciens

<400> SEQUENCE: 19

```
Thr Gly Lys Ile Lys Trp Val Leu Asp Lys Val Thr Ala Ala Pro Gly
1               5                   10                  15
Glu Thr Val Thr Val Lys Ala Thr Val Asp Ala Ser Gly Glu Gly Thr
            20                  25                  30
Val Ala Val Ala Gly Ala Gln Phe Asp Val Asn Ala Asp Ser Pro Ile
        35                  40                  45
Val Tyr Asp Ser Ala Lys Glu Gly Gly Ala Tyr Ile Thr Ser Leu Thr
50                  55                  60
Val Asn Asp Ala Lys His Lys Phe Ala Phe Gly Arg Thr Thr Gly Thr
65                  70                  75                  80
Gly Ile Val Ala Ala Asp Lys Ala Thr Val Ala Ala Phe Thr Tyr Lys
                85                  90                  95
Val Pro Ser Asp Cys Thr Glu Gly Thr Tyr Asp Val Lys Trp Ser Gly
            100                 105                 110
Gly Phe Val Ser Asp Ala Asp Gly Lys Asp Ile Thr Ser Arg Val Thr
        115                 120                 125
Phe Val Asp Gly Ser Ile Thr Val Lys Asn Asp Val
    130                 135                 140
```

<210> SEQ ID NO 20
<211> LENGTH: 83
<212> TYPE: PRT
<213> ORGANISM: Ruminococcus flavefaciens

<400> SEQUENCE: 20

```
Lys Leu Val Pro Thr Trp Gly Asp Thr Asn Cys Asp Gly Val Val Asn
1               5                   10                  15
Val Ala Asp Val Val Leu Asn Arg Phe Leu Asn Asp Pro Thr Tyr
            20                  25                  30
Ser Asn Ile Thr Asp Gln Gly Lys Val Asn Ala Asp Val Val Asp Pro
        35                  40                  45
Gln Asp Lys Ser Gly Ala Ala Val Asp Pro Ala Gly Val Lys Leu Thr
50                  55                  60
Val Ala Asp Ser Glu Ala Ile Leu Lys Ala Ile Val Glu Leu Ile Thr
65                  70                  75                  80
Leu Pro Gln
```

<210> SEQ ID NO 21
<211> LENGTH: 559
<212> TYPE: PRT
<213> ORGANISM: Enterobacter cloacae

<400> SEQUENCE: 21

```
Met Asn Ser Glu Lys Gln Ser Arg Gln Trp Ala His Gly Ala Asp Met
1               5                   10                  15
Val Val Gly Gln Leu Glu Ala Gln Gly Val Lys Gln Val Phe Gly Ile
            20                  25                  30
Pro Gly Ala Lys Ile Asp Lys Val Phe Asp Ser Leu Leu Asp Ser Ser
        35                  40                  45
Ile Glu Ile Ile Pro Val Arg His Glu Ala Asn Ala Ala Phe Met Ala
50                  55                  60
Ala Ala Val Gly Arg Leu Thr Gly Lys Ala Gly Val Ala Leu Val Thr
```

-continued

```
               65                  70                  75                  80
          Ser Gly Pro Gly Cys Ser Asn Leu Ile Thr Gly Ile Ala Thr Ala Asn
                              85                  90                  95
          Ser Glu Gly Asp Pro Val Val Ala Leu Gly Ala Val Lys Arg Ala
                          100                 105                 110
          Asp Lys Ala Lys Leu Val His Gln Ser Met Asp Thr Val Ala Met Phe
                      115                 120                 125
          Ser Pro Val Thr Lys Tyr Ala Val Glu Val Ser Ser Pro Asp Ala Ile
                  130                 135                 140
          Ala Glu Val Val Ser Asn Ala Phe Arg Ala Glu His Gly Arg Pro
          145                 150                 155                 160
          Gly Gly Ala Phe Val Ser Leu Pro Gln Asp Ile Val Asp Gln Pro Ala
                              165                 170                 175
          Thr Gly Ala Ile Leu Pro Ala Ser Gly Pro Ala Leu Met Gly Pro Ala
                          180                 185                 190
          Pro Glu Ser Ala Ile Asn Asp Val Ala Lys Leu Ile Asp Asn Ala Lys
                      195                 200                 205
          Asn Pro Val Ile Leu Leu Gly Leu Met Ala Ser Gln Pro Ala Asn Ser
                  210                 215                 220
          Ala Ala Leu Arg Lys Leu Leu Glu Lys Ser Arg Ile Pro Val Thr Ser
          225                 230                 235                 240
          Thr Tyr Gln Ala Ala Gly Ala Val Asn Gln Glu His Phe Thr Arg Phe
                              245                 250                 255
          Ala Gly Arg Val Gly Leu Phe Asn Asn Gln Ala Gly Asp Arg Leu Leu
                          260                 265                 270
          His Leu Ala Asp Leu Ile Ile Cys Ile Gly Tyr Ser Pro Val Glu Tyr
                      275                 280                 285
          Glu Pro Ser Met Trp Asn Ser Gly Asp Ala Thr Leu Val His Ile Asp
                  290                 295                 300
          Val Leu Pro Ala Tyr Glu Glu Arg Asn Tyr Val Pro Asp Ile Glu Leu
          305                 310                 315                 320
          Val Gly Asp Ile Ala Ala Thr Leu Asn Leu Leu Ala Ser Arg Ile Asp
                              325                 330                 335
          His Lys Leu Glu Leu Ser Gln Arg Ala Ser Glu Ile Leu Val Asp Arg
                          340                 345                 350
          Gln His Gln Arg Asp Leu Leu Asp Arg Arg Gly Ala Ser Leu Asn Gln
                      355                 360                 365
          Phe Ala Leu His Pro Leu Arg Ile Val Arg Ala Met Gln Asp Ile Val
                  370                 375                 380
          Asn Asn Asp Val Thr Leu Thr Val Asp Met Gly Ser Phe His Ile Trp
          385                 390                 395                 400
          Ile Ala Arg Tyr Leu Tyr Ser Phe Arg Ala Arg Gln Val Met Ile Ser
                              405                 410                 415
          Asn Gly Gln Gln Thr Met Gly Val Ala Leu Pro Trp Ala Ile Gly Ala
                          420                 425                 430
          Trp Leu Val Asn Pro Gly Arg Lys Val Val Ser Val Ser Gly Asp Gly
                      435                 440                 445
          Gly Phe Leu Gln Ser Ser Met Glu Leu Glu Thr Ala Val Arg Leu Asn
                  450                 455                 460
          Ala Asn Val Leu His Ile Ile Trp Val Asp Asn Gly Tyr Asn Met Val
          465                 470                 475                 480
          Ala Ile Gln Glu Glu Lys Lys Tyr Gln Arg Leu Ser Gly Val Ala Phe
                              485                 490                 495
```

```
Gly Pro Val Asp Phe Lys Ala Tyr Ala Asp Ala Phe Gly Ala Arg Gly
            500                 505                 510

Phe Ala Val Glu Ser Ala Asp Ala Leu Glu Ser Thr Leu Arg Ala Ala
        515                 520                 525

Met Asp Val Asn Gly Pro Ala Val Val Ala Ile Pro Val Asp Tyr Ser
    530                 535                 540

Asp Asn Pro Leu Leu Met Gly Gln Leu His Leu Ser Gln Ile Leu
545                 550                 555

<210> SEQ ID NO 22
<211> LENGTH: 259
<212> TYPE: PRT
<213> ORGANISM: Enterobacter cloacae

<400> SEQUENCE: 22

Met Met His Ser Ser Ala Cys Asp Cys Glu Ala Ser Leu Cys Glu Thr
1               5                   10                  15

Leu Arg Gly Phe Ser Ala Gln His Pro Asp Ser Val Ile Tyr Gln Thr
            20                  25                  30

Ser Leu Met Ser Ala Leu Leu Ser Gly Val Tyr Glu Gly Glu Thr Thr
        35                  40                  45

Ile Ala Asp Leu Leu Ala His Gly Asp Phe Gly Leu Gly Thr Phe Asn
    50                  55                  60

Glu Leu Asp Gly Glu Met Ile Ala Phe Ser Ser Gln Val Tyr Gln Leu
65                  70                  75                  80

Arg Ala Asp Gly Ser Ala Arg Ala Ala Lys Pro Glu Gln Lys Thr Pro
                85                  90                  95

Phe Ala Val Met Thr Trp Phe Gln Pro Gln Tyr Arg Lys Thr Phe Asp
            100                 105                 110

Ala Pro Val Ser Arg Gln Gln Ile His Asp Val Ile Asp Gln Gln Ile
        115                 120                 125

Pro Ser Asp Asn Leu Phe Cys Ala Leu Arg Ile Asp Gly Asn Phe Arg
    130                 135                 140

His Ala His Thr Arg Thr Val Pro Arg Gln Lys Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Gln Gly
        195                 200                 205

Gly Gly His Leu Leu Asp Tyr Gln Leu Glu Ser Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Ser Asn Leu Asp Ala Ala Ile Arg Ser
                245                 250                 255

Val Glu Asn

<210> SEQ ID NO 23
<211> LENGTH: 256
<212> TYPE: PRT
<213> ORGANISM: Enterobacter cloacae

<400> SEQUENCE: 23
```

```
Met Gln Lys Val Ala Leu Val Thr Gly Ser Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Glu Thr Ala Arg Ala Val Ala Asp Glu Ile Ile Arg
        35                  40                  45

Asn Gly Gly Asn Ala Val Ala Val Lys Val Asp Val Ser Asp Arg Asp
    50                  55                  60

Gln Val Phe Ala Ala Val Glu Lys Ala Arg Thr Ala Leu Gly Gly Phe
65                  70                  75                  80

Asn Val Ile Val Asn Asn Ala Gly Ile Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Met Gln Ala Ala Ile Asp Ala Phe Arg Lys Glu
        115                 120                 125

Gly His Gly Gly Lys Ile Ile Asn Ala Cys Ser Gln Ala Gly His Thr
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Ala Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Glu Thr Phe Ala Lys Arg Ile Thr Leu Gly Arg Leu Ser Glu Pro
    210                 215                 220

Glu Asp Val Ala Ala Cys Val Ser Tyr Leu Ala Gly Pro Asp Ser Asp
225                 230                 235                 240

Tyr Met Thr Gly Gln Ser Leu Leu Ile Asp Gly Gly Met Val Phe Asn
                245                 250                 255

<210> SEQ ID NO 24
<211> LENGTH: 393
<212> TYPE: PRT
<213> ORGANISM: Escherichia coli

<400> SEQUENCE: 24

Met Lys Asp Val Val Ile Val Gly Ala Leu Arg Thr Pro Ile Gly Cys
1               5                   10                  15

Phe Arg Gly Ala Leu Ala Gly His Ser Ala Val Glu Leu Gly Ser Leu
            20                  25                  30

Val Val Lys Ala Leu Ile Glu Arg Thr Gly Val Pro Ala Tyr Ala Val
        35                  40                  45

Asp Glu Val Ile Leu Gly Gln Val Leu Thr Ala Gly Ala Gly Gln Asn
    50                  55                  60

Pro Ala Arg Gln Ser Ala Ile Lys Gly Gly Leu Pro Asn Ser Val Ser
65                  70                  75                  80

Ala Ile Thr Ile Asn Asp Val Cys Gly Ser Gly Leu Lys Ala Leu His
                85                  90                  95

Leu Ala Thr Gln Ala Ile Gln Cys Gly Glu Ala Asp Ile Val Ile Ala
            100                 105                 110

Gly Gly Gln Glu Asn Met Ser Arg Ala Pro His Val Leu Thr Asp Ser
        115                 120                 125
```

Arg Thr Gly Ala Gln Leu Gly Asn Ser Gln Leu Val Asp Ser Leu Val
130                 135                 140

His Asp Gly Leu Trp Asp Ala Phe Asn Asp Tyr His Ile Gly Val Thr
145                 150                 155                 160

Ala Glu Asn Leu Ala Arg Glu Tyr Gly Ile Ser Arg Gln Leu Gln Asp
                165                 170                 175

Ala Tyr Ala Leu Ser Ser Gln Gln Lys Ala Arg Ala Ile Asp Ala
                180                 185                 190

Gly Arg Phe Lys Asp Glu Ile Val Pro Val Met Thr Gln Ser Asn Gly
            195                 200                 205

Gln Thr Leu Val Val Asp Thr Asp Glu Gln Pro Arg Thr Asp Ala Ser
210                 215                 220

Ala Glu Gly Leu Ala Arg Leu Asn Pro Ser Phe Asp Ser Leu Gly Ser
225                 230                 235                 240

Val Thr Ala Gly Asn Ala Ser Ser Ile Asn Asp Gly Ala Ala Ala Val
                245                 250                 255

Met Met Met Ser Glu Ala Lys Ala Arg Ala Leu Asn Leu Pro Val Leu
            260                 265                 270

Ala Arg Ile Arg Ala Phe Ala Ser Val Gly Val Asp Pro Ala Leu Met
        275                 280                 285

Gly Ile Ala Pro Val Tyr Ala Thr Arg Arg Cys Leu Glu Arg Val Gly
        290                 295                 300

Trp Gln Leu Ala Glu Val Asp Leu Ile Glu Ala Asn Glu Ala Phe Ala
305                 310                 315                 320

Ala Gln Ala Leu Ser Val Gly Lys Met Leu Glu Trp Asp Glu Arg Arg
                325                 330                 335

Val Asn Val Asn Gly Gly Ala Ile Ala Leu Gly His Pro Ile Gly Ala
            340                 345                 350

Ser Gly Cys Arg Ile Leu Val Ser Leu Val His Glu Met Val Lys Arg
        355                 360                 365

Asn Ala Arg Lys Gly Leu Ala Thr Leu Cys Ile Gly Gly Gly Gln Gly
    370                 375                 380

Val Ala Leu Thr Ile Glu Arg Asp Glu
385                 390

<210> SEQ ID NO 25
<211> LENGTH: 729
<212> TYPE: PRT
<213> ORGANISM: Escherichia coli

<400> SEQUENCE: 25

Met Leu Tyr Lys Gly Asp Thr Leu Tyr Leu Asp Trp Leu Glu Asp Gly
1               5                   10                  15

Ile Ala Glu Leu Val Phe Asp Ala Pro Gly Ser Val Asn Lys Leu Asp
                20                  25                  30

Thr Ala Thr Val Ala Ser Leu Gly Glu Ala Ile Gly Val Leu Glu Gln
            35                  40                  45

Gln Ser Asp Leu Lys Gly Leu Leu Arg Ser Asn Lys Ala Ala Phe
        50                  55                  60

Ile Val Gly Ala Asp Ile Thr Glu Phe Leu Ser Leu Phe Leu Val Pro
65                  70                  75                  80

Glu Glu Gln Leu Ser Gln Trp Leu His Phe Ala Asn Ser Val Phe Asn
                85                  90                  95

Arg Leu Glu Asp Leu Pro Val Pro Thr Ile Ala Ala Val Asn Gly Tyr

```
            100                 105                 110
Ala Leu Gly Gly Gly Cys Glu Cys Val Leu Ala Thr Asp Tyr Arg Leu
            115                 120                 125
Ala Thr Pro Asp Leu Arg Ile Gly Leu Pro Glu Thr Lys Leu Gly Ile
            130                 135             140
Met Pro Gly Phe Gly Gly Ser Val Arg Met Pro Arg Met Leu Gly Ala
145                 150                 155                 160
Asp Ser Ala Leu Glu Ile Ile Ala Ala Gly Lys Asp Val Gly Ala Asp
                165                 170                 175
Gln Ala Leu Lys Ile Gly Leu Val Asp Gly Val Val Lys Ala Glu Lys
            180                 185                 190
Leu Val Glu Gly Ala Lys Ala Val Leu Arg Gln Ala Ile Asn Gly Asp
            195                 200                 205
Leu Asp Trp Lys Ala Lys Arg Gln Pro Lys Leu Glu Pro Leu Lys Leu
            210                 215                 220
Ser Lys Ile Glu Ala Thr Met Ser Phe Thr Ile Ala Lys Gly Met Val
225                 230                 235                 240
Ala Gln Thr Ala Gly Lys His Tyr Pro Ala Pro Ile Thr Ala Val Lys
                245                 250                 255
Thr Ile Glu Ala Ala Arg Phe Gly Arg Glu Ala Leu Asn Leu
            260                 265                 270
Glu Asn Lys Ser Phe Val Pro Leu Ala His Thr Asn Glu Ala Arg Ala
            275                 280                 285
Leu Val Gly Ile Phe Leu Asn Asp Gln Tyr Val Lys Gly Lys Ala Lys
            290                 295                 300
Lys Leu Thr Lys Asp Val Glu Thr Pro Lys Gln Ala Ala Val Leu Gly
305                 310                 315                 320
Ala Gly Ile Met Gly Gly Ile Ala Tyr Gln Ser Ala Trp Lys Gly
                325                 330                 335
Val Pro Val Val Met Lys Asp Ile Asn Asp Lys Ser Leu Thr Leu Gly
                340                 345                 350
Met Thr Glu Ala Ala Lys Leu Leu Asn Lys Gln Leu Glu Arg Gly Lys
            355                 360                 365
Ile Asp Gly Leu Lys Leu Ala Gly Val Ile Ser Thr Ile His Pro Thr
            370                 375             380
Leu Asp Tyr Ala Gly Phe Asp Arg Val Asp Ile Val Glu Ala Val
385                 390                 395                 400
Val Glu Asn Pro Lys Val Lys Lys Ala Val Leu Ala Glu Thr Glu Gln
                405                 410                 415
Lys Val Arg Gln Asp Thr Val Leu Ala Ser Asn Thr Ser Thr Ile Pro
                420                 425                 430
Ile Ser Glu Leu Ala Asn Ala Leu Glu Arg Pro Glu Asn Phe Cys Gly
            435                 440                 445
Met His Phe Phe Asn Pro Val His Arg Met Pro Leu Val Glu Ile Ile
450                 455                 460
Arg Gly Glu Lys Ser Ser Asp Glu Thr Ile Ala Lys Val Val Ala Trp
465                 470                 475                 480
Ala Ser Lys Met Gly Lys Thr Pro Ile Val Val Asn Asp Cys Pro Gly
                485                 490                 495
Phe Phe Val Asn Arg Val Leu Phe Pro Tyr Phe Ala Gly Phe Ser Gln
                500                 505                 510
Leu Leu Arg Asp Gly Ala Asp Phe Arg Lys Ile Asp Lys Val Met Glu
            515                 520                 525
```

-continued

Lys Gln Phe Gly Trp Pro Met Gly Pro Ala Tyr Leu Leu Asp Val Val
530                 535                 540

Gly Ile Asp Thr Ala His His Ala Gln Ala Val Met Ala Ala Gly Phe
545                 550                 555                 560

Pro Gln Arg Met Gln Lys Asp Tyr Arg Asp Ala Ile Asp Ala Leu Phe
            565                 570                 575

Asp Ala Asn Arg Phe Gly Gln Lys Asn Gly Leu Gly Phe Trp Arg Tyr
            580                 585                 590

Lys Glu Asp Ser Lys Gly Lys Pro Lys Lys Glu Glu Asp Ala Ala Val
            595                 600                 605

Glu Asp Leu Leu Ala Glu Val Ser Gln Pro Lys Arg Asp Phe Ser Glu
610                 615                 620

Glu Glu Ile Ile Ala Arg Met Met Ile Pro Met Val Asn Glu Val Val
625                 630                 635                 640

Arg Cys Leu Glu Glu Gly Ile Ile Ala Thr Pro Ala Glu Ala Asp Met
            645                 650                 655

Ala Leu Val Tyr Gly Leu Gly Phe Pro Pro Phe His Gly Gly Ala Phe
            660                 665                 670

Arg Trp Leu Asp Thr Leu Gly Ser Ala Lys Tyr Leu Asp Met Ala Gln
            675                 680                 685

Gln Tyr Gln His Leu Gly Pro Leu Tyr Glu Val Pro Glu Gly Leu Arg
690                 695                 700

Asn Lys Ala Arg His Asn Glu Pro Tyr Tyr Pro Val Glu Pro Ala
705                 710                 715                 720

Arg Pro Val Gly Asp Leu Lys Thr Ala
            725

<210> SEQ ID NO 26
<211> LENGTH: 383
<212> TYPE: PRT
<213> ORGANISM: Escherichia coli

<400> SEQUENCE: 26

Met Asp Phe Ser Leu Thr Glu Glu Gln Glu Leu Leu Ala Ser Ile
1               5                   10                  15

Arg Glu Leu Ile Thr Thr Asn Phe Pro Glu Glu Tyr Phe Arg Thr Cys
            20                  25                  30

Asp Gln Asn Gly Thr Tyr Pro Arg Glu Phe Met Arg Ala Leu Ala Asp
        35                  40                  45

Asn Gly Ile Ser Met Leu Gly Val Pro Glu Glu Phe Gly Gly Ile Pro
    50                  55                  60

Ala Asp Tyr Val Thr Gln Met Leu Ala Leu Met Glu Val Ser Lys Cys
65                  70                  75                  80

Gly Ala Pro Ala Phe Leu Ile Thr Asn Gly Gln Cys Ile His Ser Met
                85                  90                  95

Arg Arg Phe Gly Ser Ala Glu Gln Leu Arg Lys Thr Ala Glu Ser Thr
            100                 105                 110

Leu Glu Thr Gly Asp Pro Ala Tyr Ala Leu Ala Leu Thr Glu Pro Gly
        115                 120                 125

Ala Gly Ser Asp Asn Asn Ser Ala Thr Thr Tyr Thr Arg Lys Asn
    130                 135                 140

Gly Lys Val Tyr Ile Asn Gly Gln Lys Thr Phe Ile Thr Gly Ala Lys
145                 150                 155                 160

Glu Tyr Pro Tyr Met Leu Val Leu Ala Arg Asp Pro Gln Pro Lys Asp

```
                    165                 170                 175
Pro Lys Lys Ala Phe Thr Leu Trp Trp Val Asp Ser Ser Lys Pro Gly
            180                 185                 190

Ile Lys Ile Asn Pro Leu His Lys Ile Gly Trp His Met Leu Ser Thr
            195                 200                 205

Cys Glu Val Tyr Leu Asp Asn Val Glu Val Glu Ser Asp Met Val
    210                 215                 220

Gly Glu Glu Gly Met Gly Phe Leu Asn Val Met Tyr Asn Phe Glu Met
225                 230                 235                 240

Glu Arg Leu Ile Asn Ala Ala Arg Ser Thr Gly Phe Ala Glu Cys Ala
                245                 250                 255

Phe Glu Asp Ala Ala Arg Tyr Ala Asn Gln Arg Ile Ala Phe Gly Lys
            260                 265                 270

Pro Ile Gly His Asn Gln Met Ile Gln Glu Lys Leu Ala Leu Met Ala
            275                 280                 285

Ile Lys Ile Asp Asn Met Arg Asn Met Val Leu Lys Val Ala Trp Gln
            290                 295                 300

Ala Asp Gln His Gln Ser Leu Arg Thr Ser Ala Ala Leu Ala Lys Leu
305                 310                 315                 320

Tyr Cys Ala Arg Thr Ala Met Glu Val Ile Asp Asp Ala Ile Gln Ile
                325                 330                 335

Met Gly Gly Leu Gly Tyr Thr Asp Glu Ala Arg Val Ser Arg Phe Trp
            340                 345                 350

Arg Asp Val Arg Cys Glu Arg Ile Gly Gly Gly Thr Asp Glu Ile Met
            355                 360                 365

Ile Tyr Val Ala Gly Arg Gln Ile Leu Lys Asp Tyr Gln Asn Lys
            370                 375                 380

<210> SEQ ID NO 27
<211> LENGTH: 286
<212> TYPE: PRT
<213> ORGANISM: Escherichia coli

<400> SEQUENCE: 27

Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gly Gln Val Val Gly Gln Ala Leu Tyr Ala Ala Lys
        35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
                85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160
```

```
Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285

<210> SEQ ID NO 28
<211> LENGTH: 422
<212> TYPE: PRT
<213> ORGANISM: Jeotgalicoccus spp.

<400> SEQUENCE: 28

Met Ala Thr Leu Lys Arg Asp Lys Gly Leu Asp Asn Thr Leu Lys Val
1               5                   10                  15

Leu Lys Gln Gly Tyr Leu Tyr Thr Thr Asn Gln Arg Asn Arg Leu Asn
            20                  25                  30

Thr Ser Val Phe Gln Thr Lys Ala Leu Gly Gly Lys Pro Phe Val Val
        35                  40                  45

Val Thr Gly Lys Glu Gly Ala Glu Met Phe Tyr Asn Asn Asp Val Val
    50                  55                  60

Gln Arg Glu Gly Met Leu Pro Lys Arg Ile Val Asn Thr Leu Phe Gly
65                  70                  75                  80

Lys Gly Ala Ile His Thr Val Asp Gly Lys Lys His Val Asp Arg Lys
                85                  90                  95

Ala Leu Phe Met Ser Leu Met Thr Glu Gly Asn Leu Asn Tyr Val Arg
            100                 105                 110

Glu Leu Thr Arg Thr Leu Trp His Ala Asn Thr Gln Arg Met Glu Ser
        115                 120                 125

Met Asp Glu Val Asn Ile Tyr Arg Glu Ser Ile Val Leu Leu Thr Lys
130                 135                 140

Val Gly Thr Arg Trp Ala Gly Val Gln Ala Pro Pro Glu Asp Ile Glu
145                 150                 155                 160

Arg Ile Ala Thr Asp Met Asp Ile Met Ile Asp Ser Phe Arg Ala Leu
                165                 170                 175

Gly Gly Ala Phe Lys Gly Tyr Lys Ala Ser Lys Glu Ala Arg Arg Arg
            180                 185                 190

Val Glu Asp Trp Leu Glu Glu Gln Ile Ile Glu Thr Arg Lys Gly Asn
        195                 200                 205

Ile His Pro Pro Glu Gly Thr Ala Leu Tyr Glu Phe Ala His Trp Glu
    210                 215                 220

Asp Tyr Leu Gly Asn Pro Met Asp Ser Arg Thr Cys Ala Ile Asp Leu
225                 230                 235                 240

Met Asn Thr Phe Arg Pro Leu Ile Ala Ile Asn Arg Phe Val Ser Phe
                245                 250                 255
```

```
Gly Leu His Ala Met Asn Glu Asn Pro Ile Thr Arg Glu Lys Ile Lys
            260                 265                 270

Ser Glu Pro Asp Tyr Ala Tyr Lys Phe Ala Gln Glu Val Arg Arg Tyr
        275                 280                 285

Tyr Pro Phe Val Pro Phe Leu Pro Gly Lys Ala Lys Val Asp Ile Asp
    290                 295                 300

Phe Gln Gly Val Thr Ile Pro Ala Gly Val Gly Leu Ala Leu Asp Val
305                 310                 315                 320

Tyr Gly Thr Thr His Asp Glu Ser Leu Trp Asp Pro Asn Glu Phe
                325                 330                 335

Arg Pro Glu Arg Phe Glu Thr Trp Asp Gly Ser Pro Phe Asp Leu Ile
                340                 345                 350

Pro Gln Gly Gly Gly Asp Tyr Trp Thr Asn His Arg Cys Ala Gly Glu
            355                 360                 365

Trp Ile Thr Val Ile Ile Met Glu Gly Thr Met Lys Tyr Phe Ala Glu
370                 375                 380

Lys Ile Thr Tyr Asp Val Pro Glu Gln Asp Leu Glu Val Asp Leu Asn
385                 390                 395                 400

Ser Ile Pro Gly Tyr Val Lys Ser Gly Phe Val Ile Lys Asn Val Arg
                405                 410                 415

Glu Val Val Asp Arg Thr
            420

<210> SEQ ID NO 29
<211> LENGTH: 5
<212> TYPE: PRT
<213> ORGANISM: Artificial Sequence
<220> FEATURE:
<223> OTHER INFORMATION: Synthetic linker polypeptide

<400> SEQUENCE: 29

Glu Gly Gly Gly Ser
1               5

<210> SEQ ID NO 30
<211> LENGTH: 555
<212> TYPE: PRT
<213> ORGANISM: Vitis vinifera

<400> SEQUENCE: 30

Met Ser Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
                20                  25                  30

Phe Ile Thr Tyr Thr Pro Glu Asp Lys Val Thr Arg Ala Cys Lys Glu
            35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
    115                 120                 125
```

```
Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met His Gly Val Tyr Phe
    275                 280                 285

Glu Pro Gln Tyr Leu Arg Gly Arg Ile Leu Thr Lys Val Ile Ala
290                 295                 300

Met Thr Ser Ile Leu Asp Asp Ile His Asp Ala Tyr Gly Thr Pro Glu
305                 310                 315                 320

Glu Leu Lys Leu Phe Ile Glu Ala Ile Glu Arg Trp Asp Ile Asn Ser
                325                 330                 335

Ile Asn Gln Leu Pro Glu Tyr Met Lys Leu Cys Tyr Val Ala Leu Leu
            340                 345                 350

Asp Val Tyr Lys Glu Ile Glu Glu Met Glu Lys Glu Gly Asn Gln
    355                 360                 365

Tyr Arg Val His Tyr Ala Lys Glu Val Met Lys Asn Gln Val Arg Ala
370                 375                 380

Tyr Phe Ala Glu Ala Lys Trp Leu His Glu Glu His Val Pro Ala Phe
385                 390                 395                 400

Glu Glu Tyr Met Arg Val Ala Leu Ala Ser Ser Gly Tyr Cys Leu Leu
                405                 410                 415

Ala Thr Thr Ser Phe Val Gly Met Gly Glu Ile Ala Thr Lys Glu Ala
            420                 425                 430

Phe Asp Trp Val Thr Ser Asp Lys Ile Met Ser Ser Asn Phe Ile
    435                 440                 445

Thr Arg Leu Met Asp Asp Ile Lys Ser His Lys Phe Glu Gln Lys Arg
450                 455                 460

Gly His Val Thr Ser Ala Val Glu Cys Tyr Met Lys Gln Tyr Gly Val
465                 470                 475                 480

Ser Glu Glu Gln Val Tyr Ser Glu Phe Gln Lys Gln Ile Glu Asn Ala
                485                 490                 495

Trp Leu Asp Ile Asn Gln Glu Cys Leu Lys Pro Thr Ala Val Ser Met
            500                 505                 510

Pro Leu Leu Ala Arg Leu Leu Asn Phe Thr Arg Thr Met Asp Val Ile
    515                 520                 525

Tyr Lys Glu Gln Asp Ser Tyr Thr His Val Gly Lys Val Met Arg Asp
530                 535                 540

Asn Ile Ala Ser Val Phe Ile Asn Ala Val Ile
```

<210> SEQ ID NO 31
<211> LENGTH: 415
<212> TYPE: PRT
<213> ORGANISM: Pseudomonas putida

<400> SEQUENCE: 31

Met Thr Thr Glu Thr Ile Gln Ser Asn Ala Asn Leu Ala Pro Leu Pro
1               5                   10                  15

Pro His Val Pro Glu His Leu Val Phe Asp Phe Asp Met Tyr Asn Pro
            20                  25                  30

Ser Asn Leu Ser Ala Gly Val Gln Glu Ala Trp Ala Val Leu Gln Glu
        35                  40                  45

Ser Asn Val Pro Asp Leu Val Trp Thr Arg Cys Asn Gly Gly His Trp
    50                  55                  60

Ile Ala Thr Arg Gly Gln Leu Ile Arg Glu Ala Tyr Glu Asp Tyr Arg
65                  70                  75                  80

His Phe Ser Ser Glu Cys Pro Trp Ile Pro Arg Glu Ala Gly Glu Ala
                85                  90                  95

Phe Asp Phe Ile Pro Thr Ser Met Asp Pro Pro Glu Gln Arg Gln Phe
            100                 105                 110

Arg Ala Leu Ala Asn Gln Val Val Gly Met Pro Val Val Asp Lys Leu
        115                 120                 125

Glu Asn Arg Ile Gln Glu Leu Ala Cys Ser Leu Ile Glu Ser Leu Arg
130                 135                 140

Pro Gln Gly Gln Cys Asn Phe Thr Glu Asp Tyr Ala Glu Pro Phe Pro
145                 150                 155                 160

Ile Arg Ile Phe Met Leu Leu Ala Gly Leu Pro Glu Glu Asp Ile Pro
                165                 170                 175

His Leu Lys Tyr Leu Thr Asp Gln Met Thr Arg Pro Asp Gly Ser Met
            180                 185                 190

Thr Phe Ala Glu Ala Lys Glu Ala Leu Tyr Asp Tyr Leu Ile Pro Ile
        195                 200                 205

Ile Glu Gln Arg Arg Gln Lys Pro Gly Thr Asp Ala Ile Ser Ile Val
    210                 215                 220

Ala Asn Gly Gln Val Asn Gly Arg Pro Ile Thr Ser Asp Glu Ala Lys
225                 230                 235                 240

Arg Met Cys Gly Ala Leu Leu Val Gly Gly Leu Asp Thr Val Val Asn
                245                 250                 255

Phe Leu Ser Phe Ser Met Glu Phe Leu Ala Lys Ser Pro Glu His Arg
            260                 265                 270

Gln Glu Leu Ile Glu Arg Pro Glu Arg Ile Pro Ala Ala Cys Glu Glu
        275                 280                 285

Leu Leu Arg Arg Phe Ser Leu Val Ala Asp Gly Arg Ile Leu Thr Ser
    290                 295                 300

Asp Tyr Glu Phe His Gly Val Gln Leu Lys Lys Gly Asp Gln Ile Leu
305                 310                 315                 320

Leu Pro Gln Met Leu Ser Gly Leu Asp Glu Arg Glu Asn Ala Ala Pro
                325                 330                 335

Met His Val Asp Phe Ser Arg Gln Lys Val Ser His Thr Thr Phe Gly
            340                 345                 350

His Gly Ser His Leu Cys Leu Gly Gln His Leu Ala Arg Arg Glu Ile
        355                 360                 365

```
Ile Val Thr Leu Lys Glu Trp Leu Thr Arg Ile Pro Asp Phe Ser Ile
370                 375                 380

Ala Pro Gly Ala Gln Ile Gln His Lys Ser Gly Ile Val Ser Gly Val
385                 390                 395                 400

Gln Ala Leu Pro Leu Val Trp Asp Pro Ala Thr Thr Lys Ala Val
            405                 410                 415

<210> SEQ ID NO 32
<211> LENGTH: 1048
<212> TYPE: PRT
<213> ORGANISM: Bacillus megaterium

<400> SEQUENCE: 32

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335
```

```
Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
            450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750
```

```
Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
    915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 33
<211> LENGTH: 261
<212> TYPE: PRT
<213> ORGANISM: Bacillus subtilis

<400> SEQUENCE: 33

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80
```

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 34
<211> LENGTH: 315
<212> TYPE: PRT
<213> ORGANISM: Artificial Sequence
<220> FEATURE:
<223> OTHER INFORMATION: Synthetic polypeptide

<400> SEQUENCE: 34

Met Gly Ser Gly Asp Val Asn Asp Asp Gly Lys Val Asn Ser Thr Asp
1               5                   10                  15

Ala Val Ala Leu Lys Arg Tyr Val Leu Arg Ser Gly Ile Ser Ile Asn
            20                  25                  30

Thr Asp Asn Ala Asp Leu Asn Glu Asp Gly Arg Val Asn Ser Thr Asp
        35                  40                  45

Leu Gly Ile Leu Lys Arg Tyr Ile Leu Lys Glu Ile Asp Thr Leu Pro
    50                  55                  60

Tyr Lys Asn Glu Phe Met Ser Lys Gly Glu Glu Leu Phe Thr Gly Val
65                  70                  75                  80

Val Pro Ile Leu Val Glu Leu Asp Gly Asp Val Asn Gly His Lys Phe
                85                  90                  95

Ser Val Ser Gly Glu Gly Glu Gly Asp Ala Thr Tyr Gly Lys Leu Thr
            100                 105                 110

Leu Lys Phe Ile Cys Thr Thr Gly Lys Leu Pro Val Pro Trp Pro Thr
        115                 120                 125

Leu Val Thr Thr Leu Thr Tyr Gly Val Gln Cys Phe Ser Arg Tyr Pro
    130                 135                 140

Asp His Met Lys Arg His Asp Phe Phe Lys Ser Ala Met Pro Glu Gly
145                 150                 155                 160

Tyr Val Gln Glu Arg Thr Ile Ser Phe Lys Asp Asp Gly Asn Tyr Lys
                165                 170                 175

```
Thr Arg Ala Glu Val Lys Phe Glu Gly Asp Thr Leu Val Asn Arg Ile
            180                 185                 190

Glu Leu Lys Gly Ile Asp Phe Lys Glu Asp Gly Asn Ile Leu Gly His
        195                 200                 205

Lys Leu Glu Tyr Asn Tyr Asn Ser His Asn Val Tyr Ile Thr Ala Asp
210                 215                 220

Lys Gln Lys Asn Gly Ile Lys Ala Asn Phe Lys Ile Arg His Asn Ile
225                 230                 235                 240

Glu Asp Gly Ser Val Gln Leu Ala Asp His Tyr Gln Gln Asn Thr Pro
                245                 250                 255

Ile Gly Asp Gly Pro Val Leu Leu Pro Asp Asn His Tyr Leu Ser Thr
            260                 265                 270

Gln Ser Ala Leu Ser Lys Asp Pro Asn Glu Lys Arg Asp His Met Val
        275                 280                 285

Leu Leu Glu Phe Val Thr Ala Ala Gly Ile Thr His Gly Met Asp Glu
    290                 295                 300

Leu Tyr Lys Leu Glu His His His His His His
305                 310                 315
```

```
<210> SEQ ID NO 35
<211> LENGTH: 283
<212> TYPE: PRT
<213> ORGANISM: Artificial Sequence
<220> FEATURE:
<223> OTHER INFORMATION: Synthetic polypeptide

<400> SEQUENCE: 35

Met Leu Ala Ala Asp Val Asp Gly Asn Gly Ser Ile Lys Ile Asn Asp
1               5                   10                  15

Ala Val Leu Val Arg Asp Tyr Val Leu Gly Lys Ile Phe Leu Phe Pro
            20                  25                  30

Val Glu Glu Lys Glu Glu Val Pro Val Ser Lys Gly Glu Glu Asp Asn
        35                  40                  45

Met Ala Ile Ile Lys Glu Phe Met Arg Phe Lys Val His Met Glu Gly
    50                  55                  60

Ser Val Asn Gly His Glu Phe Glu Ile Glu Gly Glu Gly Glu Gly Arg
65                  70                  75                  80

Pro Tyr Glu Gly Thr Gln Thr Ala Lys Leu Lys Val Thr Lys Gly Gly
                85                  90                  95

Pro Leu Pro Phe Ala Trp Asp Ile Leu Ser Pro Gln Phe Met Tyr Gly
            100                 105                 110

Ser Lys Ala Tyr Val Lys His Pro Ala Asp Ile Pro Asp Tyr Leu Lys
        115                 120                 125

Leu Ser Phe Pro Glu Gly Phe Lys Trp Glu Arg Val Met Asn Phe Glu
    130                 135                 140

Asp Gly Gly Val Val Thr Val Thr Gln Asp Ser Ser Leu Gln Asp Gly
145                 150                 155                 160

Glu Phe Ile Tyr Lys Val Lys Leu Arg Gly Thr Asn Phe Pro Ser Asp
                165                 170                 175

Gly Pro Val Met Gln Lys Lys Thr Met Gly Trp Glu Ala Ser Ser Glu
            180                 185                 190

Arg Met Tyr Pro Glu Asp Gly Ala Leu Lys Gly Glu Ile Lys Gln Arg
        195                 200                 205

Leu Lys Leu Lys Asp Gly Gly His Tyr Asp Ala Glu Val Lys Thr Thr
    210                 215                 220
```

Tyr Lys Ala Lys Lys Pro Val Gln Leu Pro Gly Ala Tyr Asn Val Asn
225                 230                 235                 240

Ile Lys Leu Asp Ile Thr Ser His Asn Glu Asp Tyr Thr Ile Val Glu
                245                 250                 255

Gln Tyr Glu Arg Ala Glu Gly Arg His Ser Thr Gly Ser Met Asp Glu
            260                 265                 270

Leu Tyr Lys Leu Glu His His His His His His
        275                 280

<210> SEQ ID NO 36
<211> LENGTH: 252
<212> TYPE: PRT
<213> ORGANISM: Artificial Sequence
<220> FEATURE:
<223> OTHER INFORMATION: Synthetic polypeptide

<400> SEQUENCE: 36

Met Lys Gln His Asp Phe Phe Lys Ser Ala Met Pro Glu Gly Tyr Val
1               5                   10                  15

Gln Glu Arg Thr Ile Phe Phe Lys Asp Asp Gly Asn Tyr Lys Thr Arg
            20                  25                  30

Ala Glu Val Lys Phe Glu Gly Asp Thr Leu Val Asn Arg Ile Glu Leu
        35                  40                  45

Lys Gly Ile Asp Phe Lys Glu Asp Gly Asn Ile Leu Gly His Lys Leu
    50                  55                  60

Glu Tyr Asn Tyr Asn Ser His Asn Val Tyr Ile Thr Ala Asp Lys Gln
65                  70                  75                  80

Lys Asn Gly Ile Lys Ala Asn Phe Lys Ile Arg His Asn Ile Glu Asp
                85                  90                  95

Gly Gly Val Gln Leu Ala Asp His Tyr Gln Gln Asn Thr Pro Ile Gly
            100                 105                 110

Asp Gly Pro Val Leu Leu Pro Asp Asn His Tyr Leu Ser Tyr Gln Ser
        115                 120                 125

Ala Leu Ser Lys Asp Pro Asn Glu Lys Arg Asp His Met Val Leu Leu
    130                 135                 140

Glu Phe Val Thr Ala Ala Gly Ile Thr Leu Gly Met Asp Glu Leu Tyr
145                 150                 155                 160

Lys Leu Val Pro Pro Lys Gly Thr Ala Thr Val Leu Tyr Gly Asp Val
                165                 170                 175

Asp Asn Asp Gly Asn Val Asp Ser Asp Tyr Ala Tyr Met Arg Gln
            180                 185                 190

Trp Leu Ile Gly Met Ile Ala Asp Phe Pro Gly Gly Asp Ile Gly Leu
        195                 200                 205

Ala Asn Ala Asp Val Asp Gly Asp Gly Asn Val Asp Ser Asp Asp Tyr
    210                 215                 220

Ala Tyr Met Arg Gln Trp Leu Ile Gly Met Ile Ser Glu Phe Pro Ala
225                 230                 235                 240

Glu Gln Lys Ala Leu Glu His His His His His
                245                 250

<210> SEQ ID NO 37
<211> LENGTH: 676
<212> TYPE: PRT
<213> ORGANISM: Artificial Sequence
<220> FEATURE:
<223> OTHER INFORMATION: Synthetic polypeptide

<400> SEQUENCE: 37

```
Met Ala Asn Thr Pro Val Ser Gly Asn Leu Lys Val Glu Phe Tyr Asn
1               5                   10                  15

Ser Asn Pro Ser Asp Thr Thr Asn Ser Ile Asn Pro Gln Phe Lys Val
            20                  25                  30

Thr Asn Thr Gly Ser Ser Ala Ile Asp Leu Ser Lys Leu Thr Leu Arg
        35                  40                  45

Tyr Tyr Tyr Thr Val Asp Gly Gln Lys Asp Gln Thr Phe Trp Cys Asp
    50                  55                  60

His Ala Ala Ile Ile Gly Ser Asn Gly Ser Tyr Asn Gly Ile Thr Ser
65                  70                  75                  80

Asn Val Lys Gly Thr Phe Val Lys Met Ser Ser Ser Thr Asn Asn Ala
                85                  90                  95

Asp Thr Tyr Leu Glu Ile Ser Phe Thr Gly Gly Thr Leu Glu Pro Gly
            100                 105                 110

Ala His Val Gln Ile Gln Gly Arg Phe Ala Lys Asn Asp Trp Ser Asn
        115                 120                 125

Tyr Thr Gln Ser Asn Asp Tyr Ser Phe Lys Ser Ala Ser Gln Phe Val
    130                 135                 140

Glu Trp Asp Gln Val Thr Ala Tyr Leu Asn Gly Val Leu Val Trp Gly
145                 150                 155                 160

Lys Glu Pro Gly Gly Ser Val Val Pro Ser Thr Gln Pro Val Thr Thr
                165                 170                 175

Pro Pro Ala Thr Thr Thr Pro Thr Pro Thr Ala Thr Pro Ala Pro Thr
            180                 185                 190

Val Thr Pro Thr Pro Thr Pro Thr Pro Ser Thr Pro Thr Ala Thr
    195                 200                 205

Pro Thr Ala Thr Pro Thr Pro Thr Pro Ser Ser Thr Pro Thr
        210                 215                 220

Pro Thr Pro Thr Ala Thr Pro Ala Pro Thr Val Thr Pro Thr Pro Thr
225                 230                 235                 240

Pro Thr Pro Thr Ser Thr Pro Thr Ala Thr Pro Thr Ala Thr Pro Thr
                245                 250                 255

Pro Lys Pro Pro Ala Thr Thr Lys Pro Pro Ala Thr Thr Ile Pro Pro
            260                 265                 270

Ser Gly Ser Asp Leu Gln Val Asp Ile Gly Ser Thr Ser Gly Lys Ala
        275                 280                 285

Gly Ser Val Val Ser Val Pro Ile Thr Phe Thr Asn Val Pro Lys Ser
    290                 295                 300

Gly Ile Tyr Ala Leu Ser Phe Arg Thr Asn Phe Asp Pro Gln Lys Val
305                 310                 315                 320

Thr Val Ala Ser Ile Asp Ala Gly Ser Leu Ile Glu Asn Ala Ser Asp
                325                 330                 335

Phe Thr Thr Tyr Tyr Asn Asn Glu Asn Gly Phe Ala Ser Met Thr Phe
            340                 345                 350

Glu Ala Pro Val Asp Arg Ala Arg Ile Ile Asp Ser Asp Gly Val Phe
        355                 360                 365

Ala Thr Ile Asn Phe Lys Val Ser Asp Ser Ala Lys Val Gly Glu Leu
    370                 375                 380

Tyr Asn Ile Thr Thr Asn Ser Ala Tyr Thr Ser Phe Tyr Tyr Ser Gly
385                 390                 395                 400

Thr Asp Glu Ile Lys Asn Val Val Tyr Asn Asp Gly Lys Ile Glu Val
                405                 410                 415
```

```
Ile Ala Ser Pro Thr Pro Thr Gln Ser Ala Thr Pro Thr Val Thr Pro
            420                 425                 430

Ser Ala Thr Ala Thr Pro Thr Gln Ser Ala Thr Pro Thr Val Thr Pro
        435                 440                 445

Thr Pro Thr Pro Thr Ala Thr Pro Ala Pro Thr Val Thr Pro Thr Pro
    450                 455                 460

Thr Pro Thr Pro Thr Ser Thr Pro Thr Ala Thr Pro Thr Ala Thr Pro
465                 470                 475                 480

Thr Pro Thr Pro Thr Ser Ser Thr Pro Thr Pro Thr Pro Thr Ala Thr
                485                 490                 495

Pro Ala Pro Thr Val Thr Pro Thr Pro Thr Pro Thr Pro Thr Ser Thr
                500                 505                 510

Pro Thr Ala Thr Pro Thr Ala Thr Pro Thr Pro Ser Asp Gly Val Val
            515                 520                 525

Val Glu Ile Gly Lys Val Thr Gly Ser Val Gly Thr Thr Val Glu Ile
530                 535                 540

Pro Val Tyr Phe Arg Gly Val Pro Ser Lys Gly Ile Ala Asn Cys Asp
545                 550                 555                 560

Phe Val Phe Arg Tyr Asp Pro Asn Val Leu Glu Ile Ile Gly Ile Asp
                565                 570                 575

Pro Gly Asp Ile Ile Val Asp Pro Asn Pro Thr Lys Ser Phe Asp Thr
            580                 585                 590

Ala Ile Tyr Pro Asp Arg Lys Ile Ile Val Phe Leu Phe Ala Glu Asp
        595                 600                 605

Ser Gly Thr Gly Ala Tyr Ala Ile Thr Lys Asp Gly Val Phe Ala Lys
    610                 615                 620

Ile Arg Ala Thr Val Lys Ser Ser Ala Pro Gly Tyr Ile Thr Phe Asp
625                 630                 635                 640

Glu Val Gly Gly Phe Ala Asp Asn Asp Leu Val Glu Gln Lys Val Ser
                645                 650                 655

Phe Ile Asp Gly Gly Val Asn Val Gly Asn Ala Thr Leu Glu His His
            660                 665                 670

His His His His
        675

<210> SEQ ID NO 38
<211> LENGTH: 668
<212> TYPE: PRT
<213> ORGANISM: Artificial Sequence
<220> FEATURE:
<223> OTHER INFORMATION: Synthetic polypeptide

<400> SEQUENCE: 38

Met Ala Asn Thr Pro Val Ser Gly Asn Leu Lys Val Glu Phe Tyr Asn
1               5                   10                  15

Ser Asn Pro Ser Asp Thr Thr Asn Ser Ile Asn Pro Gln Phe Lys Val
                20                  25                  30

Thr Asn Thr Gly Ser Ser Ala Ile Asp Leu Ser Lys Leu Thr Leu Arg
            35                  40                  45

Tyr Tyr Tyr Thr Val Asp Gly Gln Lys Asp Gln Thr Phe Trp Cys Asp
        50                  55                  60

His Ala Ala Ile Ile Gly Ser Asn Gly Ser Tyr Asn Gly Ile Thr Ser
65                  70                  75                  80

Asn Val Lys Gly Thr Phe Val Lys Met Ser Ser Ser Thr Asn Asn Ala
                85                  90                  95
```

```
Asp Thr Tyr Leu Glu Ile Ser Phe Thr Gly Gly Thr Leu Glu Pro Gly
            100                 105                 110

Ala His Val Gln Ile Gln Gly Arg Phe Ala Lys Asn Asp Trp Ser Asn
            115                 120                 125

Tyr Thr Gln Ser Asn Asp Tyr Ser Phe Lys Ser Ala Ser Gln Phe Val
            130                 135                 140

Glu Trp Asp Gln Val Thr Ala Tyr Leu Asn Gly Val Leu Val Trp Gly
145                 150                 155                 160

Lys Glu Pro Gly Gly Ser Val Val Pro Ser Thr Gln Pro Val Thr Thr
                165                 170                 175

Pro Pro Ala Thr Thr Pro Val Thr Pro Thr Ile Pro Pro Thr Pro
            180                 185                 190

Thr Pro Thr Ala Thr Pro Ala Pro Thr Val Thr Pro Thr Pro Thr Pro
            195                 200                 205

Thr Pro Thr Ser Thr Pro Thr Ala Thr Pro Ala Thr Pro Thr Pro
            210                 215                 220

Thr Pro Thr Pro Ser Ser Thr Pro Thr Pro Thr Pro Thr Ala Thr Pro
225                 230                 235                 240

Ala Pro Thr Val Thr Pro Thr Pro Thr Pro Thr Pro Thr Ser Thr Pro
                245                 250                 255

Thr Ala Thr Pro Thr Ala Thr Pro Thr Pro Thr Pro Thr Pro Ser Ser
            260                 265                 270

Thr Pro Ser Ser Ser Pro Gly Asn Lys Met Lys Ile Gln Ile Gly Asp
            275                 280                 285

Val Lys Ala Asn Gln Gly Asp Thr Val Ile Val Pro Ile Thr Phe Asn
290                 295                 300

Glu Val Pro Val Met Gly Val Asn Asn Cys Asn Phe Thr Leu Ala Tyr
305                 310                 315                 320

Asp Lys Asn Ile Met Glu Phe Ile Ser Ala Asp Ala Gly Asp Ile Val
            325                 330                 335

Thr Leu Pro Met Ala Asn Tyr Ser Tyr Asn Met Pro Ser Asp Gly Leu
            340                 345                 350

Val Lys Phe Leu Tyr Asn Asp Gln Ala Gln Gly Ala Met Ser Ile Lys
            355                 360                 365

Glu Asp Gly Thr Phe Ala Asn Val Lys Phe Lys Ile Lys Gln Ser Ala
            370                 375                 380

Ala Phe Gly Lys Tyr Ser Val Gly Ile Lys Ala Ile Gly Ser Ile Ser
385                 390                 395                 400

Ala Leu Ser Asn Ser Lys Leu Ile Pro Ile Glu Ser Ile Phe Lys Asp
                405                 410                 415

Gly Ser Ile Thr Val Thr Asn Thr Pro Thr Asn Thr Pro Thr Pro Thr
            420                 425                 430

Ala Thr Pro Ala Pro Thr Val Thr Pro Thr Pro Thr Pro Thr Pro Thr
            435                 440                 445

Ser Thr Pro Thr Ala Thr Pro Thr Ala Thr Pro Thr Pro Thr Pro Thr
            450                 455                 460

Pro Ser Ser Thr Pro Thr Pro Thr Pro Thr Ala Thr Pro Ala Pro Thr
465                 470                 475                 480

Val Thr Pro Thr Pro Thr Pro Thr Pro Thr Ser Thr Pro Thr Ala Thr
                485                 490                 495

Pro Thr Ala Thr Pro Thr Pro Thr Pro Thr Pro Ser Ser Thr Pro Thr
            500                 505                 510
```

```
Val Thr Pro Ser Asp Gly Val Val Glu Ile Gly Lys Val Thr Gly
        515                 520                 525

Ser Val Gly Thr Thr Val Glu Ile Pro Val Tyr Phe Arg Gly Val Pro
    530                 535                 540

Ser Lys Gly Ile Ala Asn Cys Asp Phe Val Phe Arg Tyr Asp Pro Asn
545                 550                 555                 560

Val Leu Glu Ile Ile Gly Ile Asp Pro Gly Asp Ile Ile Val Asp Pro
                565                 570                 575

Asn Pro Thr Lys Ser Phe Asp Thr Ala Ile Tyr Pro Asp Arg Lys Ile
            580                 585                 590

Ile Val Phe Leu Phe Ala Glu Asp Ser Gly Thr Gly Ala Tyr Ala Ile
        595                 600                 605

Thr Lys Asp Gly Val Phe Ala Lys Ile Arg Ala Thr Val Lys Ser Ser
        610                 615                 620

Ala Pro Gly Tyr Ile Thr Phe Asp Glu Val Gly Gly Phe Ala Asp Asn
625                 630                 635                 640

Asp Leu Val Glu Gln Lys Val Ser Phe Ile Asp Gly Gly Val Asn Val
                645                 650                 655

Gly Asn Ala Thr Leu Glu His His His His His His
                660                 665

<210> SEQ ID NO 39
<211> LENGTH: 7
<212> TYPE: PRT
<213> ORGANISM: Artificial Sequence
<220> FEATURE:
<223> OTHER INFORMATION: Synthetic linker polypeptide

<400> SEQUENCE: 39

Pro Thr Pro Thr Pro Thr Pro
1               5
```

ENZYME SCAFFOLDS AND METHODS OF USE

CROSS-REFERENCE TO RELATED APPLICATIONS

This application claims priority to U.S. Provisional Application Nos. 62/312,158 and 62/312,220, both of which were filed on Mar. 23, 2016, the entire disclosure of which are expressly incorporated herein by reference for all purposes.

CONTRACTUAL ORIGIN

United States Government has rights in this disclosure under Contract No. DE-AC36-08GO28308 between the United States Department of Energy and Alliance for Sustainable Energy, LLC, the Manager and Operator of the National Renewable Energy Laboratory.

SEQUENCE LISTING

The instant application contains a Sequence Listing which has been submitted via EFS-web and is hereby incorporated by reference in its entirety. The ASCII copy, created on Mar. 22, 2017, is named 15-81_ST25.txt, and is 94,412 bytes in size.

BACKGROUND

Biofuels and biochemicals derived from lignocellulosic biomass represent an alternative to petroleum-based transportation fuels and other chemicals that take advantage of an abundant and renewable resource while not utilizing food crops as feedstocks. Cellulose and hemicellulose found in biomass, however, must first be converted to fermentable sugars, which are in turn converted to biofuels such as ethanol and biodiesel, and biochemical building blocks such as 3-hydroxypropionic acid, by fermentative organisms.

Several key factors negatively impact the production yield, and thus the cost of biofuels and biochemicals from renewable sources. Common hindrances in the biological production of biofuels and biochemicals include: (1) intermediate and end-product toxicity to the fermentative organisms, (2) the diversion of carbon to biomass formation, and (3) co-production of undesired byproducts, among others. An alternative is to eliminate the fermentative organisms entirely and instead operate the desired metabolic pathway in isolation, thus circumventing the roadblock of biological toxicity and lack of specificity. However, in vitro enzyme systems suffer from low productivities owing in part to the effects of free diffusion of intermediates within metabolic pathways, lack of long term enzyme stability, cofactor cost or inefficient recycling rates, and cost of enzyme production.

SUMMARY

The present disclosure provides enzymatic polypeptide scaffolds that take advantage of the strength, high specificity and affinity protein/protein interaction between the cohesins and dockerins of microorganismal cellulosomes.

In a first aspect, the present disclosure provides enzymatic polypeptide scaffolds, comprising: a first linker domain, a first cohesin domain, and a second cohesin domain, wherein the linker domain interconnects the first and second cohesin domains; a first recombinant polypeptide comprising a first dockerin domain and a first catalytic domain, the first catalytic domain corresponding to a first enzyme of interest, wherein the first dockerin domain selectively binds to the first cohesin domain; and a second recombinant polypeptide comprising a second dockerin domain and a second catalytic domain, the second catalytic domain corresponding to a second enzyme of interest, wherein the second dockerin domain selectively binds to the second cohesin domain.

In some embodiments, the enzymatic polypeptide scaffolds further comprise a second linker domain and a third cohesin domain, wherein the second linker domain interconnects the second and third cohesin domains; and a third recombinant polypeptide comprising a third dockerin domain and a third catalytic domain, the third catalytic domain corresponding to a third enzyme of interest, wherein the third dockerin domain selectively binds to the third cohesin domain.

In some embodiments, the enzymatic polypeptide scaffolds further comprise a surface anchoring domain and an anchoring linker domain, wherein the anchoring linker domain interconnects the surface anchoring domain and the first cohesin domain.

In some embodiments, the enzymatic polypeptide scaffolds further comprise: a first polypeptide linker between the first dockerin domain and the first catalytic domain, and optionally a second polypeptide linker between the second dockerin domain and the second catalytic domain, and a third polypeptide linker between the third dockerin domain and the third catalytic domain.

In some embodiments, the surface anchoring domain is a cellulose binding domain.

In some embodiments, the first linker and the second linker are each independently a synthetic linker having an amino acid sequence that is 95% identical to an amino acid sequence selected from SEQ ID NOS: 1-7.

In some embodiments, the present disclosure provides enzymatic polypeptide scaffold arrays, comprising: a first enzymatic polypeptide scaffold as set forth above but also further comprising a first adapter linker and a first adapter dockerin, the first adapter linker interconnecting the first adapter dockerin and the first cohesin domain of the first scaffold; a second enzymatic polypeptide scaffold as set forth above, but also further comprising a second adapter linker and a second adapter dockerin, the second adapter linker interconnecting the second adapter dockerin and the first cohesin domain of the second scaffold; and an adapter scaffold comprising two adapter cohesin domains and an adapter linker domain that interconnects the two adapter cohesins.

In some embodiments, the first and second adapter dockerins selectively bind to the adapter cohesin domains. In some embodiments, the adapter scaffold interconnects the first and second enzymatic polypeptide scaffolds.

In a second aspect, the present disclosure provides enzymatic polypeptide scaffolds, comprising: a first linker domain, a first cohesin domain, and a second cohesin domain, wherein the linker domain interconnects the first and second cohesin domains; a first recombinant polypeptide comprising a first dockerin domain and a glycerol dehydrogenase catalytic domain, wherein the first dockerin domain selectively binds to the first cohesin domain; and a second recombinant polypeptide comprising a second dockerin domain and a aldehyde dehydrogenase catalytic domain, wherein the second dockerin domain selectively binds to the second cohesin domain.

In some embodiments, the enzymatic polypeptide scaffolds further comprise: a second linker domain and a third cohesin domain, wherein the second linker domain interconnects the second and third cohesin domains; and a third recombinant polypeptide comprising a third dockerin domain and an NADH oxidase catalytic domain, wherein the third dockerin domain selectively binds to the third cohesin domain.

In some embodiments, the enzymatic polypeptide scaffolds further comprise a surface anchoring domain and an anchoring linker domain, wherein the anchoring linker domain interconnects the surface anchoring domain and the first cohesin domain.

In some embodiments, the enzymatic polypeptide scaffolds further comprise: a first polypeptide linker between the first dockerin domain and the glycerol dehydrogenase catalytic domain, a second polypeptide linker between the second dockerin domain and the aldehyde dehydrogenase catalytic domain, and a third polypeptide linker between the third dockerin domain and the NADH oxidase catalytic domain.

In some embodiments, the glycerol dehydrogenase catalytic domain has an amino acid sequence that is at least 90% identical to SEQ ID NO: 8 or a catalytic domain thereof and the aldehyde dehydrogenase domain has an amino acid sequence that is at least 90% identical to SEQ ID NO: 9 or a catalytic domain thereof.

In some embodiments, the NADH oxidase catalytic domain has an amino acid sequence that is at least 90% identical to SEQ ID NO: 10.

In some embodiments, the surface anchoring domain is a cellulose binding domain.

In some embodiments, the first linker and the second linker are each independently a synthetic linker having an amino acid sequence that is 95% identical to an amino acid sequence selected from SEQ ID NOS: 1-7.

In a third aspect, the present disclosure provides enzymatic polypeptide scaffold arrays, comprising:

a first enzymatic polypeptide scaffold comprising: a first linker domain, a first cohesin domain, and a second cohesin domain, wherein the linker domain interconnects the first and second cohesin domains; a first recombinant polypeptide comprising a first dockerin domain and a glycerol dehydrogenase catalytic domain, wherein the first dockerin domain selectively binds to the first cohesin domain; and a second recombinant polypeptide comprising a second dockerin domain and a aldehyde dehydrogenase catalytic domain, wherein the second dockerin domain selectively binds to the second cohesin domain; a first adapter linker and a first adapter dockerin, the first adapter linker interconnecting the first adapter dockerin and the first cohesin domain of the first scaffold;

a second enzymatic polypeptide scaffold comprising: a first linker domain, a first cohesin domain, and a second cohesin domain, wherein the linker domain interconnects the first and second cohesin domains; a first recombinant polypeptide comprising a first dockerin domain and a glycerol dehydrogenase catalytic domain, wherein the first dockerin domain selectively binds to the first cohesin domain; and a second recombinant polypeptide comprising a second dockerin domain and a aldehyde dehydrogenase catalytic domain, wherein the second dockerin domain selectively binds to the second cohesin domain; a second adapter linker and a second adapter dockerin, the second adapter linker interconnecting the second adapter dockerin and the first cohesin domain of the second scaffold; and an adapter scaffold comprising two adapter cohesin domains and an adapter linker domain that interconnects the two adapter cohesins.

In some embodiments, the first and second adapter dockerins selectively bind to the adapter cohesin domains. In some embodiments, the adapter scaffold interconnects the first and second enzymatic polypeptide scaffolds.

In a fourth aspect, the present disclosure provides methods for producing 3-hydroxypropionic acid from glycerol, comprising:

applying glycerol in a solution to an enzymatic polypeptide scaffold comprising: a first linker domain, a first cohesin domain, and a second cohesin domain, wherein the linker domain interconnects the first and second cohesin domains; a first recombinant polypeptide comprising a first dockerin domain and a glycerol dehydrogenase catalytic domain, wherein the first dockerin domain selectively binds to the first cohesin domain; and a second recombinant polypeptide comprising a second dockerin domain and a aldehyde dehydrogenase catalytic domain, wherein the second dockerin domain selectively binds to the second cohesin domain;

incubating the glycerol with the scaffold, and
recovering 3-hydroxypropionic acid.

In a fifth aspect, the present disclosure provides enzymatic polypeptide scaffolds comprising: a first linker domain, a first cohesin domain, and a second cohesin domain, wherein the linker domain interconnects the first and second cohesin domains; a first recombinant polypeptide comprising a first dockerin domain and an acetolactase synthase catalytic domain, wherein the first dockerin domain selectively binds to the first cohesin domain; and a second recombinant polypeptide comprising a second dockerin domain and an acetolactase decarboxylase catalytic domain, wherein the second dockerin domain selectively binds to the first cohesin domain.

In some embodiments, the enzymatic polypeptide scaffolds further comprise: a second linker domain and a third cohesin domain, wherein the second linker domain interconnects the second and third cohesin domains; and a third recombinant polypeptide comprising a third dockerin domain and a butanediol dehydrogenase catalytic domain, wherein the third dockerin domain selectively binds to the third cohesin domain.

In some embodiments, the enzymatic polypeptide scaffolds further comprise a surface anchoring domain and an anchoring linker domain, wherein the anchoring linker domain interconnects the surface anchoring domain and the first cohesin domain.

In some embodiments, the enzymatic polypeptide scaffolds further comprise: a first polypeptide linker between the first dockerin domain and the acetolactate synthase catalytic domain, a second polypeptide linker between the second dockerin domain and the acetolactate decarboxylase catalytic domain, and a third polypeptide linker between the third dockerin domain and the butanediol dehydrogenase catalytic domain.

In some embodiments, the acetolactate synthase catalytic domain has an amino acid sequence that is at least 90% identical to SEQ ID NO: 21 or a catalytic domain thereof and the acetolactate decarboxylase domain has an amino acid sequence that is at least 90% identical to SEQ ID NO: 22 or a catalytic domain thereof.

In some embodiments, the butanediol dehydrogenase catalytic domain has an amino acid sequence that is at least 90% identical to SEQ ID NO: 23.

In some embodiments, the surface anchoring domain is a cellulose binding domain.

In some embodiments, the first linker and the second linker are each independently a synthetic linker having an amino acid sequence that is 95% identical to an amino acid sequence selected from SEQ ID NOS: 1-7.

In a sixth aspect, the present disclosure provides enzymatic polypeptide scaffold arrays, comprising:

a first enzymatic polypeptide scaffold comprising a first linker domain, a first cohesin domain, and a second cohesin domain, wherein the linker domain interconnects the first and second cohesin domains; a first recombinant polypeptide comprising a first dockerin domain and an acetolactase synthase catalytic domain, wherein the first dockerin domain selectively binds to the first cohesin domain; and a second recombinant polypeptide comprising a second dockerin domain and an acetolactase decarboxylase catalytic domain, wherein the second dockerin domain selectively binds to the first cohesin domain; a first adapter linker and a first adapter dockerin, wherein the first adapter linker interconnects the first adapter dockerin and the first cohesin domain of the first scaffold;

a second enzymatic polypeptide scaffold comprising a first linker domain, a first cohesin domain, and a second cohesin domain, wherein the linker domain interconnects the first and second cohesin domains; a first recombinant polypeptide comprising a first dockerin domain and an acetolactase synthase catalytic domain, wherein the first dockerin domain selectively binds to the first cohesin domain; and a second recombinant polypeptide comprising a second dockerin domain and an acetolactase decarboxylase catalytic domain, wherein the second dockerin domain selectively binds to the first cohesin domain; a second adapter linker and a second adapter dockerin, wherein the second adapter linker interconnects the second adapter dockerin and the first cohesin domain of the second scaffold; and an adapter scaffold comprising two adapter cohesin domains and an adapter linker domain that interconnects the adapter cohesins.

In some embodiments, the first and second adapter dockerins selectively bind to the adapter cohesin domains. In some embodiments, the adapter scaffold interconnects the first and second enzymatic polypeptide scaffolds.

In a seventh aspect, the present disclosure provides methods for producing 2,3 butanediol from pyruvate, comprising:

applying pyruvate in a solution to an enzymatic polypeptide scaffold comprising a first linker domain, a first cohesin domain, and a second cohesin domain, wherein the linker domain interconnects the first and second cohesin domains; a first recombinant polypeptide comprising a first dockerin domain and an acetolactase synthase catalytic domain, wherein the first dockerin domain selectively binds to the first cohesin domain; and a second recombinant polypeptide comprising a second dockerin domain and an acetolactase decarboxylase catalytic domain, wherein the second dockerin domain selectively binds to the first cohesin domain;

incubating the glycerol with the scaffold, and recovering 2,3 butanediol.

DETAILED DESCRIPTION

Figure 1:
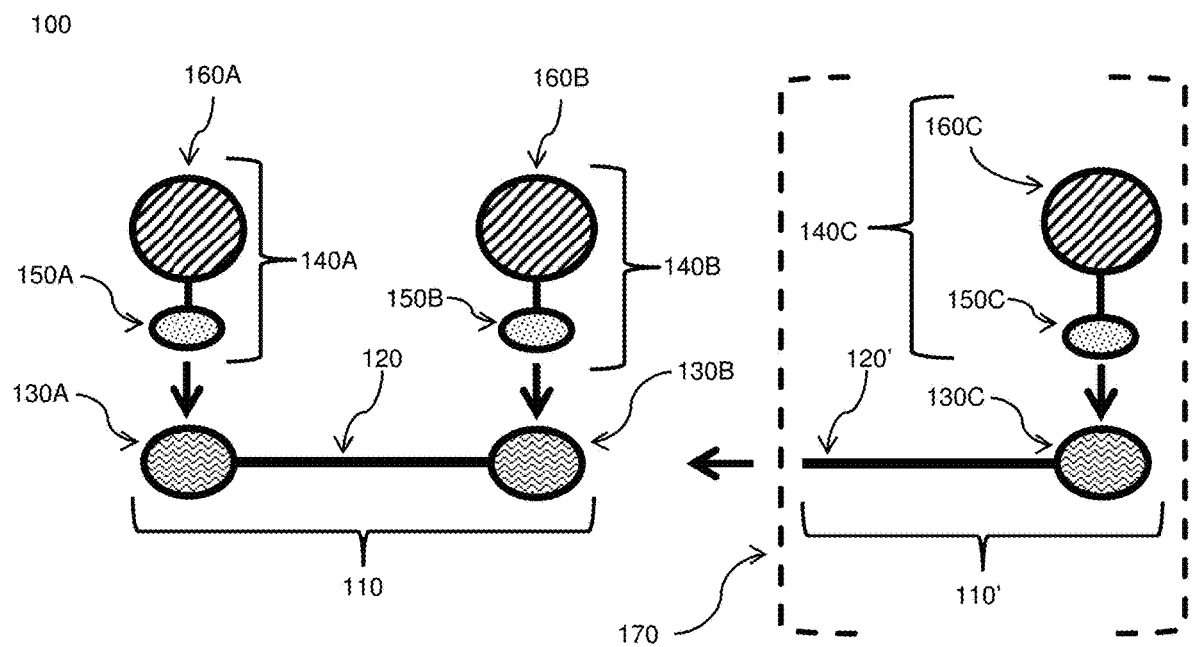
FIG. 1 is an illustration depicting a two-enzyme enzymatic polypeptide scaffold and optional repeated subunit according to one embodiment.

In the following sections, various exemplary compositions and methods are described in order to detail various embodiments. It will be evident to one skilled in the art that practicing the various embodiments does not require the employment of all of the specific details outlined herein, but rather that linker length, fusion polypeptide structure and other specific details may be modified through experimentation. In some embodiments, well known methods or components have not been included in the description.

In various aspects, the present disclosure provides synthetic enzymatic polypeptide scaffolds. An enzymatic polypeptide scaffold can comprise some or all of the enzymes of a particular metabolic pathway. The synthetic enzymatic polypeptide scaffolds described herein utilize the highly selective, high affinity protein-protein interactions observed in cellulosomes of several species of bacteria and fungi. Cellulosomes evolved in some cellulose-degrading microorganisms as supramolecular complexes that function as nanomachines; they have the capability to organize in a self-promoted manner on bacterial and fungal cell surfaces, adhere to plant materials, and degrade plant cell wall lignocellulose. Cellulosomes are multi-enzyme systems containing a division of enzymatic subunits, each designed for degrading specific components of a given substrate. Within a cellulosome, multiple endoglucanases, cellobiohydrolases, xylanases and other degradative enzymes work synergistically to attack heterogeneous, insoluble cellulose substrates. The enzymes are situated along a single scaffold, known as scaffoldin. Scaffoldin, a glycoprotein, is not itself the catalytically active part of the cellulosome macrostructure. Instead, scaffoldin has the purpose of organizing the catalytic enzymes (e.g., cellulases, xylanases) displayed on the cellulosome at high density, and subsequently targeting the entire complex to the plant material via a cellulose-binding module (CBM).

In order to integrate the enzymes into the cellulosome and order them along the scaffoldin, nature has developed a high-specificity, high-affinity protein-protein interaction known as the cohesin-dockerin interaction. Cohesin domains, which are embedded in the scaffoldin, bind dockerin polypeptides with great selectivity, affinity and strength. The degradative enzymes are linked to the dockerin polypeptides, and are thus bound to the scaffoldin protein in an ordered fashion through the cohesin/dockerin interaction.

In certain embodiments described herein, the cohesin/dockerin interactions of cellulosomes can be adapted to create synthetic enzymatic polypeptide scaffolds having an ordered array of recombinant target polypeptides having enzymatic activity. In some embodiments, synthetic enzymatic polypeptide scaffolds comprise an ordered array of recombinant target polypeptides that form all or part of a metabolic pathway. Such scaffolds can then be used in the production of desired end products or valuable intermediates for use in other processes.

Turning to FIG. 1, in various aspects, an enzymatic polypeptide scaffold 100 provided by the present disclosure comprises: (1) a recombinant scaffold polypeptide 110 that comprises a linker domain 120 and two distinct cohesin domains (130A and 130B); and (2) two recombinant target polypeptides 140 (140A and 140B) that each comprise a distinct dockerin domain 150 (150A and 150B) and a distinct enzymatic catalytic domain 160 (160A and 160B). In some embodiments, a recombinant target polypeptide 140 comprises an enzyme linked to a dockerin polypeptide. Each dockerin domain 150 is selected to specifically bind one cohesin domain 130 of the recombinant scaffold polypeptide 110. In FIG. 1, for example, dockerin domain 150A specifically binds to cohesin domain 130A, and dockerin domain 150B specifically binds to cohesin domain 130B. Dockerin domain 150A does not bind to cohesin domain 130B, and dockerin domain 150B does not bind to cohesin domain 130A. This specificity allows the recombinant target polypeptides 140A and 140B (and thus catalytic domains 160A and 160B) to be ordered along the recombinant scaffold polypeptide 110 according to the cohesin/dockerin binding pairs.

In some embodiments, the enzymatic polypeptide scaffold 100 can comprise repeats of a scaffold subunit 170, which comprises (1) a recombinant scaffold polypeptide 110' that comprises a linker domain 120' and a cohesin domain 130C; and (2) a recombinant target polypeptide 140C that comprises a dockerin domain 150C and an enzymatic catalytic domain 160C. In some embodiments, the binding of cohesin domain 130C to dockerin domain 150C is specific such that, if a repeat scaffold unit 170 is added to the enzymatic polypeptide scaffold 100, dockerin domain 150C—and thus enzyme catalytic domain 160C—will not bind to cohesin domains 130A or 130B, thereby allowing the ordering of enzymatic catalytic domains along the scaffold 100. Multiple scaffold subunits 170 can be present, resulting in an enzymatic polypeptide scaffold having three or more cohesin domains 130, each binding to a specific recombinant target polypeptide 140 via a dockerin domain 150. In certain embodiments, where multiple scaffold subunits 170 are present, each multiple scaffold subunit can comprise a unique cohesin 130 and recombinant target polypeptide 140. That is, similarly to how cohesin domains 130A and 130B each selectively pair with recombinant target proteins 140A and 140B, respectively, via dockerin domains 150A and 150B, each scaffold subunit 170 can comprise a unique cohesin/recombinant target polypeptide pairing via selective cohesin/dockerin binding. Including one or more scaffold repeat subunits 170 in the enzymatic polypeptide scaffold 100 can result in an ordered metabolic pathway. In certain embodiments, an enzymatic polypeptide scaffold 100 can comprise 1 to 10 scaffold repeat subunits 170, resulting in an enzymatic polypeptide scaffold 100 totaling 3 to 12 cohesin/recombinant target polypeptide pairs. In some embodiments, an enzymatic polypeptide scaffold 100 comprises no additional scaffold repeat subunits 170, in which case the scaffold 100 comprises two cohesin/recombinant target polypeptides pairs. In some embodiments, an enzymatic polypeptide scaffold 100 comprises one scaffold repeat subunit 170 (three cohesin/recombinant target polypeptides pairs), in some embodiments two scaffold subunits 170 (four cohesin/recombinant target polypeptides pairs), in some embodiments three scaffold subunits 170 (five cohesin/recombinant target polypeptides pairs).

Figure 2:
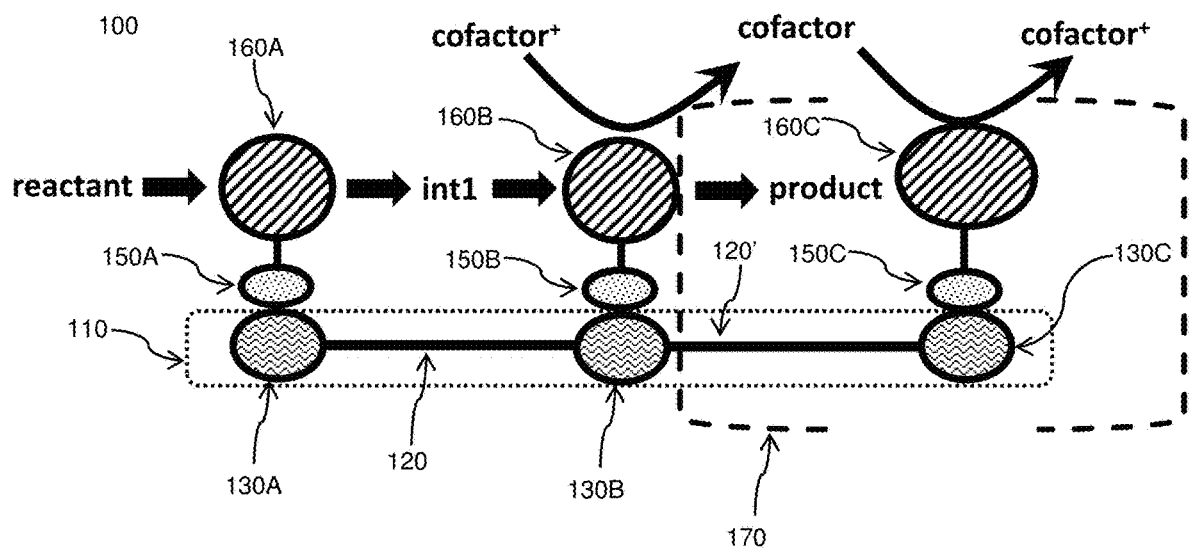
FIG. 2 is an illustration depicting a three-enzyme enzymatic polypeptide scaffold comprising a cofactor recycling enzyme according to one embodiment.

FIG. 2 illustrates a simple enzymatic polypeptide scaffold 100 that comprises three ordered enzymes. In reference to FIG. 1, FIG. 2 comprises a basic two cohesin/recombinant target protein scaffold 100 and a single additional scaffold repeat subunit 170. Cohesin domains 130A, 130B, and 130C of FIG. 2 are linked via linker domains 120 and 120'. Cohesin 130A exclusively binds with dockerin 150A, which is linked to enzyme A (i.e., enzymatic catalytic domain) 160A. Cohesin 130B and 130C similarly bind exclusively to dockerin 150B and 150C, respectively, resulting in enzymes 160A, 160B, and 160C being ordered linearly along the enzymatic polypeptide scaffold 100.

Cohesin/Dockerin Pairs

In some embodiments, the cohesin/dockerin pairs to be used in an enzymatic polypeptide scaffold are selected from naturally occurring cohesin/dockerin pairs. The interaction between cohesins and dockerins is among the highest affinity protein-protein interactions in nature, with a dissociation constant ($K_D$) of $<10^{-11}$ M. Cohesins generally interact with dockerins in a species specific manner. That is, they bind with very high affinity to dockerins of the same species, failing to bind to dockerins of other species. Certain species are known to have multiple cohesins and/or dockerins. Even within a given species, certain dockerins may only selectively bind a given cohesin with high affinity. Further, studies have shown some cross-reactivity of cohesins and dockerins between species. Therefore, care should be taken when selecting cohesin dockerin pairs to include in an enzymatic polypeptide scaffold described herein. For example, when a particular dockerin binds not only to its cohesin target from the same species but also that of another species, the particular dockerin should be selected for use if only one of its possible cohesin binding partners is present on the scaffold polypeptide, unless more than one copy of that dockerin is desired along the scaffold. Otherwise the recombinant target protein that comprises the particular dockerin will bind to both possible cohesin binding partners and occupy a cohesin domain binding site intended for a different recombinant target protein.

As described herein, the high-affinity, high-selectivity of cohesion/dockerin pairing can be harnessed to engineer enzymatic polypeptide scaffolds with ordered enzymes. Cohesins/dockerin pairs can be those from, for example, bacteria including but not limited to *Acidothermus cellulolyticus, Bacteroides cellulosolvens, Clostridium thermocellum, Clostridium cellulolyticum, Clostridium cellulovarans, Clostridium acetobutylicum, Clostridium josui, Clostridium papyrosolvens, Ruminococcus flavefaciens, Archaeoglobus fulgidus*, anaerobic fungi of the genera *Neocallimastix, Piromyces*, and *Orpinomyces* and combinations of the foregoing. Examples of possible cohesin/cadherin pairs from these organisms can be found in Table 1.

TABLE 1

Representative cohesin/dockerin pairs for use in enzymatic polypeptide scaffolds described herein.

| Species | Dockerin | Cohesin |
|---|---|---|
| *A. cellulolyticus* | Ac-XDocA | Ac-B1 |
|  | Ac-ScaB | Ac-ScaC |
| *B. cellulosolvens* | Bv-48-A | Bc-A5 |
|  | Bc-48-A | Bv-A11 |
|  | Bc-ScaA | Bc-ScaB |

TABLE 1-continued

Representative cohesin/dockerin pairs for use in enzymatic polypeptide scaffolds described herein.

| Species | Dockerin | Cohesin |
|---|---|---|
| *C. thermocellum* | Ct-XDocA | Ct-B1 |
|  | Ct-XDocA | Ct-B4 |
|  | Ct-XDocA | Ct-Sdba |
|  | Ct-XDocA | Ct-O2p2 |
|  | Ct-CipA | Ct-CipA |
| *C. cellulolyticum* | Cc-5A | CC-A1 |
|  | Cc-EndA | cc-CipC |
| *R. flavefaciens* | Rf-44A | Rf-A3 |
|  | Rf-DocA | Rf-B1 |
|  | Rf-DocA | Rf-B6 |
|  | Rf-XDocB | Rf-E |
|  | Rf-DocC | Rf-A3 |
|  | Rf-ScaA | ScaB |
| *A. fulgidus* | Af-Doc | Af-75 |
|  | Af-Doc | Af-76 |

As described, some cross-reactivity of cohesins and dockerins between species has been observed. Table 2 provides non-limiting examples of such inter-species cohesin/dockerin cross-reactivity.

TABLE 2

Representative interspecies cohesin/dockerin pairs.

| | Name | Species |
|---|---|---|
| Dockerin | Bc-48A | *B. cellulosolvens* |
| Cohesin | Ct-Sdba | *C. thermocellum* |
| Dockerin | Ac-XDocA | *A. cellulolyticus* |
| Cohesin | Ct-B1 | *C. thermocellum* |
| Dockerin | Ac-XDocA | *A. cellulolyticus* |
| Cohesin | Ct-Sdba | *C. thermocellum* |
| Dockerin | Ac-XDocA | *A. cellulolyticus* |
| Cohesin | Ct-B1 | *C. thermocellum* |

Recombinant Scaffold Polypeptides and Linker Domains

In certain embodiments, such that illustrated in FIG. 1, a recombinant scaffold polypeptide 110 can comprise two cohesin domains interconnect via a linker domain 120. In embodiments comprising one or more scaffold subunits, the recombinant scaffold peptide 110 is considered to comprise each additional linker domain 120' and each additional cohesin domain 130C. For example, the recombinant scaffold peptide 110 of FIG. 2 comprises, in order, cohesin domain 130A, linker domain 120, cohesin domain 130B, linker domain 120', and cohesin domain 130C. In certain embodiments, the number of cohesion domains 130 of the recombinant scaffold polypeptide 110 will be one greater than the number of linker domains 120.

In some embodiments, the linker domain 120 and one of the cohesin domains 130 are derived from the same bacterial or fungal source.

In nature, the scaffoldin protein is a large glycoprotein that comprises several cohesin domains interspaced by linker regions. In certain embodiments, a cohesin domain and the following linker region—i.e., the polypeptide occurring between two cohesin domains—can be adapted for use according to the embodiments described herein. For example, in the embodiment depicted in FIG. 1, the enzymatic polypeptide scaffold 100 comprises a cohesin domain 130A and linker domain 120 derived from a single scaffoldin. The second cohesin domain 130B is linked to the distal end of the linker domain 120 relative to cohesin domain 130A, as depicted. In some embodiments, the linker domain 120 is truncated or otherwise mutated, so long as the truncation or mutation does not affect the three-dimensional structure of the linker domain. Possible mutations include, for example, insertion mutations, deletion mutations, and point mutations. Certain modifications may be required in order to join the linker domain to cohesin domain 130B. Such modifications and methods for joining the peptides are known in the art.

Referring now to FIG. 2, in embodiments where the recombinant scaffold polypeptide comprises three cohesin domains, one or both of the linker domains 120 can be derived from a scaffoldin. In some embodiments, for example, cohesin domain 130A and linker domain 120 are derived from a scaffoldin protein of a first species, while cohesin domain 130B and linker domain 120' are derived from a scaffoldin protein of a second species, and cohesin domain 130C is from yet another species and is linked to the end of linker domain 120' distal to cohesin domain 130B. Various alternate arrangements are also possible. For example, linker domains 120 and 120', and cohesin domain 130B can all be derived from the scaffoldin protein of a particular species. Cohesin domains 130A and 130C are positioned at either end of the scaffold polypeptide 110. In another possible arrangement, cohesin domain 130A and linker domain 120 are derived from a scaffoldin protein of a first species, while cohesin domain 130C and linker domain 120' are derived from a scaffoldin protein of a second species. Cohesin domain 130B is from yet another species, and is positioned between linker domains 120 and 120'. In embodiments where the scaffold polypeptide 110 comprises more than three cohesion domains, the cohesin domains 130 and linker domains 120 can be similarly arranged.

In certain embodiments, the linker domain(s) 120 are synthetic polypeptides. In some embodiments, the linker domains are flexible so that the interconnected cohesin domains are free to move relative to one another. In some embodiments, the linker domain is synthetic and glycine rich. The glycine content of synthetic linker domains can range from about 50% to 100%. In some embodiments, the glycine content of a synthetic linker domain comprises about 50% or more glycine residues. In certain embodiments, those residues of the synthetic linker domain that are not glycine are hydrophilic amino acid residues such as, for example, arginine, aspartic acid, glutamic acid, asparagine, glutamine, serine, threonine, and/or tyrosine. In some embodiments, over 50% of the synthetic linker domain comprises hydrophilic amino acid residues. In some embodiments, about 50% to 100% of the synthetic linker domain comprises hydrophilic amino acid residues. In other embodiments, the synthetic linker domain comprises a sequence of any combination of residues where the resulting synthetic linker domain is substantially linear and free of tertiary structure, and in some embodiments, also free of secondary structure.

According to some embodiments, the synthetic linker domains have an amino acid sequence that lacks substantial identity with naturally occurring protein sequences so as to avoid potential interactions with the target proteins or to limit the probability of scaffold polypeptide degradation by proteases. In certain embodiments, the synthetic linker domains have an amino acid sequence that has 50% or less identity with known naturally occurring protein sequences. Percent identity of a synthetic linker domain to a naturally occurring protein can be determined by, for example, the National Center for Biotechnology Information's (NCBI) protein Basic Local Alignment Search Tool (BLAST), although other algorithms may be used.

In certain embodiments, a synthetic linker domain is a linear polypeptide. In some embodiments, a synthetic linker domain can lack tertiary structure, lack secondary structure, or lack both.

In particular embodiments, a scaffold polypeptide 110 can comprise a mixture of synthetic linker domains and linker domains derived from one or more naturally occurring scaffoldin proteins.

The length of the linker domain(s) 120 of the scaffold polypeptide 110 can be designed in order to specifically tailor or customize the spacing between cohesin domains 130. The length of the linker domain can therefore vary to suit one or more factors, such as recombinant target protein 140 size, desire for free motion of adjacent recombinant target proteins 140, flexibility of the recombinant polypeptide scaffold 110, and shuttling of substrate between enzymatic catalytic domains of the recombinant target proteins 140. According to some embodiments, linker domains 120, whether derived from a naturally occurring scaffoldin or synthetic, can range in length from 1 to about 800 residues. In certain embodiments, a linker domain can be from about 5 to about 10 amino acids in length. In other embodiments, a linker domain can be from about 20 to about 40 amino acids in length. In some embodiments, a linker domain can be from about 50 to about 100 amino acids in length. In yet other embodiments, a linker domain can be from about 100 to about 700 residues. Examples of linker domains suitable for use with scaffolds provided by the present disclosure are provided in Table 3.

TABLE 3

Representative linker domains.

| SEQ ID NO: | Amino Acid Sequence |
|---|---|
| 1 | TPTPTATPAPTVTPTPTPAPTPTPTPTPTATPTPTPTPTPTATP TVTATPTPTPSSTP |
| 2 | TNKPVIEG |
| 3 | GGGSGGGSEGGGSEGGGSEGGGSEGGGSEGGGSGGGS |
| 4 | TTVPTTSPTTTPPEPTITP |
| 5 | TTSTTTTTVTTTSTTTTTVT |
| 6 | GGGSGGGSEGGGS[EGGGS]$_n$EGGGSEGGGSEGGGSGGGS |

In SEQ ID NO: 6, repeating unit EGGGS (SEQ ID NO: 29) repeats n number of times, where n is an integer between 1 and 200.

In certain embodiments, there is no linker domain between two adjacent cohesin domains (e.g., 130A and 130B of FIG. 2). In such embodiments, the two cohesion domains are directly joined to one another.

In embodiments comprising two or more linker domains, each linker domain can be different both in terms of amino acid sequence and length, or the linkers or a subset thereof can be identical.

Recombinant Target Proteins

According to some embodiments, including those depicted in FIGS. 1 and 2, enzymatic polypeptide scaffolds 100 described herein comprise two or more recombinant target polypeptides 140, with each recombinant target polypeptide comprising a dockerin domain 150 and an enzymatic catalytic domain 160. In certain embodiments, each recombinant target protein is targeted to a specific cohesin 130 via its dockerin domain 150. Examples of dockerins and the respective cohesin binding partners that may be used in the enzymatic polypeptide scaffolds described herein are provided in Table 1. The recombinant target protein can comprise a full dockerin polypeptide, or a fragment thereof that is sufficient to bind with its target cohesin domain. In certain embodiments, a fragment of a full dockerin polypeptide binds to its cohesin partner with substantially the same affinity as the full dockerin polypeptide. As used herein, "dockerin domain" refers to a full dockerin polypeptide as well as a fragment of a full dockerin polypeptide capable of binding with its target cohesin domain.

According to some embodiments, the enzymatic catalytic domain 160 of a recombinant target protein 140 can be a full enzyme, or a domain or fragment thereof that retains the enzyme's catalytic activity. Thus, as used herein, the term "enzymatic catalytic domain" may refer to a full enzyme or a domain or fragment of a full enzyme that retains the enzyme's catalytic activity. It is contemplated that any enzyme or catalytic domain of any enzyme can be included in a recombinant target protein 140 as the enzymatic catalytic domain 160. The amino acid sequence of the enzyme or catalytic domain can be 90% to 100% identical to that of a known enzyme or catalytic domain thereof.

In some embodiments, the recombinant target polypeptide 140 is a recombinant fusion polypeptide comprising a dockerin domain 150 and an enzymatic catalytic domain 160. The dockerin domain 150 and the enzymatic catalytic domain 160 can be directly fused to one another, or can be interconnected via a fusion polypeptide linker.

The specificity of the interaction between cohesin domains 130 of the recombinant scaffold protein 110 and the dockerin domains 150 of the recombinant target polypeptides 140 allow for an ordered array of enzymatic activity along the enzymatic polypeptide scaffold 100. In certain embodiments, an ordered array of enzymatic activity, resulting from a particular order of recombinant target polypeptides, may form a metabolic pathway or part of a metabolic pathway. The identity of the enzymatic catalytic domains 160 of an enzymatic polypeptide scaffold 100 may thus be selected based on the desired use (i.e., metabolic pathway) of a particular enzymatic polypeptide scaffold 100. Many different metabolic pathways can be incorporated into an enzymatic polypeptide scaffold 100. Representative examples include conversion of glycerol to 3-hydroxypropionic acid (3-HP), conversion of glycerol to 1,3 propanediol (1,3 PDO), conversion of pyruvate to 2, 3 butanediol, conversion of acetyl-CoA to alkenes, and conversion of farsenyl pyrophosphate to nootkatone and gluconic acid. Enzymatic polypeptide scaffolds that comprise these metabolic pathways are described herein in the Examples section and in the drawings. While enzymatic polypeptide scaffolds having these metabolic activities are described in more detail herein, it is contemplated that other metabolic pathways can be similarly incorporated into enzymatic polypeptide scaffolds described herein. The guidance provided by the present description will allow one of skill in the art engineer enzymatic polypeptide scaffolds that comprise any metabolic pathway of interest. This can be accomplished by incorporating different combinations of recombinant target polypeptides having different enzymatic activities.

Acellular and In Vivo Use of Enzymatic Polypeptide Scaffolds

In various aspects, enzymatic polypeptide scaffolds described herein may be used in industrial processes, including for example, biodiesel, biochemical, and biopolymer production. In some embodiments, enzymatic polypeptide scaffolds may be employed in an acellular, or in vitro, manner. In some embodiments, enzymatic polypeptide scaffolds may be adapted to be expressed in a target organism and function in that organism.

Several factors negatively impact the production yield, and thus the cost of biofuels and biopolymers from renewable sources. Common hindrances in the biological production of materials and chemicals include (1) intermediate- and/or end-product toxicity to the microbial biocatalyst, (2) the diversion of carbon to biomass formation, and (3) co-production of undesired byproducts. One alternative is to eliminate the use of a microbial biocatalyst entirely and instead operate the desired metabolic pathway in isolation, thus circumventing the roadblock of biological toxicity and lack of specificity. However, in vitro enzyme systems typically suffer from low productivities owing in part to the effects of free diffusion of intermediates within metabolic pathways, lack of long term enzyme stability, cofactor cost, inefficient recycling rates, and cost of enzyme production.

The enzymatic polypeptide scaffolds described herein overcome the limitations of microbial biocatalysts. For example, the enzymatic polypeptide scaffolds can function acellularly, obviating any issues with intermediate- or end-product toxicity. In those embodiments in which the enzymatic polypeptide scaffold is expressed in a cell, the structure of the scaffold may help reduce or eliminated intermediate-product toxicity via shuttling of the intermediate product to the next enzyme. Due to the ordered nature and close proximity of the enzymatic catalytic domains of the recombinant target polypeptides, the intermediate will contact the next enzyme in the metabolic pathway with increased efficiency relative to either free enzyme or un-tethered intracellular enzymes. Overall, the enzymatic polypeptide scaffolds provide for increased efficiency by grouping the enzymes of the metabolic pathway together. In certain embodiments, cofactor recycling enzymes can be included in the enzymatic polypeptide scaffold, further increasing overall efficiency of the metabolic pathway tethered on the pathway.

Enzymatic Polypeptide Scaffold Modifications

Many modifications to the basic enzymatic polypeptide scaffold can be made to adapt the synthetic scaffold for a particular purpose or use in a particular process, or to, for example, optimize the enzymatic efficiency of the enzymatic polypeptide scaffold. In certain embodiments, the enzymatic polypeptide scaffolds can be engineered to bind to existing enzyme reactors or surfaces. This can allow for simple reactor design and product recovery.

Figure 3:
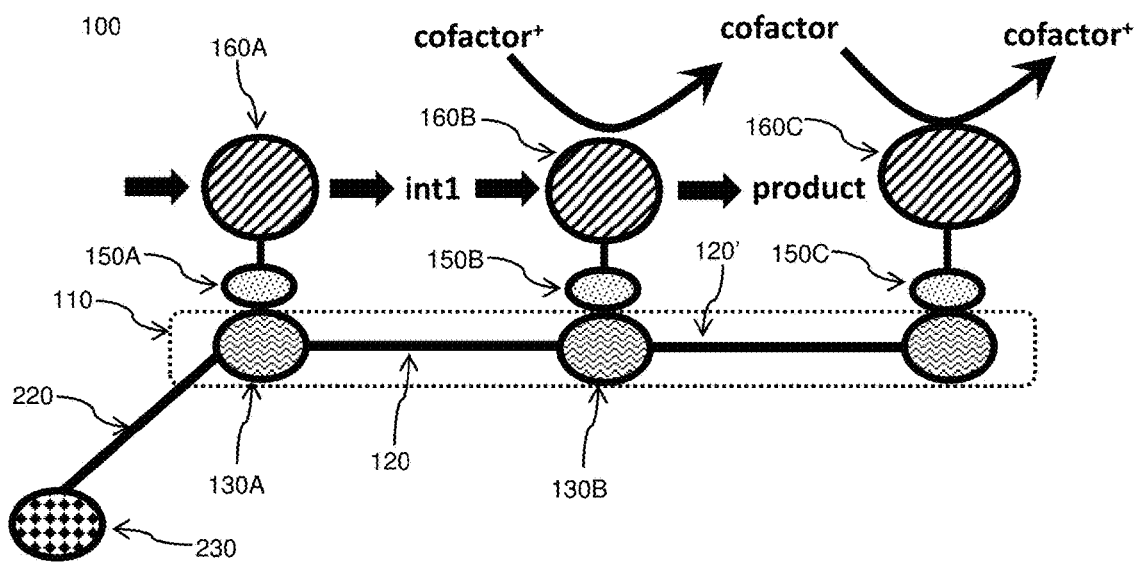
FIG. 3 is an illustration depicting the three-enzyme enzymatic polypeptide scaffold of FIG. 2 with the addition of a surface binding domain according to one embodiment.

According to some embodiments, an enzymatic polypeptide scaffold can also comprise a surface binding domain. Referring to FIG. 3, surface binding domain 230 can be linked to the enzymatic polypeptide scaffold 100 via a surface binding domain linker 220. In some embodiments, a surface binding domain 230 can be linked to one end of the enzymatic polypeptide 100, as depicted in FIG. 3, or to both ends of the enzymatic polypeptide scaffold 100. The surface binding domain linker can be, for example, a synthetic linker polypeptide disclosed herein.

In certain embodiments, the surface binding domain 230 can be selected to enable attachment of the enzymatic polypeptide scaffold 100 to a preferred substrate or surface, such as, for example, cellulose or a functionalized surface, such as an enzyme reactor.

Figure 4:
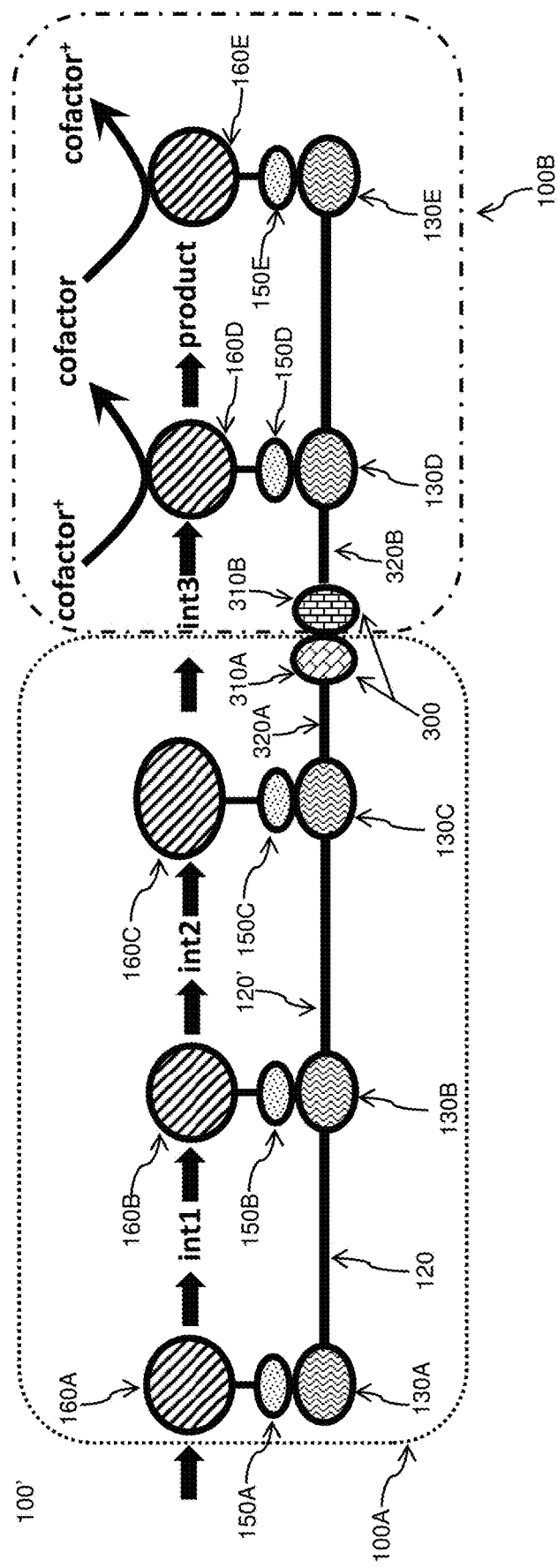
FIG. 4 is an illustration depicting a five-enzyme extended enzymatic polypeptide scaffold according to one embodiment.

In some embodiments, it may be desirable to link two separate enzymatic polypeptide scaffolds in order to facilitate formation of longer scaffolds and/or improve enzymatic polypeptide scaffold stability. In such embodiments, an extended enzymatic polypeptide scaffold can be formed by linking two separate enzymatic polypeptide scaffolds via an adapter cohesin/dockerin pair. FIG. 4 depicts an extended enzymatic polypeptide scaffold 100' that comprises a three-enzyme enzymatic polypeptide scaffold 100A and a two-enzyme enzymatic polypeptide scaffold 100B linked via adapter cohesin/dockerin pair 300. The result is the five-enzyme extended enzymatic polypeptide scaffold 100'. As described herein, in some embodiments, a recombinant scaffold polypeptide comprising multiple cohesin domains and linker domains can be expressed from a single construct. Where the recombinant scaffold polypeptide is to be lengthy and comprise many cohesin and linker domains, the recombinant scaffold polypeptide can be split into two or more constructs to improve expression efficiency. As depicted in FIG. 4, in some embodiments, a first recombinant scaffold polypeptide, enzyme polypeptide scaffold 100A, will comprise an adapter cohesin or dockerin domain 310A linked via adapter linker 320A, while a second recombinant scaffold polypeptide, enzyme polypeptide scaffold 100B, will comprise a binding partner 310B (linked to the second recombinant scaffold polypeptide via adapter linker 320B) for adapter cohesin or dockerin domain 310A. While in some embodiments, an extended enzymatic polypeptide scaffold may be directed to a single metabolic pathway, in other embodiments, an extended enzymatic polypeptide scaffold can be directed to two or more metabolic pathways, with the end product of one metabolic pathway being utilized as starting material for an adjacent metabolic pathway located on the same extended enzymatic polypeptide scaffold. The adapter linkers 320A and 320B can be, for example, a synthetic linker polypeptide disclosed herein.

Figure 5:
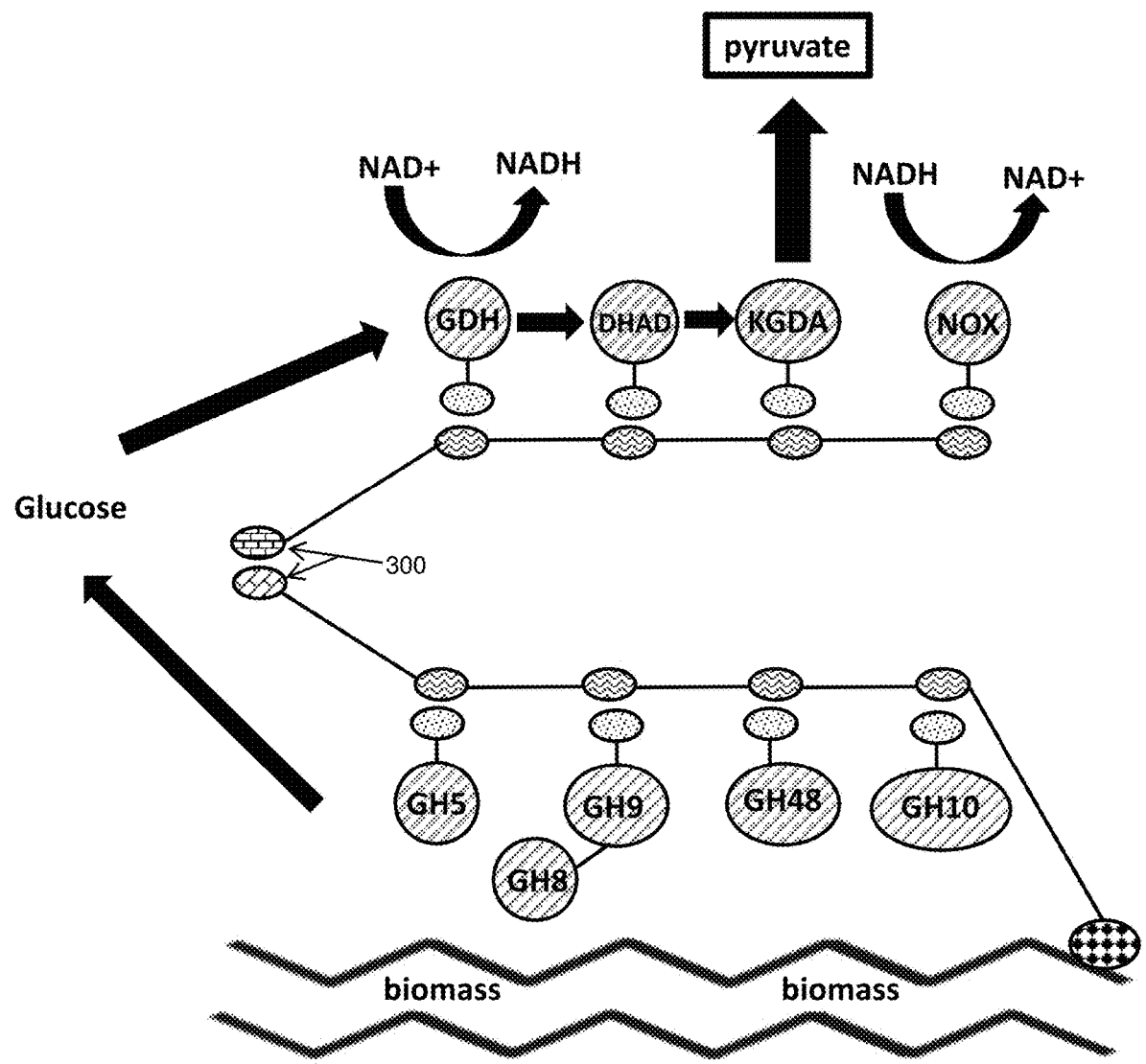
FIG. 5 is an illustration depicting an enzymatic polypeptide scaffold carrying a cellulose degradation pathway linked to an enzymatic polypeptide scaffold carrying glycolytic pathway via an adapter cohesin/dockerin pair according to one embodiment.

In other embodiments, the adapter cohesin/dockerin pair 300 can be adapted to link two enzymatic polypeptide scaffolds, as illustrated in FIG. 5. In the depicted embodiment, a first enzymatic polypeptide scaffold carrying a first metabolic pathway that degrades cellulose and produces glucose is linked to a second enzymatic polypeptide scaffold carrying a metabolic pathway that produces pyruvate from the glucose.

Figure 6:
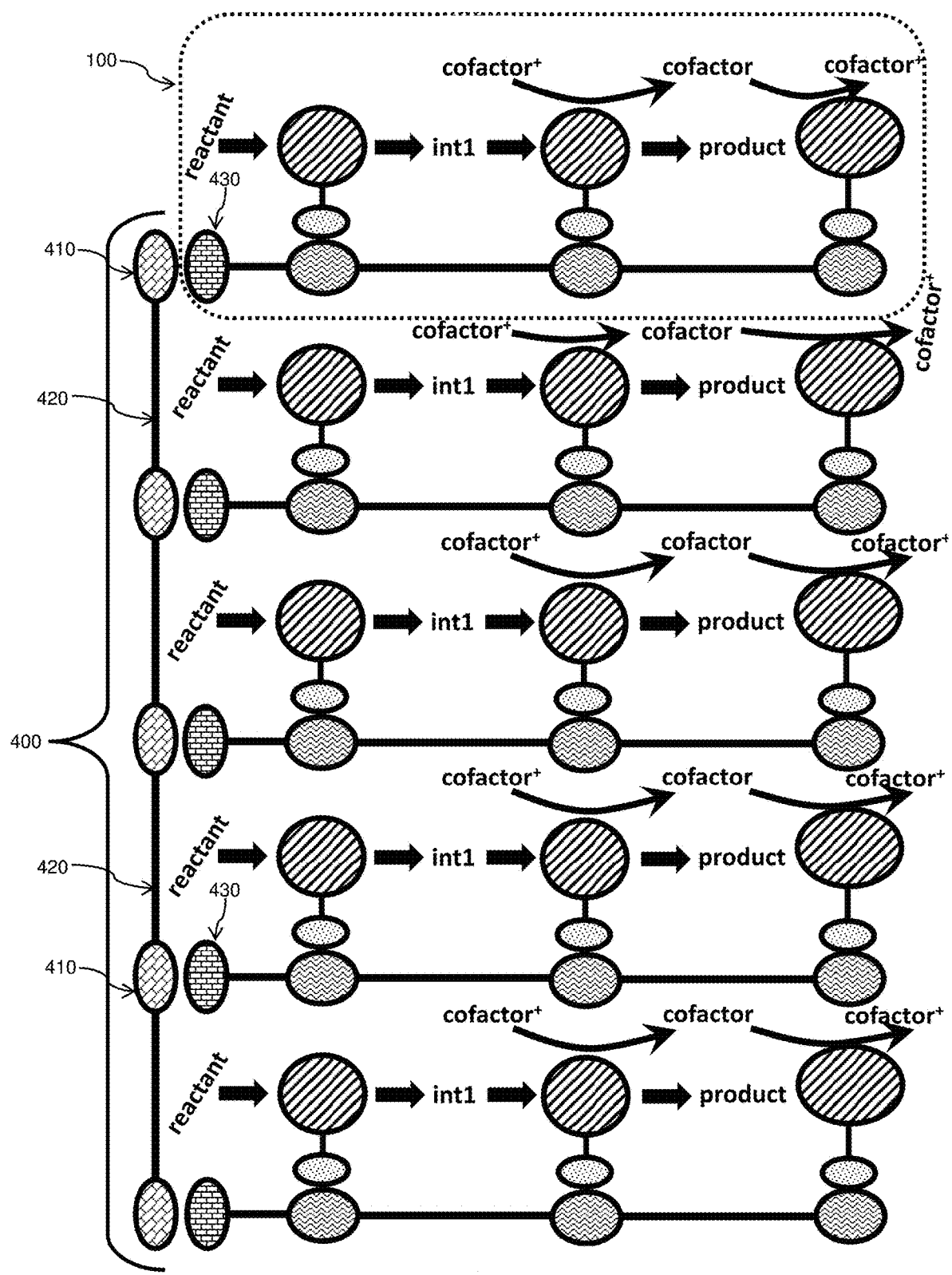
FIG. 6 is an illustration depicting multiple enzymatic polypeptide scaffolds grouped via an adapter scaffold according to one embodiment.

In yet other embodiments, an adapter scaffold can be used to spatially group two or more enzymatic polypeptide scaffolds. As depicted in FIG. 6, adapter scaffold 400 can group multiple enzymatic polypeptide scaffolds 100. In some embodiments, adapter scaffold 400 comprises two or more adapter scaffold cohesin domains 410 linked via at least one adapter scaffold linker polypeptide 420. The adapter scaffold linker 420 can be, for example, a synthetic linker polypeptide disclosed herein. In certain embodiments, the adapter scaffold 400 can group two or more identical enzymatic polypeptide scaffolds 100. In these embodiments, each of the adapter scaffold cohesin domains of the adapter scaffold 400 can be identical. Enzymatic polypeptide scaffolds 100 can each incorporate an adapter scaffold dockerin 430 selected to selectively bind the adapter scaffold cohesin domains 410. The spatial grouping of the enzymatic polypeptide scaffolds can further increase enzymatic efficiency relative to a single enzymatic polypeptide scaffold, as shuttling of pathway intermediates will be improved due to their increased spatial concentration.

Figure 7:
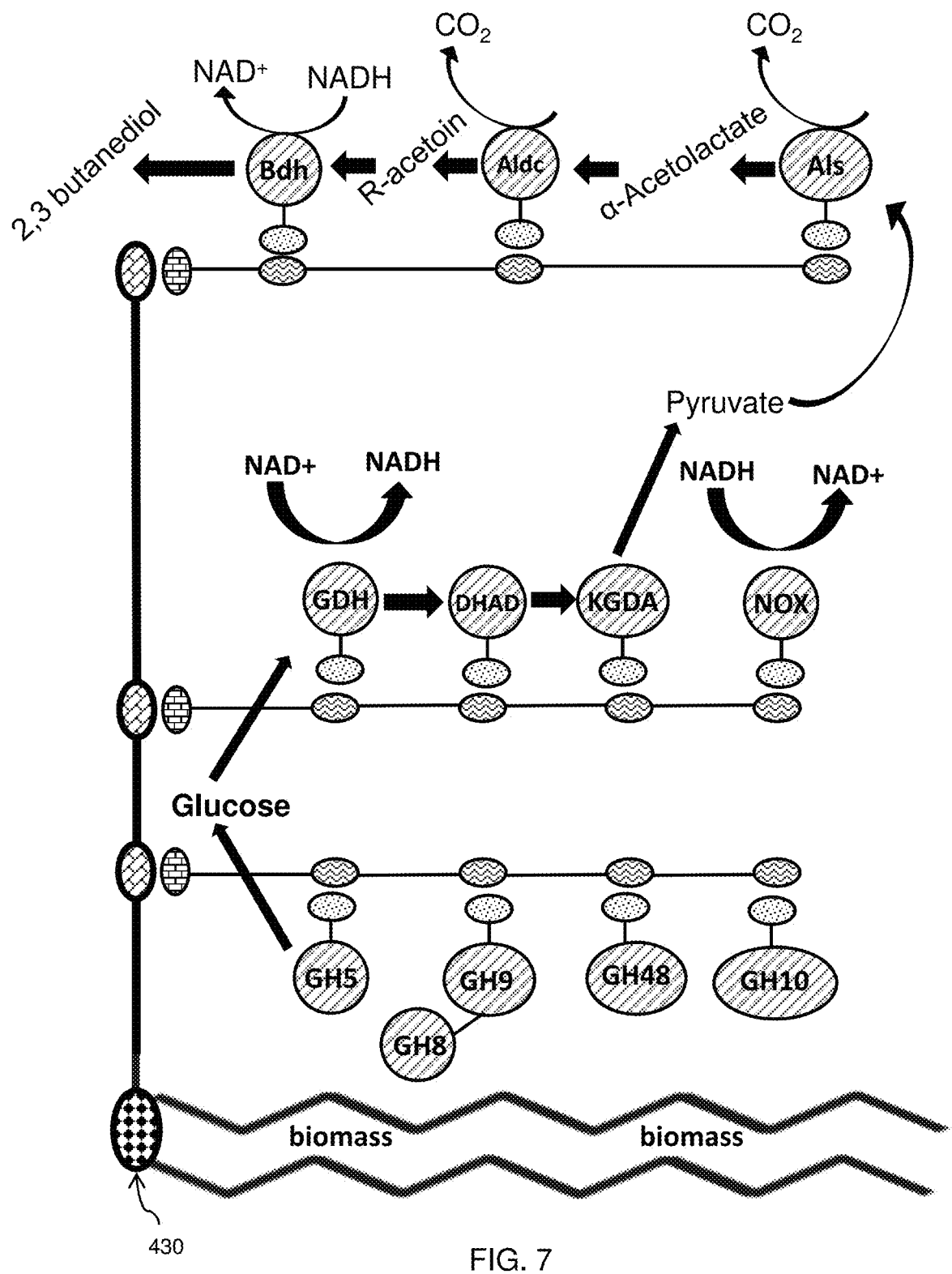
FIG. 7 is an illustration depicting a grouping of enzymatic polypeptide scaffolds carrying a cellulose degradation pathway, a glycolytic pathway, and a 2,3 butanediol synthesis pathway according to one embodiment.

In other embodiments, the enzymatic polypeptide scaffolds 100 can comprise different recombinant target polypeptides and be directed to different metabolic pathways. In such embodiments, the adapter scaffold can be designed similarly to the recombinant polypeptide scaffold and have two or more distinct cohesin domains 410. The enzymatic polypeptide scaffolds 100 to be grouped to the adapter scaffold 400 can each have a unique adapter scaffold dockerin domain 430 linked to it, where the adapter scaffold dockerin 430 for each different enzymatic polypeptide scaffold is selected to specifically bind to one of the distinct cohesin domains 410 of the adapter scaffold 400. Such an arrangement can allow for related metabolic pathways to be grouped together to improve overall enzymatic efficiency. For example, it may be desirable to group enzymatic polypeptide scaffolds that carry the enzymes for different metabolic pathways when the end-product of one metabolic pathway serves as the starting material for a second metabolic pathway. See, for example, FIG. 7, wherein a first metabolic pathway degrades cellulose and produces glucose, a second metabolic pathway produces pyruvate from the glucose, and a third metabolic pathway produces 2,3 butanediol from the pyruvate. In some embodiments, the adapter scaffold 400 can comprise a surface binding domain 430, as depicted in FIG. 7.

In particular embodiments, an adapter scaffold can be modified to optimize a particular metabolic pathway. For example, certain metabolic pathways are known to include a rate limiting component that dictates the overall rate of the pathway, such as the mevalonate pathway, in which 3-hydroxy-3-methylglutaryl-CoA reductase is the rate-limiting enzyme, the n-butanol synthesis pathway, in which 3-hydroxybutyryl-CoA dehydrogenase is the rate-limiting enzyme, or the β-alanine pathway for 3HP production, in which PanD is the rate-limiting enzyme. In the embodiment depicted in FIG. 8, several of the enzymatic polypeptide scaffolds comprise a single, rate-limiting enzyme. The central enzymatic polypeptide scaffold comprises the second enzyme of the metabolic pathway, and a cofactor recycling enzyme. In certain embodiments such an arrangement can improve overall enzymatic efficiency and end-product yields.

Recombinant Polynucleotide Constructs and Expression Vectors

"Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as nucleic acids containing modified bases.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

A nucleic acid molecule or polynucleotide can include a naturally occurring nucleic acid molecule that has been isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

A nucleic acid molecule is not required to encode a protein having protein activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

A "vector" or "recombinant vector" is a nucleic acid molecule that is used as a tool for manipulating a nucleic acid sequence of choice or for introducing such a nucleic acid sequence into a host cell. A vector may be suitable for use in cloning, sequencing, or otherwise manipulating one or more nucleic acid sequences of choice, such as by expressing or delivering the nucleic acid sequence(s) of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence. The phrase "operatively linked" refers to linking a nucleic acid molecule to an expression control sequence in a manner such that the molecule can be expressed when introduced (i.e., transformed, transduced, transfected, conjugated or conduced) into a host cell.

Vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, or termination of transcription. Suitable regulatory sequences include any sequence that can function in a host cell or organism into which the recombinant nucleic acid molecule is to be introduced, including those that control transcription initiation, such as promoter, enhancer, terminator, operator and repressor sequences. Additional regulatory sequences include translation regulatory sequences, origins of replication, and other regulatory sequences that are compatible with the recombinant cell. The expression vectors may contain elements that allow for constitutive expression or inducible expression of the protein or proteins of interest. Numerous inducible and constitutive expression systems are known in the art.

Typically, an expression vector includes at least one nucleic acid molecule of interest operatively linked to one or more expression control sequences (e.g., transcription control sequences or translation control sequences). In one aspect, an expression vector may comprise a nucleic acid encoding a recombinant target polypeptide 140, which is a recombinant fusion polypeptide comprising a dockerin domain 150 and an enzymatic catalytic domain 160, as described herein, operably linked to at least one regulatory sequence. It should be understood that the design of the expression vector may depend on such factors as the choice of the host cell to be transformed and/or the type of polypeptide to be expressed.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable expression vectors may include (or may be derived from) plasmid vectors that are well known in the art, such as those commonly available from commercial sources. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, yeast, and mammalian vectors, have been described for replication and/or expression in various host cells or cell-free systems, and may be used with the sequences described herein for simple cloning or protein expression.

Figure 9:
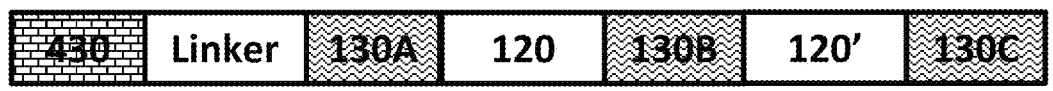
FIG. 9 is an illustration of representative polynucleotide constructs useful for generating a recombinant polypeptide scaffold of an enzymatic polypeptide scaffold according to one embodiment.
Figure 9:
Figure 9:
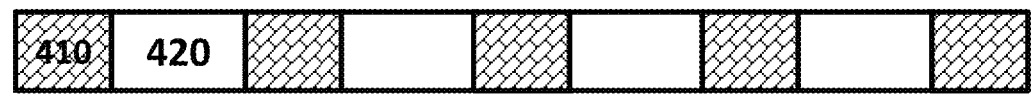

In certain embodiments, the elements of an enzymatic polypeptide scaffold and any additional elements required by a modification described herein (e.g., adapter scaffolds) can be encoded by a recombinant polynucleotide construct. In certain embodiments, separate recombinant polynucleotide constructs can be designed, with each separate polynucleotide construct encoding one element of an enzymatic polypeptide scaffold. For example, in some embodiments, separate recombinant polynucleotide constructs encode each of (1) the recombinant polypeptide scaffold, (2) the recombinant target polypeptides, and when present, (3) the adapter scaffold. Various examples of polynucleotide constructs are illustrated in FIG. 9. The constructs depicted in FIG. 9 illustrate constructs that can be used to express the recombinant polypeptide scaffold (top construct), recombinant target polypeptide (middle construct), and adapter scaffold (bottom construct) of FIG. 6. The numbers of FIG. 9 therefore correspond to the encoded polypeptides of FIG. 6.

Figure 10:
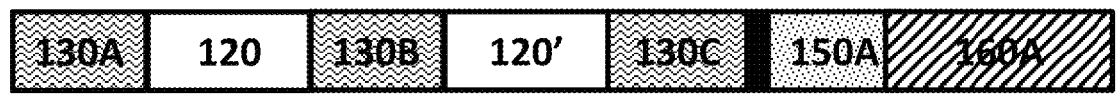
FIG. 10 is an illustration of representative polynucleotide constructs useful for generating a recombinant target polypeptide of an enzymatic polypeptide scaffold according to one embodiment.

In other embodiments, multiple elements of the enzymatic polypeptide scaffold, such as the recombinant polypeptide scaffold and the recombinant target polypeptides, can be encoded by a single polynucleotide construct. Examples of polynucleotide constructs encoding multiple elements of the enzymatic polypeptide scaffold are illustrated in FIG. 10. The construct depicted in FIG. 10 illustrates a construct that can be used to express the enzymatic polypeptide scaffold of FIG. 2. The numbers of FIG. 10 therefore correspond to the encoded polypeptides of FIG. 2.

According to some embodiments, polynucleotide constructs encoding an enzymatic polypeptide or an element of an enzymatic polypeptide can be included in an expression vector. In certain embodiments, the expression vector may comprise one or more restriction enzyme sites adjacent to, for example, those polynucleotide sequences encoding the enzymatic catalytic domains of the recombinant target proteins. This can allow for the easy swapping of one enzyme for another, or for a complete change in enzymatic catalytic domains. The result of this latter approach is the re-use of the recombinant polypeptide scaffold and associated dockerin domains. By exchanging the enzymatic catalytic domains, a new metabolic pathway can be established on the scaffold.

In some embodiments the expression vector is selected for expression in a standard expression host, such as *E. coli*. In other embodiments, the expression vector is selected for expression in a microorganism used in industrial applications, such as, for example, *S. cerevisiae*.

Methods for generating recombinant polynucleotide constructs and their incorporation into appropriate expression vectors are well known in the art, as are methods for protein expression and purification.

Enzymatic Polypeptide Scaffold Optimization

In certain embodiments, the various components of an enzymatic scaffold can be optimized to maximize enzymatic efficiency. In some embodiments, the enzymatic catalytic domains of the recombinant target polypeptides can be replaced with a homologous enzymatic catalytic domain. The homologous enzymatic catalytic domain can be from another species, or can be a mutant of the original enzymatic catalytic domain having increased or improved enzyme activity. In this regard, in some embodiments, the enzymatic polypeptide scaffolds provide a platform for screening enzymes and identifying suitable combinations of enzymes in a heterologous metabolic pathway. Metabolic pathway engineering is often done on a trial and error basis, sometimes without a detailed understanding of the pathway, the channeling of the intermediates, exchange or recycling of cofactors, stability of the enzymes, interaction and compatibility of the enzymes selected from different heterologous hosts, and/or the kinetics of the overall pathway. Testing these pathways in vitro prior to cloning is possible but cumbersome. All enzymes have to be processed from expression, purification, and characterization to ensure proper stoichiometry of the enzyme mixture. These enzymes, natively intracellular, can also suffer from poor stability outside of the cell and may not behave as they would within a microorganism. The enzymatic polypeptide scaffolds can reduce, and even eliminate, these problems, and can serve as a platform for the study of enzyme interaction and metabolic pathway kinetics.

In addition to the enzymatic catalytic domain, overall design of the recombinant target polypeptides can be optimized by modifying the interaction between the enzymatic catalytic domain and the dockerin domain. In some embodiments, the dockerin domain can be linked to the N-terminus or to the C-terminus of the enzymatic catalytic domain. Linkage of the dockerin domain to one end of the enzymatic catalytic domain may adversely affect enzymatic activity by, for example, steric hindrance. If linkage at either end is found to affect enzymatic activity, a recombinant polypeptide linker can be included between the dockerin domain and the enzymatic catalytic domain. Such linkers are well known in the art, and are regularly included in fusion polypeptides such as the recombinant target polypeptides.

In some embodiments, the arrangement of cohesin domains along the recombinant polypeptide scaffold can also be adjusted to ensure optimal spacing of the bound recombinant target polypeptides and their enzymatic catalytic domains. This can be achieved by altering the length of the recombinant polypeptide scaffold's linker domains to adjust the distance between the cohesin domains. In certain embodiments, it may be desirable to have variable spacing between the cohesin domains, with some being closer together than others.

Methods of Use

In certain embodiments, an enzymatic polypeptide scaffold can be used in a bioreactor setting to catalyze the conversion of starting material to an end product. For example, glycerol can be converted to 3-hydroxypropionic acid (3-HP) and/or 1,3-propanediol (1,3 propanediol), pyruvate can be converted to 2, 3 butanediol, acetyl-CoA can be converted to alkenes, and farsenyl pyrophosphate can be converted to nootkatone and gluconic acid. In some embodiments, a starting material is provided in a bioreactor comprising the enzymatic polypeptide scaffolds. In other embodiments, starting materials are produced directly in the bioreactor. This can be done by fermentation by, for example, industrial microorganisms, free enzymes, or both. In yet other embodiments, a bioreactor can comprise enzymatic polypeptide scaffolds having different enzymatic activity, where certain enzymatic polypeptide scaffolds carry the enzymatic activity necessary to provide the starting material for the enzymatic polypeptide scaffold that generates the end product. In some embodiments, enzymatic polypeptide scaffolds are anchored within the bioreactor via a surface binding domain. In other embodiments, the enzymatic polypeptide scaffolds are not anchored to any surface and are distributed freely throughout the bioreactor. According to these and other embodiments, the bioreactor can be any bioreactor known in the art.

According to some embodiments, the recombinant target polypeptides can be expressed by cells in the bioreactor. When the cells are lysed, the recombinant target proteins can self-assemble on recombinant scaffold polypeptides present in the bioreactor, either tethered to a surface, or free, to produce the enzymatic polypeptide scaffold (see, e.g., FIG. 18). In certain embodiments, the same cells that express the recombinant target polypeptides may also contribute to the production of the starting material for the metabolic pathway of the enzymatic polypeptide scaffold (see, e.g., FIG. 18).

According to yet other embodiments, enzymatic polypeptide scaffolds can be used to study metabolic pathways and individual enzymes. Furthermore, by replacing the enzymatic catalytic domains of the recombinant target proteins, the enzymes of the enzymatic polypeptide scaffolds can be easily replaced, allowing for the rapid screening of enzymes for the best combination of enzymes within a heterologous metabolic pathway.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this disclosure, and without departing from the spirit and scope thereof, can make various changes and modifications to the subject matter provided by this disclosure to adapt it to various usages and conditions.

Example 1—Assembly of a Two-Protein Polypeptide Scaffold

Figure 11:
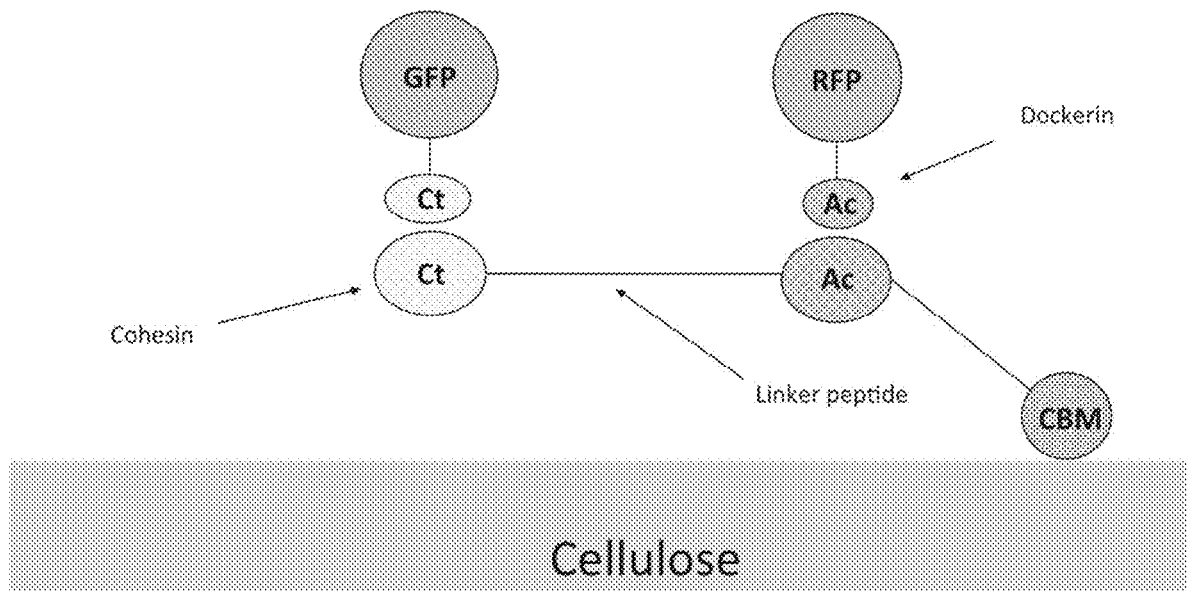
FIG. 11 is an illustration of an embodiment of a polypeptide scaffold comprising green fluorescent protein and red fluorescent protein.
Figure 12:
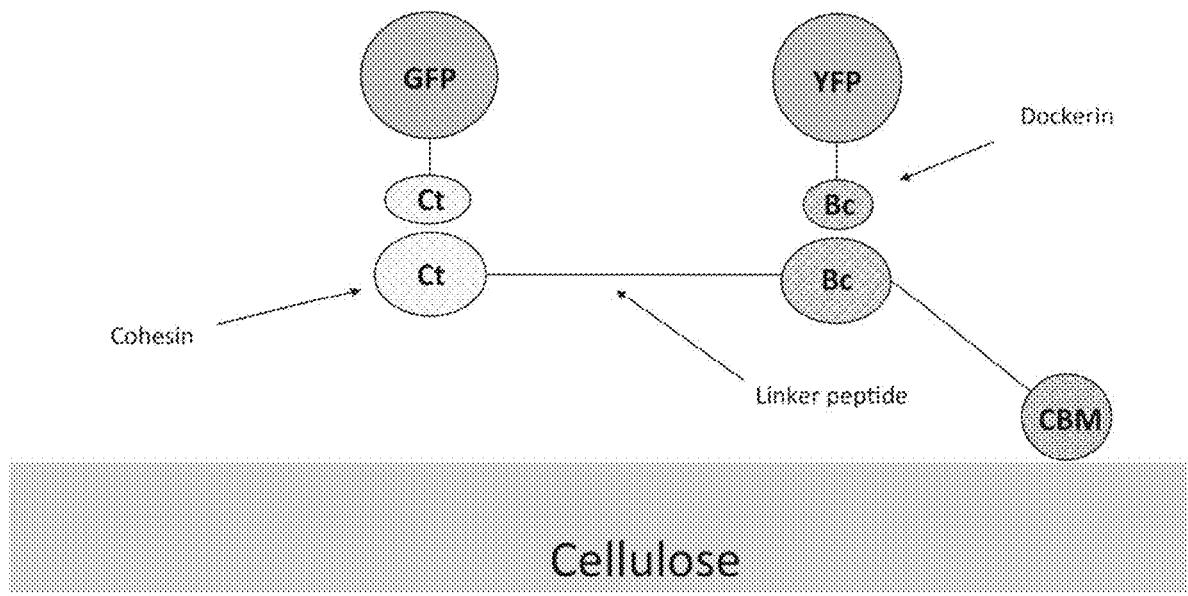
FIG. 12 is an illustration of an embodiment of a polypeptide scaffold comprising green fluorescent protein and yellow fluorescent protein.

Two-protein polypeptide scaffolds comprising either green fluorescent protein (GFP) and red fluorescent protein (RFP), or GFP and yellow fluorescent protein (YFP) were constructed. The fluorescent proteins were selected for their expression levels and to reduce overlap in their excitation wavelengths to allow selective image analysis. The best fluorescent protein candidates for this purpose were GFP, RFP, and YFP. After expression and purification of these components, the fully populated synthetic proteome was constructed by mixing the fusion proteins and synthetic scaffolds at the correct molar ratio. The GFP-RFP and GFP-YFP two-protein polypeptide scaffolds are illustrated in FIGS. 11 and 12, respectively.

Each recombinant scaffold polypeptide comprised two cohesin domains interconnected via a linker domain. An N-terminal surface anchor domain was also included, where the surface anchor domain bound cellulose. To produce the GFP-RFP polypeptide scaffold, recombinant target proteins comprising a dockerin domain and either a GFP domain or an RFP domain were generated. The dockerin domain of each recombinant target protein was selected to selectively bind to only one of the cohesin domains of the recombinant scaffold polypeptide. Similarly, to produce the GFP-YFP polypeptide scaffold, the RFP domain of the RFP recombinant target polypeptide was replaced with a YFP domain.

To produce the recombinant scaffold polypeptide for the GFP-RFP scaffold (SEQ ID NO: 37), the N-terminal surface anchor domain was first cloned into the pET6xHN-N vector. The cellulose binding domain (CBM) from *C. thermocellum* (ATCC 27405) scaffoldin CipA was selected as the N-terminal surface anchor domain. It was PCR amplified from the bacteria using primers engineered with restriction sites compatible with the multiple cloning site of the pET6xHN-N vector. The His-tag sequence of the vector was oriented on the 5' end of the CBM sequence by cloning the CBM sequence between the StuI and SalI sites. The remaining restriction sites were subsequently used for inserting linker domains and cohesin domains.

A PTPTPTP-type (SEQ ID NO: 39) linker was used as the linker domain. The first linker domain sequence was cloned into the pET6xHN-N vector already having the His-tag CBM sequence. The Ac-ScaC cohesin sequence was then PCR amplified from *A. cellulolyticus* (e.g., ATCC 33288) using primers engineered with appropriate restriction sites for use with the pET6xHN-N vector multiple cloning site. The cohesin domain was PCR amplified sequence and cloned into the vector at the 3' end of the PTPTPTP-type linker sequence. A second PTPTPTP-type linker sequence was then cloned into the vector at the 3' end of the Ac-ScaC cohesin sequence. The Ct-Sdba cohesin domain was then PCR amplified from *C. thermocellum* (ATCC 27405) using primers engineered with appropriate restriction sites for use with the pET6xHN-N vector multiple cloning site and cloned into the vector at the 3' end of the second linker sequence.

The resulting recombinant polynucleotide construct comprised the following (5' to 3'): His-tagged CBM polynucleotide sequence; a first linker domain polynucleotide sequence; a first cohesin domain polynucleotide sequence; a second linker domain polynucleotide sequence; and a second cohesin domain polynucleotide sequence (SEQ ID NO: 37).

The GFP-dockerin recombinant target polypeptide (SEQ ID NO: 34) was made by cloning the GFP and dockerin domain polynucleotide sequences into a bacterial expression vector. The GFP polynucleotide sequence was cloned into the same translational frame as the dockerin domain polynucleotide sequence, creating a continuous GFP-dockerin recombinant polynucleotide construct that could be translated into a GFP-dockerin recombinant target polypeptide. The dockerin domain polynucleotide sequence was cloned onto the 3' end of the GFP polynucleotide sequence in the pET6xHN-N expression vector. This vector contained a His-tag sequence and enterokinase cleavage site adjacent to the multiple cloning site, which was used to attach a His-purification tag to the N-terminus of the GFP protein. The tag was removed following protein purification. The vector also comprised a T7 promoter with the lac operator, allowing for IPTG-inducible expression.

The GFP polynucleotide sequence was obtained from the pET6xHN-GFPuv vector. The GFP cDNA was PCR amplified using primers engineered with restriction sites compatible with the multiple cloning site of the pET6xHN-N vector. The PCR amplified GFP polynucleotide sequence was then cloned into the multiple cloning site of the pET6xHN-N vector.

The dockerin domain polynucleotide sequence was obtained from *C. thermocellum*. The dockerin sequence was PCR amplified from the bacterial genomic DNA using primers engineered with appropriate restriction sites. The resulting PCR product was then cloned into the pET6xHN-N vector containing the GFP polynucleotide sequence. The dockerin domain polynucleotide sequence was inserted at the 3' end of the GFP sequence with a continuous reading frame useful for expression of the GFP-dockerin recombinant target polypeptide.

The RFP-dockerin recombinant target polypeptide (SEQ ID NO: 35) was made by cloning the RFP and dockerin domain polynucleotide sequences into the pET6xHN-N expression vector in a similar manner to the RFP-dockerin recombinant target polypeptide. The RFP polynucleotide sequence was obtained from the pHcRed. The RFP polynucleotide sequence was PCR amplified from the vector using primers engineered with restriction sites compatible with the multiple cloning site of the pET6xHN-N vector. The PCR amplified RFP sequence as then cloned into the multiple cloning site of the pET6xHN-N vector. The dockerin domain polynucleotide sequence was obtained from the genomic DNA of *A. cellulolyticus*. The dockerin sequence was PCR amplified from the bacterial genomic DNA using primers engineered with appropriate restriction sites. The resulting PCR product was then cloned into the pET6xHN-N vector containing the RFP polynucleotide sequence. The dockerin domain polypeptide sequence was inserted at the 3' end of the RFP polynucleotide sequence with a continuous reading frame useful for expression of the GFP-dockerin fusion protein.

Each of the expression vectors described was transformed into E. coli. Resulting colonies were picked for overnight incubation in LB/amp cultures at 37° C. until an O.D. of 0.6-0.8 was reached. IPTG was added to a concentration of 1 mM. The cultures were further incubated for an additional 4-5 hours. The induced bacterial cultures were then centrifuged to form a large bacterial pellet. The supernatant was decanted and the pellet of induced bacteria was frozen for later use. Affinity purification was used to purify the induced recombinant polypeptide under native conditions.

The customized synthetic proteome was assembled by sequentially adding the recombinant polypeptides to a cellulose-coated glass slide. The recombinant polypeptide scaffold comprising the CBM domain (surface anchor domain), cohesin domains and linker domain was deposited as a small drop on the surface of the cellulose-coated glass slide. Serial dilutions of the CBM-linker-cohesin scaffold were sequentially deposited in separate drops and subsequently washed. Next, both the GFP-dockerin and RFP-dockerin recombinant target polypeptides were washed over the glass slide, contacting each region where CBM-linker-cohesin recombinant polypeptide scaffold is deposited. The slides were then washed and mounted with coverslips for inspection via multi-wavelength confocal microscopy. Visualization of deposited regions at the GFP and RFP emission frequencies revealed co-localization of the fluorescent polypeptides, indicating proper assembly of the two-protein polypeptide scaffold.

The GFP-YFP two-protein polypeptide scaffold (SEQ ID NO: 38) was generated and prepared in a similar manner to the GFP-RFP two-protein polypeptide scaffold, but used a cohesin/dockerin pair from B. cellulosolvens in place of that from A. cellulolyticus. The YFP-dockerin recombinant target polypeptide (SEQ ID NO: 36) thus comprised a B. cellulosolvens dockerin domain.

Figures 13A, 13B:
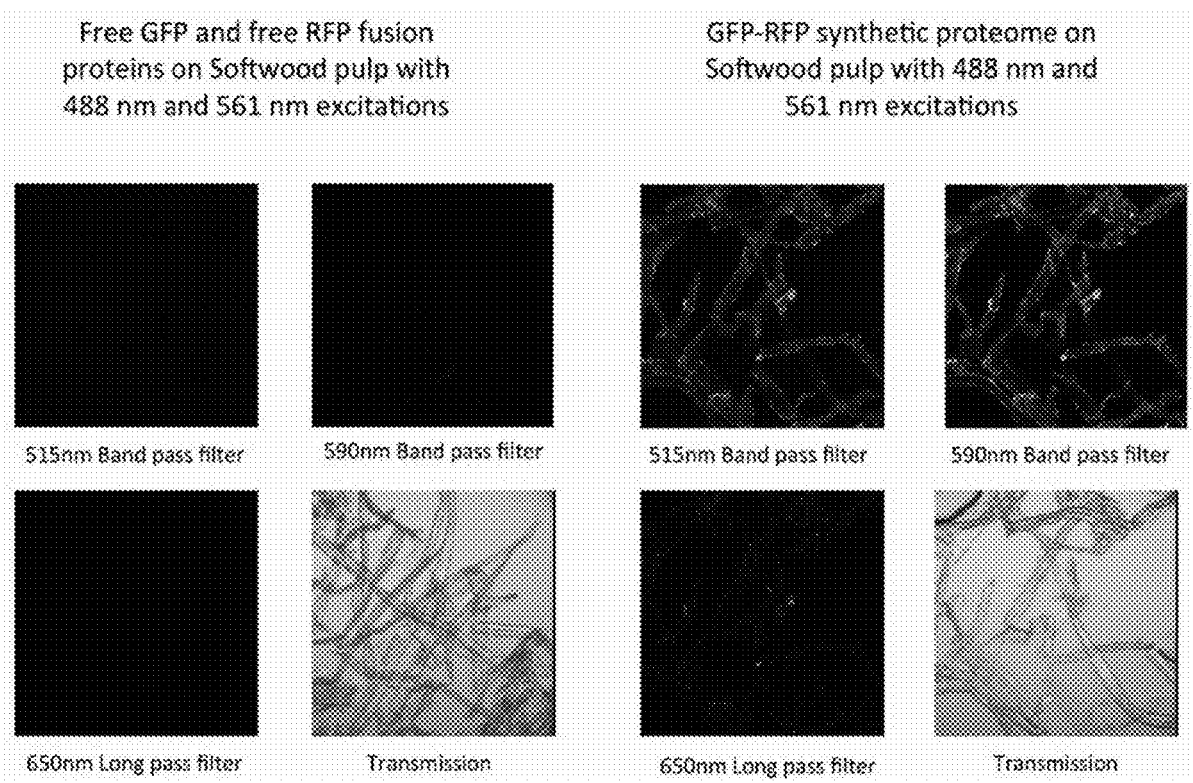
FIG. 13A is a series of photographs representing the lack of binding of free GFP and RFP to softwood pulp (488 nm and 561 nm excitation).
FIG. 13B is a series of photographs representing the binding of polypeptide scaffolds comprising GFP and RFP to softwood pulp (488 nm and 561 nm excitation).
Figures 14A, 14B:
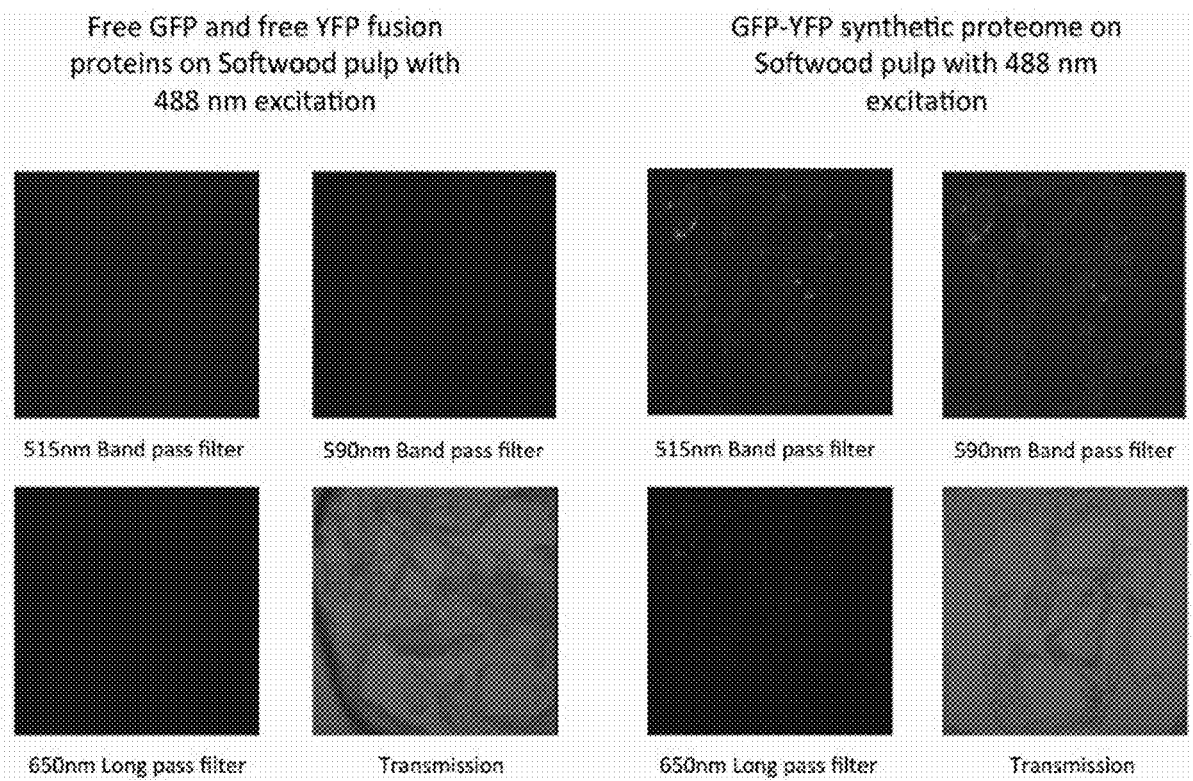
FIG. 14A is a series of photographs representing the lack of binding of free GFP and YFP to softwood pulp (488 nm excitation).
FIG. 14B is a series of photographs representing the binding of polypeptide scaffolds comprising GFP and YFP to softwood pulp (488 nm excitation).
Figures 15A, 15B:
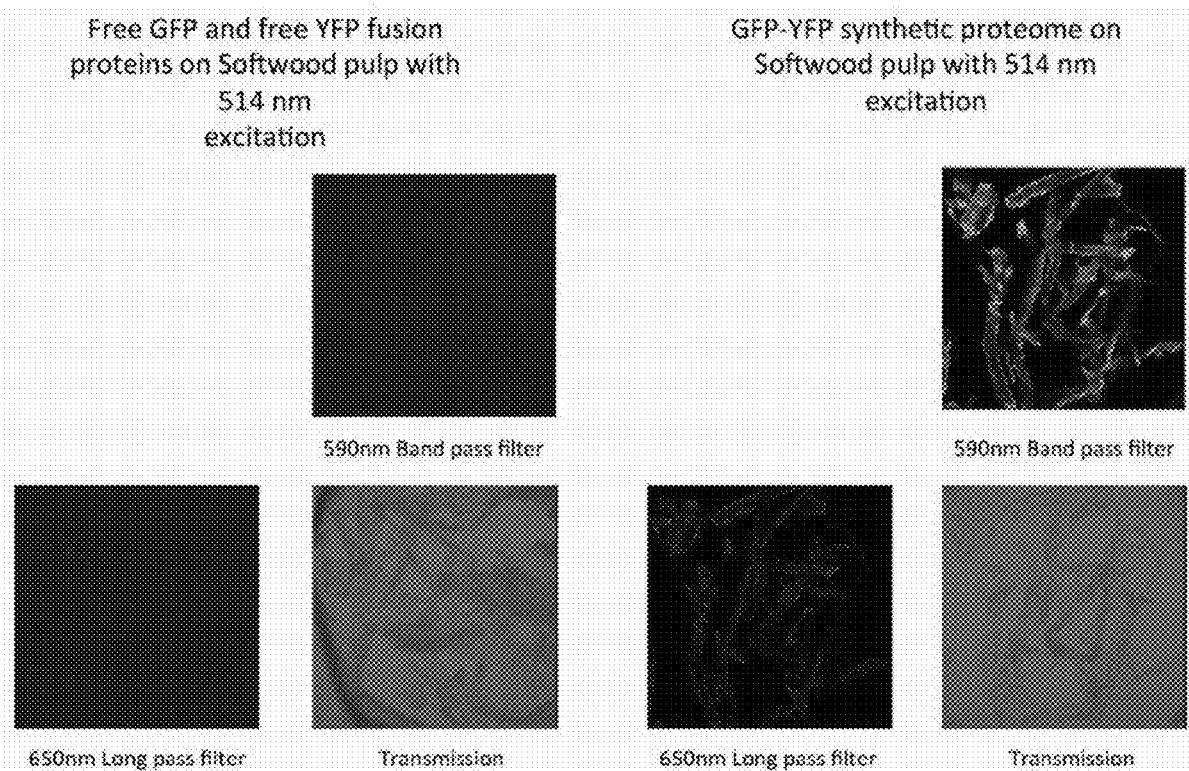
FIG. 15A is a series of photographs representing the lack of binding of free GFP and YFP to softwood pulp (514 nm excitation).
FIG. 15B is a series of photographs representing the binding of polypeptide scaffolds comprising GFP and YFP to softwood pulp (514 nm excitation).
Figure 16:
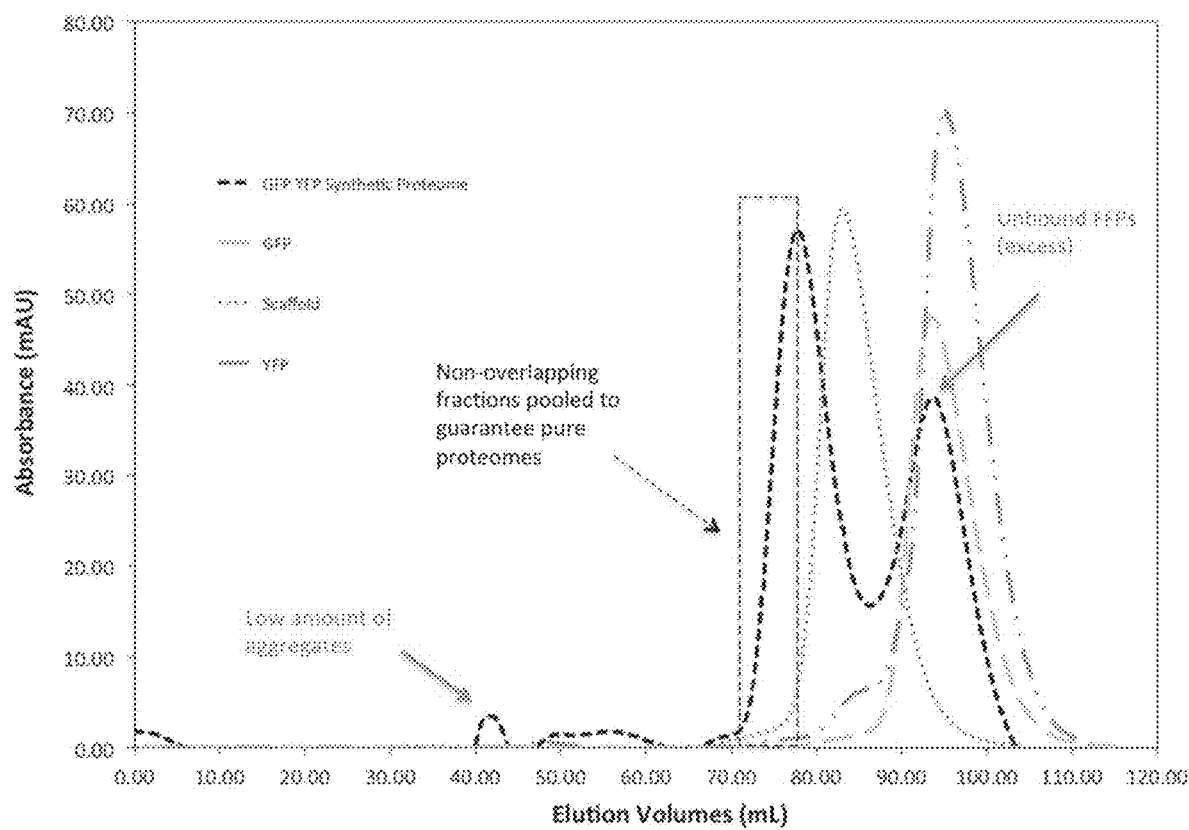
FIG. 16 is an absorbance spectrum illustrating absorbance of various elution fractions.

All recombinant polypeptides were found to be stable after purification. The excitation energies of the fluorescent polypeptides correlated well with published values both for free fusion fluorescent proteins (FFFPs) and when tethered to the polypeptide scaffolds. The tethering of the fluorescent polypeptides to the scaffold did not appear to impact the level of fluorescence detected. The polypeptide scaffolds and FFFPs were excited at 488 nm (GFP), 514 nm (YFP), or 561 nm (RFP), which were the closest wavelengths available in the system used. The resulting fluorescence was detected using a 515 nm (GFP, YFP), 590 nm (YFP, RFP), and 650 nm (RFP) filter. Results depicted in FIGS. 13-16 indicated that the fluorescent proteins only bound to cellulose when they were tethered to the scaffolds. There was no residual fluorescence detected on softwood pulp that would indicate non-specific binding of the FFFPs to the biomass (see, e.g., FIGS. 13A, 14A, and 15A). The data indicate that it is possible to produce recombinant target polypeptides bearing dockerin domains and tether them to a specific polypeptide scaffold without losing activity of the recombinant target polypeptide's fluorescent activity or modifying the fluorescent protein's behaviors.

Example 2—Enzymatic Polypeptide Scaffold for 3-Hp Production and Methods of Use

An enzymatic polypeptide scaffold capable of generating 3-hydroxypropionic acid (3-HP) from glycerol can be generated according to embodiments described herein. 3-HP has been identified as a top target chemical that can be produced from biomass due to the versatility of 3-HP as a chemical building block. 3-hydroxypropionic acid (3-HP) is a three carbon carboxylic acid that is a platform chemical for the production of many commercially important compounds. 3-HP can be converted into high value chemicals and biodegradable polymers such as acrylic acid, acrylamide, acrylonitrile, methyl acrylate, and malonic acid. These chemicals may in turn be used in a range of products, including paints, adhesives, plastics and the like.

Though 3-HP is an important intermediate for the production of biopolymers, biological production has not yet been well established. The biologically toxic nature of 3-HP and the metabolic intermediate 3-hydroxypropioaldehyde creates an obstacle for its production by an organism. Specifically, 3-hydroxypropioaldehyde is used as an antimicrobial agent, making the biological accumulation of 3-hydroxypropionic acid in an organism challenging. Implementing a cell-free enzyme system for the three-step (including one for cofactor regeneration) enzymatic pathway from glycerol to 3-HP can overcome these toxicity issues.

3-HP can be synthesized from intermediates such as glycerol, lactate, malonyl-CoA or β-alanine. Glycerol is a by-product of biodiesel production, and the availability of glycerol as an inexpensive source of carbon has increased commensurately with the rapid growth of the biodiesel industry. Glycerol thus represents an attractive feedstock for the production of 3-HP.

Figure 17A:
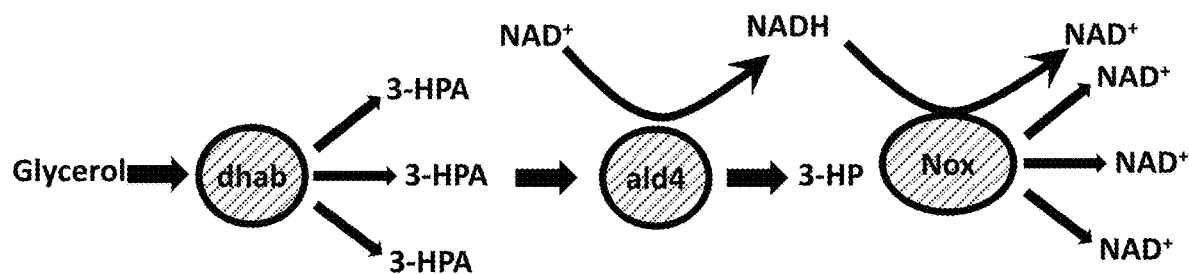
FIG. 17A is an illustration of a free-enzyme metabolic pathway for the synthesis of 3-hydroxypropionic acid from glycerol according to one embodiment.
Figure 17B:
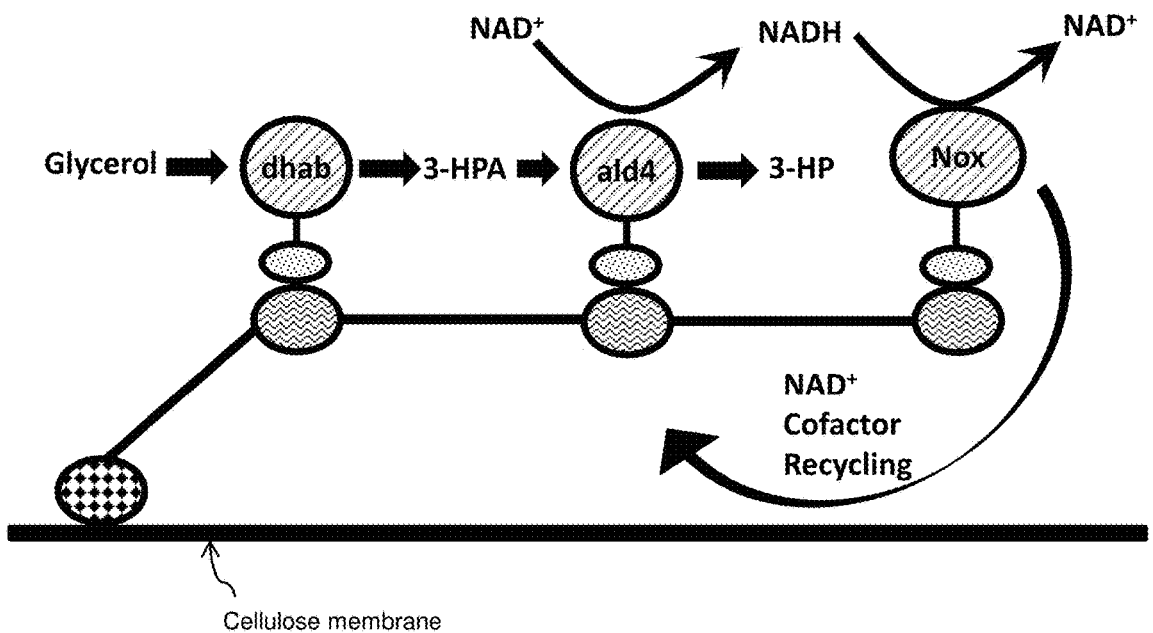
FIG. 17B is an illustration of an enzymatic polypeptide scaffold carrying a 3-hydroxypropionic acid synthesis pathway that is tethered to a cellulose membrane according to one embodiment.

FIG. 17A illustrates the basic metabolic pathway from glycerol to 3-HP. The three-enzyme pathway includes a glycerol dehydrogenase (e.g., dhaB), an aldehyde dehydrogenase (e.g., ald4), and a NADH oxidase (e.g., Nox) to recycle NADH. FIG. 17B illustrates an enzymatic polypeptide scaffold that incorporates and tethers these three enzymes. The entire enzyme or only a portion of the enzyme having catalytic activity may be included. dhaB and ald4 from Klebsiella pneumoniae (SEQ ID NOS: 8 and 9, respectively), and Nox from Lactococcus lactis (SEQ ID NO: 10) can be included in enzymatic polypeptide scaffold, although homologous enzymes from other organisms may be similarly used. The NADH oxidase can optionally be omitted.

A recombinant scaffold polypeptide can be used to arrange three recombinant metabolic, which can result in the efficient production of 3-HP. The recombinant scaffold polypeptide can comprise three unique cohesin domains, each capable of selectively binding a specific dockerin domain. The recombinant scaffold polypeptide can comprise linker and cohesin domains obtained from various species, or synthetic linker domains, and can be optimized by varying the length of the linker domain. The recombinant scaffold polypeptide can also comprise a surface anchor domain capable of anchoring the scaffold polypeptide to a substrate.

Cohesin/dockerin pairs to be used in the recombinant scaffold polypeptide and the recombinant can be selected from known binding pairs. Examples of cohesin/dockerin binding pairs suitable for use with such a scaffold are provided in Table 4, along with reference to their encoded amino acid sequences.

TABLE 4

Representative cohesin/dockerin pairs and corresponding amino acid sequences.

| Organism | Dockerin | Amino Acid Sequence (SEQ ID NO) | Compatible Cohesin | Amino Acid Sequence (SEQ ID NO) |
|---|---|---|---|---|
| *Acetivibrio cellulolyticus* | Doc ScaB | SEQ ID NO: 12 | Coh ScaC | SEQ ID NO: 11 |
| *Clostridium cellulolyticum* | Doc EndA | SEQ ID NO: 14 | Coh CipC | SEQ ID NO: 13 |
| *Bacteroides cellulosolvens* | Doc ScaA | SEQ ID NO: 16 | Coh ScaB | SEQ ID NO: 15 |
| *Clostridium thermocellum* | Doc 48S | SEQ ID NO: 18 | Coh CipA | SEQ ID NO: 17 |
| *Ruminococcus flavefaciens* | Doc ScaA | SEQ ID NO: 20 | Coh ScaB | SEQ ID NO: 19 |

The optional surface anchor domain is first cloned into the pET6xHN-N expression vector. The cellulose binding domain (CBM) from *C. thermocellum* (ATCC 27405) scaffoldin CipA can be selected as the N-terminal surface anchor, and may be PCR amplified from the bacteria using primers engineered with restriction sites compatible with the multiple cloning site of the pET6xHN-N vector. The His-tag sequence of the vector can be oriented on the 5' end of the CBM sequence by cloning the CBM sequence between the StuI and SalI sites of the vector. The remaining restriction sites can subsequently be used for inserting linker and cohesin domains.

The polynucleotide sequence from Z-EGFR-1907_SEG-Linker (Registry of Standard Biological Parts, BBa_K404306) can be used as the source for the linker sequences. The SEG-Linker sequence can be PCR amplified with primers engineered with appropriate restriction sites for use with the pET6xHN-N vector multiple cloning site. The SEG-Linker sequence encodes the amino acid sequence GGGSGGGSEGGGSEGGGSEGGGSEGGGSEGGGS-GGGS (SEQ ID NO: 7), and could be used as a repeating unit. The first linker peptide sequence can be cloned into the pET6xHN-N already having the CBM polynucleotide sequence. Next, the Ct-CipA cohesin domain polynucleotide sequence encoding the amino acid sequence represented by SEQ ID NO: 17 can be PCR amplified from *C. thermocellum* (ATCC 27405) using primers engineered with appropriate restriction sites for use with the pET6xHN-N vector multiple cloning site. The PCR amplified sequence can be cloned onto the 3' end of the SEG-Linker sequence. A second SEG-Linker sequence can be cloned onto the 3' end of the Ct-CipA cohesin sequence. A second cohesin domain polynucleotide sequence encoding Cc-CipC having the amino acid sequence represented by SEQ ID NO: 13 can be PCR amplified from *C. cellulolyticum* (ATCC 35319) using primers engineered with appropriate restriction sites for use with the pET6xHN-N vector multiple cloning site, and cloned onto the 3' end of the second linker sequence. A third SEG-Linker sequence can optionally be cloned onto the 3' end of the Cc-CipC cohesin sequence. A third cohesin domain polynucleotide sequence encoding Bc-ScaB having the amino acid sequence represented by SEQ ID NO: 15 can be PCR amplified from *Bacteroides cellulosolvens* using primers engineered with appropriate restriction sites for use with the pET6xHN-N vector multiple cloning site, and optionally cloned onto the 3' end of the third linker sequence.

The resulting expression vector would comprise the following (5' to 3'): CBD sequence; a first linker sequence; a first cohesin; a second linker sequence; a second cohesin; a third linker sequence, and a third cohesin. The restriction sites on the 5' and 3' ends of each cohesin sequence can be unique, simplifying subsequent cloning of replacement cohesins.

Fusion polypeptides that comprise an enzyme and a dockerin may be generated, where each of the three enzymes is linked to a unique dockerin domain that will selectively bind to one of the cohesin domains of the recombinant scaffold polypeptide.

The glycerol dehydrogenase dhaB-dockerin recombinant target protein can be made by cloning the dhaB and dockerin domain polynucleotide sequences into a bacterial expression vector. The dhaB polynucleotide sequence can be cloned into the same translational frame as the dockerin domain polynucleotide sequence, creating a continuous dhaB-dockerin recombinant polynucleotide construct that can be translated into a dhaB-dockerin recombinant target polypeptide. The dockerin domain polynucleotide sequence can be cloned onto the 3' end of the dhaB polynucleotide sequence in the pET6xHN-N expression vector. dhaB can be tagged with, for example, a His tag, if desired. The tag can be removed following protein purification. The vector can comprise a T7 promoter with the lac operator, allowing for IPTG-inducible expression.

The dhaB polynucleotide sequence encodes a polypeptide having an amino acid sequence represented by SEQ ID NO: 8. The dockerin domain polynucleotide sequence can be obtained from *C. thermocellum* (ATCC 27405). The Ct-CipA dockerin domain sequence can be PCR amplified from the bacterial genomic DNA using primers engineered with appropriate restriction sites. The resulting PCR product can then be cloned into the pET6xHN-N vector containing the dhaB polynucleotide sequence. The dockerin domain polynucleotide sequence can be inserted at the 3' end of the dhaB sequence with a continuous reading frame useful for expression of the dhaB-dockerin recombinant target polypeptide.

The aldehyde dehydrogenase ald4-dockerin recombinant target polypeptide can be made by cloning the ald4 and dockerin domain polynucleotide sequences into a bacterial expression vector. The ald4 polynucleotide sequence can be cloned into the same translational frame as the dockerin domain polynucleotide sequence, creating a continuous ald4-dockerin recombinant polynucleotide construct that can be translated into an ald4-dockerin recombinant target polypeptide. The dockerin domain polynucleotide sequence can be cloned onto the 3' end of the dhaB polynucleotide sequence in the pET6xHN-N expression vector. ald4 can be tagged with, for example, a His tag, if desired. The tag can be removed following protein purification. The vector can comprise a T7 promoter with the lac operator, allowing for IPTG-inducible expression.

The ald4 polynucleotide sequence encodes a polypeptide having an amino acid sequence represented by SEQ ID NO: 9. The dockerin domain polynucleotide sequence can be obtained from *C. cellulolyticum* (ATCC 35319). The Cc-EndA dockerin domain sequence can be PCR amplified from the bacterial genomic DNA using primers engineered with appropriate restriction sites. The resulting PCR product can then be cloned into the pET6xHN-N vector containing the ald4 polynucleotide sequence. The dockerin domain polynucleotide sequence can be inserted at the 3' end of the ald4 sequence with a continuous reading frame useful for expression of the ald4-dockerin recombinant target polypeptide.

If it is to be included in the enzymatic polypeptide scaffold, the NADH oxidase Nox-dockerin recombinant target polypeptide can be made by cloning the Nox and dockerin domain polynucleotide sequences into a bacterial expression vector. The Nox polynucleotide sequence can be cloned into the same translational frame as the dockerin domain polynucleotide sequence, creating a continuous Nox-dockerin recombinant polynucleotide construct that can be translated into a Nox-dockerin recombinant target polypeptide. The dockerin domain polynucleotide sequence can be cloned onto the 3' end of the Nox polynucleotide sequence in the pET6xHN-N expression vector. Nox can be tagged with, for example, a His tag, if desired. The tag can be removed following protein purification. The vector can comprise a T7 promoter with the lac operator, allowing for IPTG-inducible expression.

The Nox polynucleotide sequence encodes a polypeptide having an amino acid sequence represented by SEQ ID NO: 10. The dockerin domain polynucleotide sequence can be obtained from *B. cellulosolvens*. The Bc-ScaB dockerin domain sequence can be PCR amplified from the bacterial genomic DNA using primers engineered with appropriate restriction sites. The resulting PCR product can then be cloned into the pET6xHN-N vector containing the Nox polynucleotide sequence. The dockerin domain polynucleotide sequence can be inserted at the 3' end of the Nox sequence with a continuous reading frame useful for expression of the ald4-dockerin recombinant target polypeptide.

Each of the expression vectors described can be transformed into *E. coli*. Resulting colonies can be picked for overnight incubation in LB/amp cultures at 37° C. until an O.D. of 0.6-0.8 is reached. IPTG can be added to a concentration of 1 mM. The cultures can then be further incubated for an additional 4-5 hours. The induced bacterial cultures can then be centrifuged to form a large bacterial pellet. The supernatant can be decanted and the pellet of induced bacteria can be frozen for later use Affinity purification can be used to purify the induced recombinant polypeptide under native conditions.

The enzymatic polypeptide scaffold carrying the enzymes of the 3-HP metabolic pathway can assembled by sequentially adding the recombinant target polypeptides to the recombinant polypeptide scaffold.

In certain embodiments, the assembled enzymatic polypeptide scaffold carrying the enzymes of the 3-HP can comprise only the glycerol dehydrogenase and the aldehyde dehydrogenase. When only these two enzymes are included in the scaffold, an alternative source of NAD+ must be provided.

In certain embodiments, the assembled enzymatic polypeptide scaffold carrying the enzymes of the 3-HP metabolic pathway can be used in a bioreactor to produce 3-HP from glycerol. In some embodiments, crude glycerol is added to a bioreactor having the enzymatic polypeptide scaffold tethered to the bioreactor via a surface anchoring domain. In other embodiments, free enzymatic polypeptide scaffolds can be added to a bioreactor containing crude glycerol. Following a sufficient time in the bioreactor, 3-HP can be collected from the bioreactor.

In yet other embodiments, assembled enzymatic polypeptide scaffold carrying the enzymes of the 3-HP metabolic pathway can be included in or added to a biodiesel bioreactor. In such embodiments, glycerol can be can be converted to 3-HP.

Figure 18:
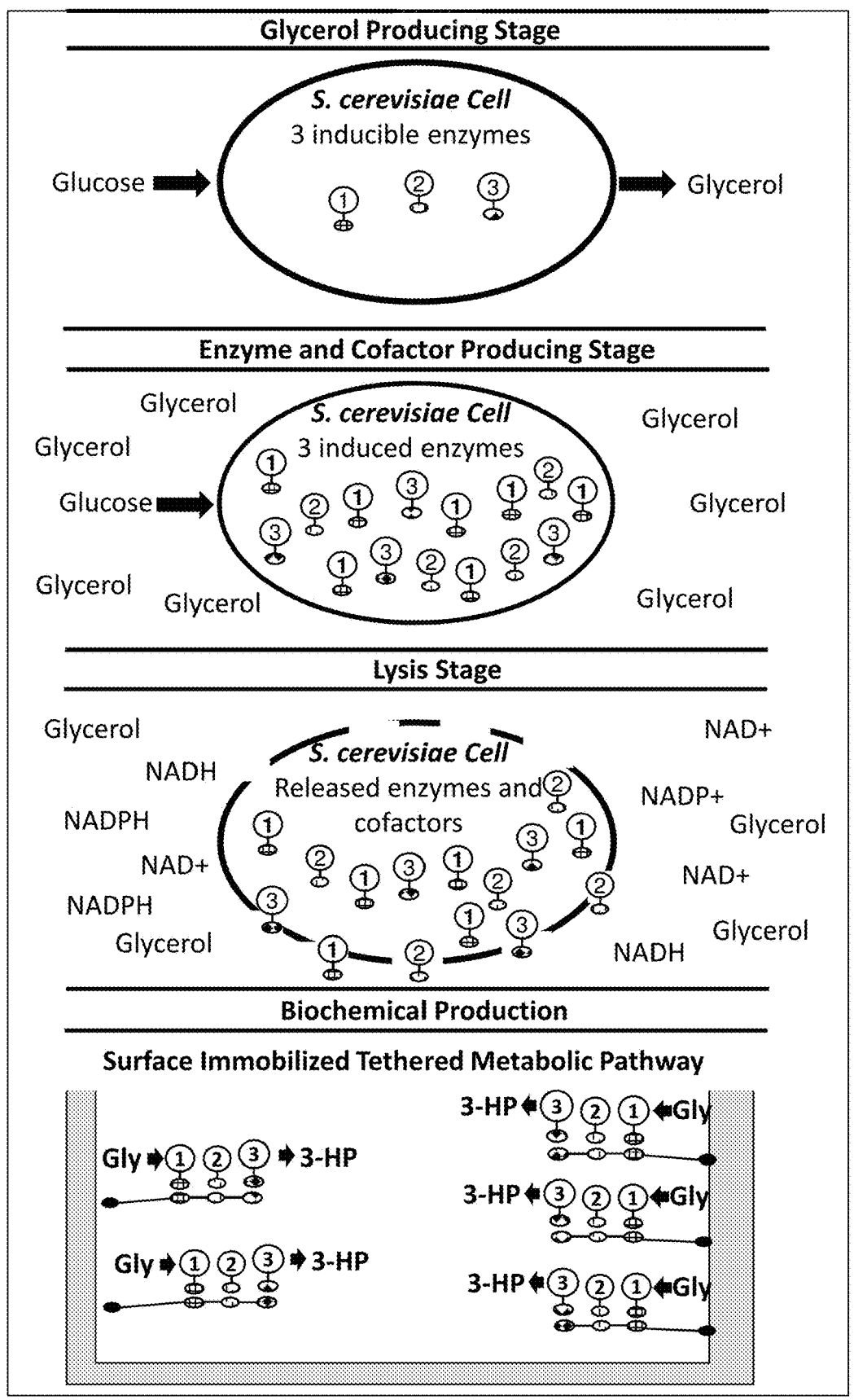
FIG. 18 is an illustration of a modified system where cells produce and release the recombinant target polypeptides to fill the spots on a recombinant polypeptide scaffold according to one embodiment.

In yet another embodiment, the recombinant target polypeptides carrying the dhaB, ald4, and NADH oxidase enzymes can be expressed by cells within a bioreactor, as depicted in FIG. 18. The same cells that express the three recombinant target polypeptides can also be responsible for converting glucose to glycerol, thus providing the starting material for the 3-HP pathway. In such embodiments, the bioreactor can also comprise recombinant polypeptide scaffolds having no bound recombinant target polypeptides. Upon lysis of the cells, the recombinant target polypeptides can selectively bind to the cohesin domains of the recombinant polypeptide scaffolds, thus forming the complete enzymatic polypeptide scaffold. The complete scaffold can then convert the glycerol to 3-HP. In those embodiments where glycerol is produced from glucose in the same bioreactor as 3-HP production, glucose production can also occur in the bioreactor. This can result in a single bioreactor being able to convert cellulosic biomass into 3-HP.

Example 3—Enzymatic Polypeptide Scaffold for 1,3 PDO Production

An enzymatic polypeptide scaffold capable of generating 1,3-propanediol (1,3 PDO) from glycerol can be generated according to embodiments described herein. 1,3 PDO is a three carbon diol that is mainly used as a building block in the production of polymers such as polytrimethylene terephthalate, and can be formulated into industrial products such as composites, adhesives, laminates, coatings, moldings, aliphatic polyesters, and copolyesters, it can also be used as a solvent and in antifreeze. Similarly to 3-HP, 1,3 propanediol can be synthesized from intermediates such as glycerol. The metabolic pathways for synthesis of 1,3 propanediol and 3-HP both utilize glycerol dehydrogenase. Whereas the synthesis of 3-HP requires an aldehyde dehydrogenase to convert 3-hydroxypropioaldehyde to 3-HP, 1,3 propanediol dehydrogenases convert 3-hydroxypropioaldehyde to 1,3 propanediol.

Figure 19A:
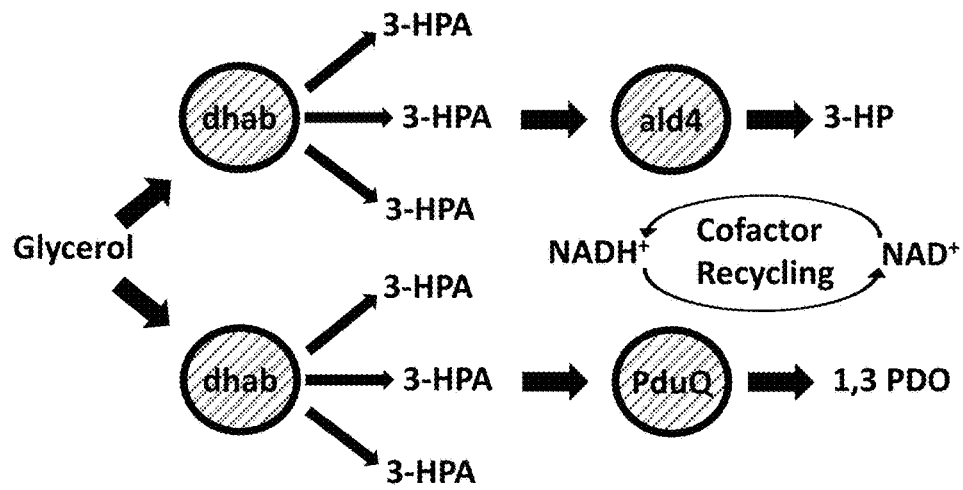
FIG. 19A is an illustration of two free-enzyme metabolic pathways for the synthesis of 3-hydroxypropionic acid and 1,3 propanediol according to one embodiment.

In some embodiments, a two-enzyme enzymatic polypeptide scaffold can be generated for the synthesis of 1,3 propanediol from glycerol. Such a scaffold can be generated in a similar manner to that described in Example 2 for the 3-HP enzymatic polypeptide scaffold. The 3-HP enzymatic polypeptide scaffold can be modified to replace the aldehyde dehydrogenase with a 1,3 propanediol dehydrogenase (see, e.g., FIG. 19A).

Figure 19B:
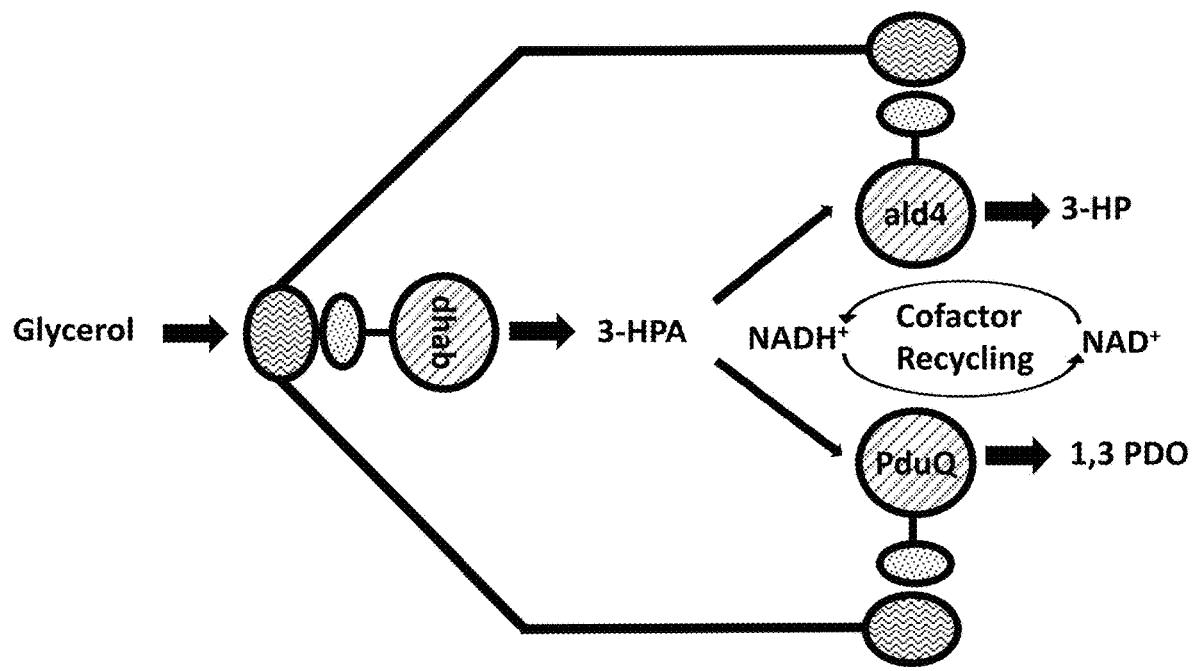
FIG. 19B is an illustration of two metabolic pathways occurring on a single enzymatic polypeptide scaffold according to one embodiment.

In other embodiments, a hybrid enzymatic polypeptide scaffold can be generated to provide for synthesis of both 3-HP and 1,3 propanediol. As depicted in FIG. 19B, an enzymatic polypeptide scaffold can be designed to share a glycerol dehydrogenase. An advantage to such a configuration is that the 1,3 propanediol can, such as with PduQ, act as an NADH oxidase.

Example 4—Enzymatic Polypeptide Scaffold for 2,3 Butanediol Production and Methods of Use An enzymatic polypeptide scaffold capable of generating 2,3 butanediol from glycerol can be generated according to embodiments described herein. 2,3 butanediol is a bulk chemical building block that can also be fideoxydehydrated to butenes and further oligomerized in high yields to produce gasoline, diesel, and jet fuels. Certain native microorganisms are able to produce 2,3 butanediol via fermentation of sugars such as glucose. Additional microorganisms can be engineered to produce 2,3 butanediol by the expression of heterologous genes encoding enzymes in the synthetic pathway.

*Zymomonas mobilis* represents an attractive target for such metabolic engineering due to its high specific glucose uptake rate, rapid catabolism and the ability of engineered strains to metabolize the major biomass sugars including D-xylose and L-arabinose. Microbial production of 2,3 butanediol, however, suffers from low yields because of factors such as enzyme instability, lack of direct channeling of intermediates between enzymes, and inhibition of the synthesis pathway by end products and intermediates. An enzymatic polypeptide scaffold as described herein can overcome these limitations for both in vitro and in vivo production (by, for example, introducing the enzymatic polypeptide scaffold into an organism of interest).

Figure 20A:
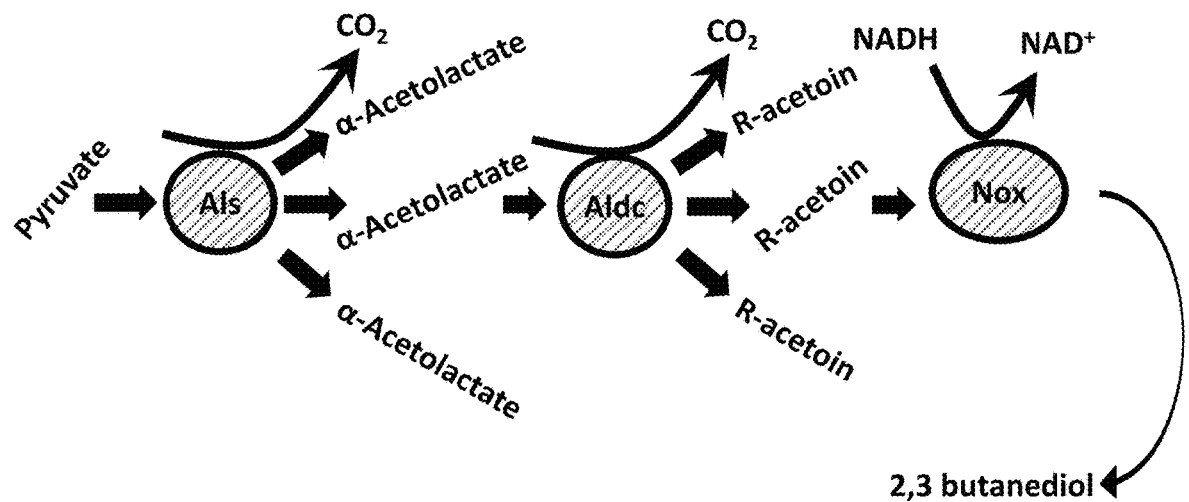
FIG. 20A is an illustration of a free-enzyme metabolic pathway for the synthesis of 2,3 butanediol from pyruvate according to one embodiment.
Figure 20B:
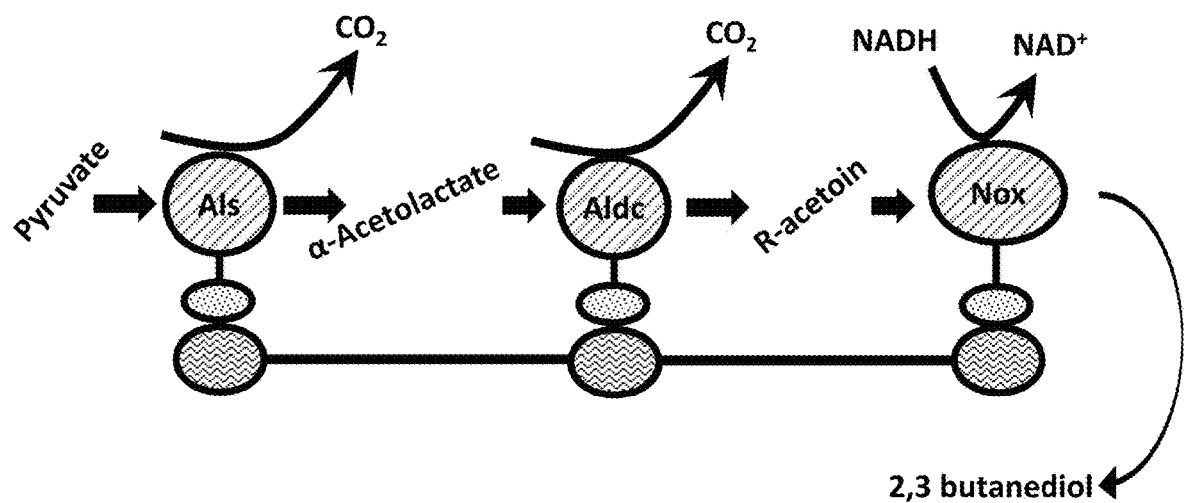
FIG. 20B is an illustration of an enzymatic polypeptide scaffold carrying a 2,3 butanediol synthesis pathway.

FIG. 20 illustrates one route to 2,3 butanediol involving a three-step conversion of pyruvate. Pyruvate is first converted to α-acetolactate by acetolactate synthase (Als). Acetolactate decarboxylase (Aldc) then converts α-acetolactate to acetoin, which is subsequently converted to 2,3 butanediol by butanediol dehydrogenase (Bdh). An enzymatic polypeptide scaffold comprising these three enzymes can be generated in the same manner as that described in Example 2 for the 3-HP pathway. To generate the 2,3-butanediol enzymatic polypeptide pathway, the polynucleotide sequences encoding the dhaB, ald4, and Nox enzymes in the recombinant target polypeptide expression vectors can simply be replaced by polynucleotide sequences encoding Als (SEQ ID NO: 21), Aldc (SEQ ID NO: 22), and Bdh (SEQ ID NO: 23).

Figure 8:
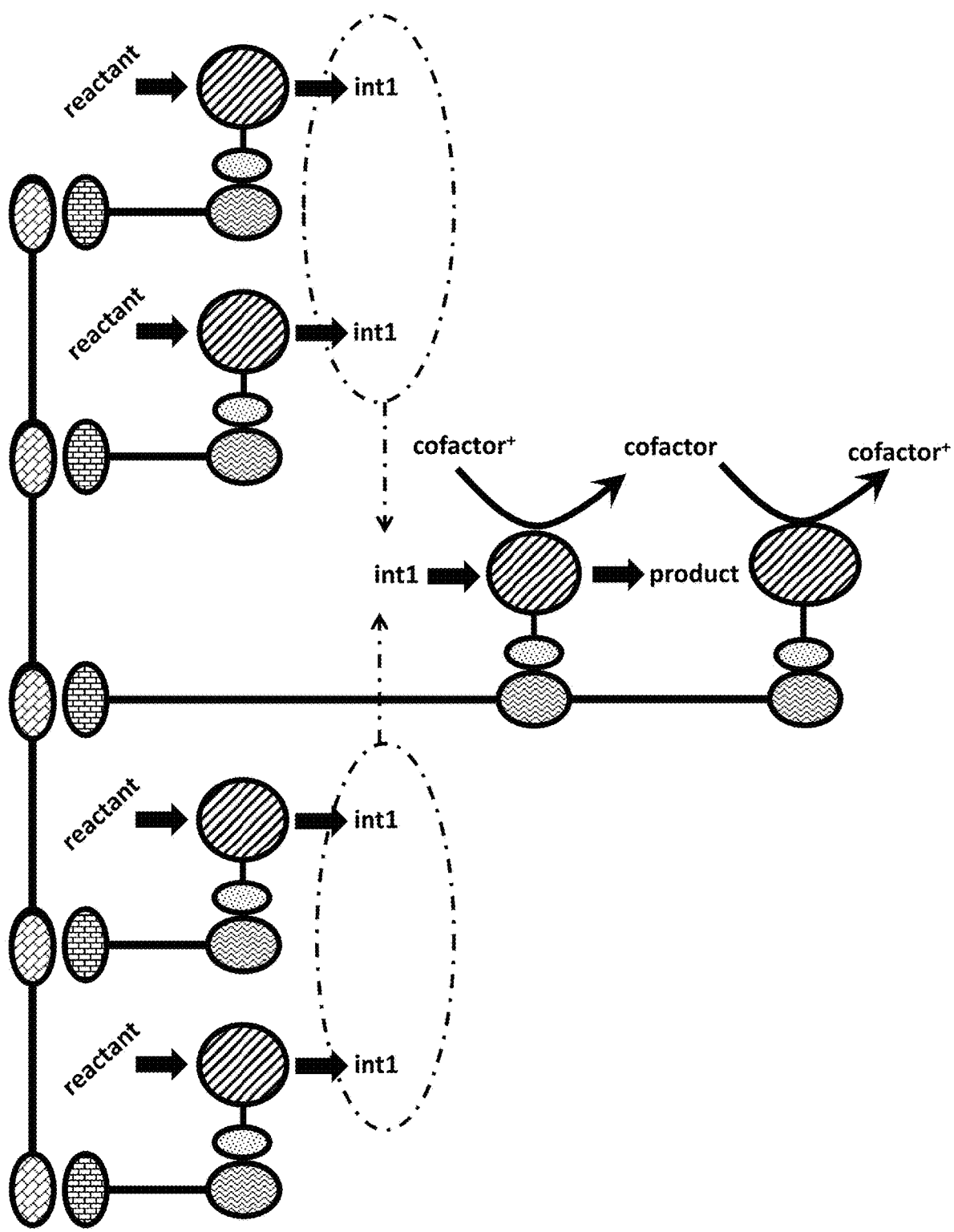
FIG. 8 is an illustration depicting a grouping of enzymatic polypeptide scaffolds modified to reduce the effects of the rate-limiting first enzyme according to one embodiment.

In certain embodiments, the assembled enzymatic polypeptide scaffold carrying the enzymes of the 2,3 butanediol metabolic pathway can be used in a bioreactor to produce 2,3 butane diol from pyruvate. In some embodiments, pyruvate is added to the bioreactor as a starting material. In other embodiments, pyruvate can be synthesized from, for example, cellulosic biomass, as depicted in FIG. 8. As illustrated in FIG. 8, enzymatic polypeptide scaffolds of several metabolic pathways can be grouped together via an adapter scaffold. The adapter scaffold can keep related metabolic processes spatially grouped to enhance intermediate shuttling and overall kinetics as a result of localized intermediate concentration. As depicted in FIG. 8, this group of enzymatic polypeptide scaffolds can even be anchored to the cellulosic biomass starting material.

Example 5—Enzymatic Polypeptide Scaffold for Alkene Synthesis

Figure 21:
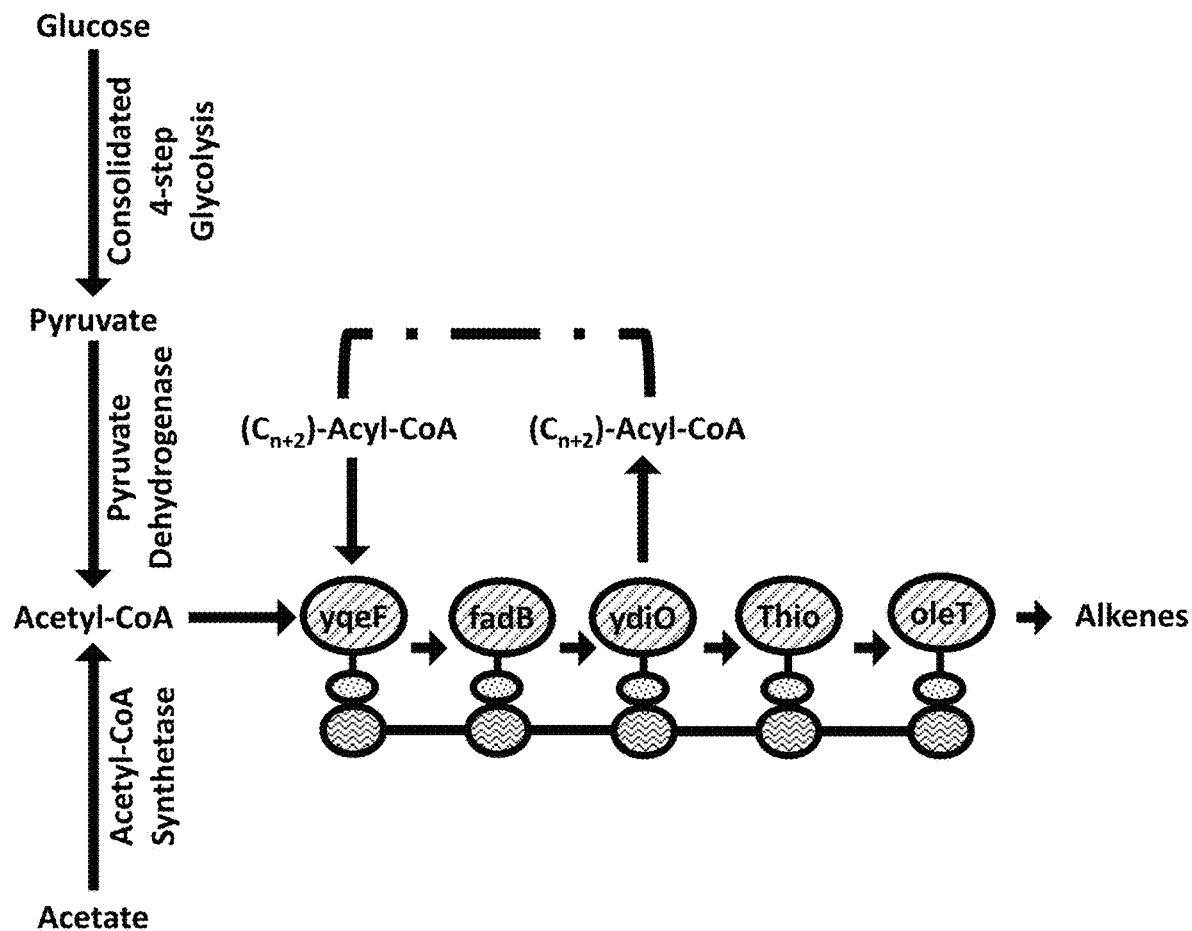
FIG. 21 is an illustration of an enzymatic polypeptide scaffold carrying an alkene synthesis pathway according to one embodiment.

An enzymatic polypeptide scaffold capable of acyl-CoA elongation and alkene production can be generated according to embodiments described herein. Acyl-CoA is a group of coenzyme intermediates in the production and metabolism of fatty acids and alkenes. The cyclical reaction scheme for Acyl-CoA elongation is depicted in FIG. 21. The sequential action of three enzymes extends the carbon chain length of Acyl-CoA (or Acetyl-CoA). An Acyl-CoA acetyltransferase (e.g., YqeF; also known as a thiolase), an enoyl-CoA hydratase/3-hydroxyacyl-CoA dehydrogenase (e.g., FadB) and an enoyl-CoA reductase (e.g., YdiO) work cooperatively to achieve the elongation.

This three-enzyme elongation pathway can be coupled to one or two additional enzymes for the production of fatty acids and alkenes. A thioesterase (thio) acts to stop the elongation cycle at the desired chain length and generate fatty acids, which in turn are converted to alkenes of desired chain length via oxidative decarboxylation catalyzed by cytochrome P450 enzymes (e.g., OleT).

An enzymatic polypeptide scaffold comprising these three enzymes can be generated in a similar manner as that described in Example 2 for the 3-HP pathway. However, the four- or five-enzyme alkene pathway will require one or two additional cohesin domains and linker domains to be added to the recombinant polypeptide scaffold and one or two additional recombinant target polypeptides. Additional cohesin/dockerin pairs can be chosen from Table 4. The additional cohesin/linker segments of the recombinant polypeptide scaffold and the recombinant target polypeptides can be generated following the general methods presented in Example 2, whereas the polynucleotides encoding the thio and OleT enzymes can have a polynucleotide sequence that encode a polypeptide represented by SEQ ID NO: 27 and SEQ ID NO: 28, respectively. For the three recombinant target polypeptides from Example 2, the polynucleotide sequences encoding the dhaB, ald4, and Nox enzymes in the recombinant target polypeptide expression vectors can simply be replaced by polynucleotide sequences encoding YqeF (SEQ ID NO: 24), FadB (SEQ ID NO: 25), and YdiO (SEQ ID NO: 26). In certain embodiments, the assembled enzymatic polypeptide scaffold carrying the enzymes of the alkene synthesis pathway can be used in a bioreactor to produce various alkenes.

Figure 22:
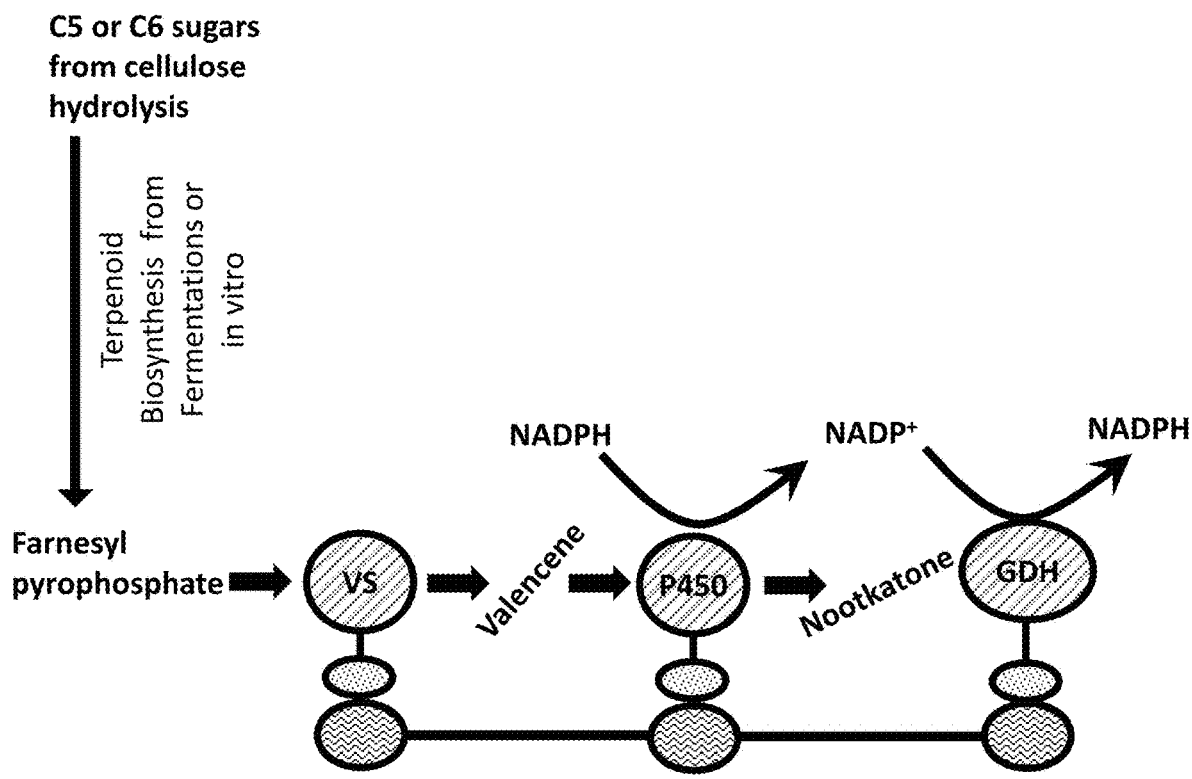
FIG. 22 is an illustration of an enzymatic polypeptide scaffold carrying a nootkatone synthesis pathway according to one embodiment.
Figure 23:
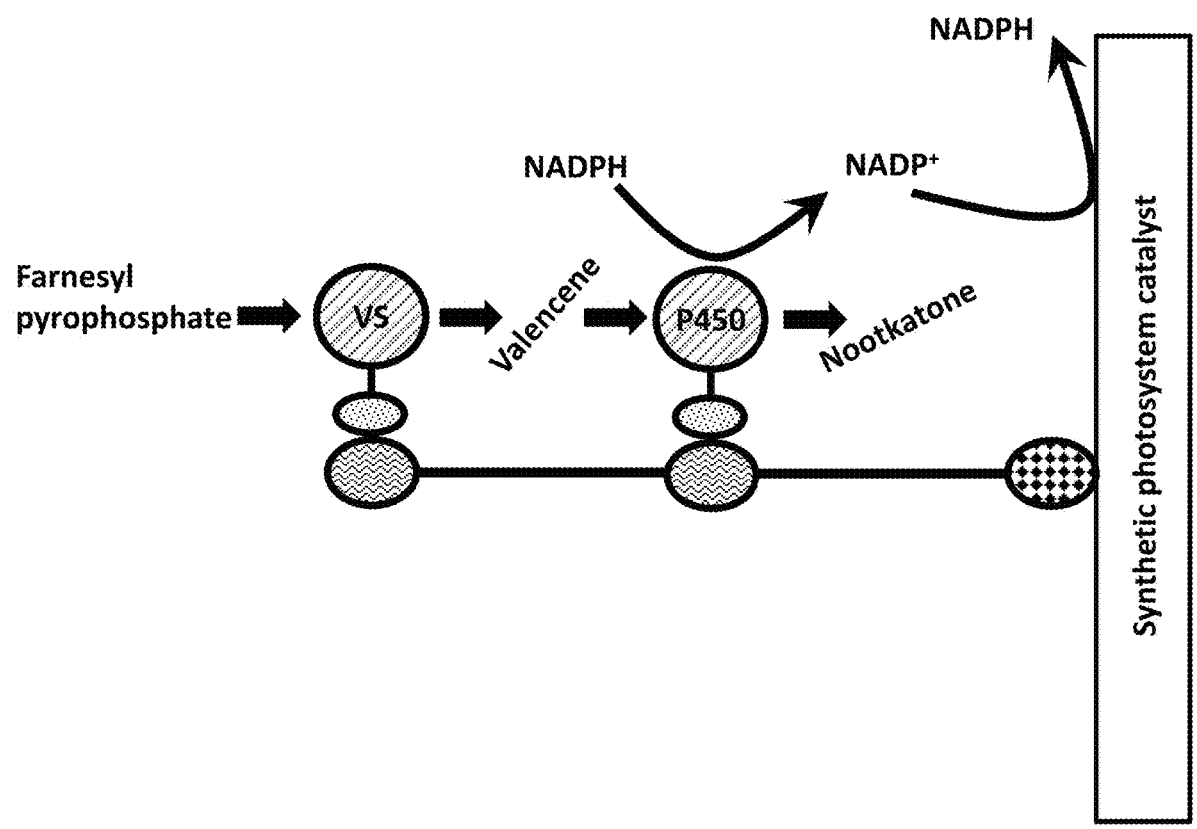
FIG. 23 is an illustration of an anchored enzymatic polypeptide scaffold carrying a nootkatone synthesis pathway according to one embodiment.

Example 6—Enzymatic Polypeptide Scaffold for 2,3 Butanediol Production and Methods of Use An enzymatic polypeptide scaffold capable of generating nootkatone from farnesyl pyrophosphate can be generated according to embodiments described herein. Nootkatone is a naturally occurring aromatic compound found in grapefruit that has applications as a flavoring and a fragrance, and also exhibits activity as an insect and tick repellent. As depicted in FIG. 22, nootkatone can be synthesized from farnesyl pyrophosphate by the sequential action of valencene synthase (e.g., vs from *Vitis vinifera*) to generate valencene, followed by the conversion of valencene to nootkatone by cytochrome P450 (P450; suitable examples include P450cam from *Pseudomonas putida* and P450BM-3 from *Bacillus megaterium* and variants thereof). Glucose dehydrogenase (GDH) can be included to participate in cofactor recycling. Farnesyl pyrophosphate may be supplied directly or may be produced by terpenoid biosynthesis from C5 or C6 sugars that may in turn be generated by the hydrolysis of cellulose.

An enzymatic polypeptide scaffold comprising these three enzymes can be generated in the same manner as that described in Example 2 for the 3-HP pathway. To generate the nootkatone enzymatic polypeptide pathway, the polynucleotide sequences encoding the dhaB, ald4, and Nox enzymes in the recombinant target polypeptide expression vectors can simply be replaced by polynucleotide sequences encoding vs (SEQ ID NO: 30), P450 (SEQ ID NO: 31 or SEQ ID NO: 32), and GDH (SEQ ID NO: 33), if present. In certain embodiments, the assembled enzymatic polypeptide scaffold carrying the enzymes of the alkene synthesis pathway can be used in a bioreactor to produce nootkatone. The farnesyl pyrophosphate, which may be from a previous fermentation process, and initial NADPH cofactor (being recycled by additional enzymatic steps on other enzymatic scaffolds or by immobilized synthetic or enzymatic electron donors on a conductive surface, see, FIG. 22) are added to the bioreactor to interact with the enzymatic polypeptide scaffold. Nootkatone is then recovered.

Example 7—Identification of Protein Binding Partners from a Whole Cell Lysate According to some embodiments, assemblies of enzymatic polypeptide scaffolds can be used to identify novel interacting partners with a protein complex. For example, any of the enzymatic polypeptide scaffolds described above can be used as bait to identify novel members of a complex. The number of different members on the bait complex equals the number of positions (slots) on the linker protein scaffold.

The customized enzymatic polypeptide scaffold can be assembled by sequentially adding recombinant polypeptide scaffolds to cellulose-coated glass beads having a diameter of approximately 400-700 um. The amount of glass beads used can be enough to adhere approximately 1000 μg of protein comprising the synthetic proteome. The recombinant polypeptide scaffold comprising the surface anchor domain, cohesin domains and linker domains (SAD-linker-cohesin protein) can be deposited on the cellulose-coated glass beads, allowed to adhere, and then washed. Selected dockerin fusion constructs (such as dhaB-dockerin, ald4-dockerin, and Nox-dockerin) can then be deposited on the glass beads. After allowing the dockerins and concomitant cohesins time to interact, the beads can then be washed.

Whole cell lysates can be prepared under non-denaturing conditions using standard methods. After being cleared of debris, the whole cell lysate can be applied to the previously assembled enzymatic polypeptide scaffold on the glass beads. The whole cell lysate and synthetic proteome beads can be mixed to allow protein complex formation between the scaffold and proteins present in the whole cell lysate. The beads can subsequently be washed and then boiled in SDS sample buffer.

Part of the resulting SDS sample buffer can be resolved by two dimensional gel electrophoresis followed by Cypro Ruby staining. The resulting bands that do not correspond to any of the dockerin fusion proteins or scaffold proteins can be excised from the gel and identified using mass spectrometry and/or microsequencing. The putative binding proteins identified by mass spectrometry and microsequencing can be confirmed by performing western blots of the remaining SDS sample buffer.

What is claimed is:

1. An enzymatic polypeptide scaffold comprising:
   a first linker domain, a first cohesin domain, and a second cohesin domain, wherein the first linker domain interconnects the first and second cohesin domains;
   a first recombinant polypeptide comprising a first dockerin domain and an acetolactate synthase catalytic domain, wherein the first dockerin domain selectively binds to the first cohesin domain and the acetolactate synthase catalytic domain has a sequence identity of at least 90% to the polypeptide of SEQ ID NO: 21; and
   a second recombinant polypeptide comprising a second dockerin domain and an acetolactate decarboxylase domain, wherein the second dockerin domain selectively binds to the second cohesin domain, and the acetolactate decarboxylase catalytic domain has a sequence identity of at least 90% to the polypeptide of SEQ ID NO: 22.

2. The enzymatic polypeptide scaffold of claim 1, further comprising:
   a second linker domain and a third cohesin domain, wherein the second linker domain interconnects the second and third cohesin domains; and
   a third recombinant polypeptide comprising a third dockerin domain and a butanediol dehydrogenase catalytic domain, wherein the third dockerin domain selectively binds to the third cohesin domain and the butanediol dehydrogenase catalytic domain has a sequence identity of at least 90% to the polypeptide of SEQ ID NO: 23.

3. The enzymatic polypeptide scaffold of claim 1, further comprising a surface anchoring domain and an anchoring linker domain, wherein the anchoring linker domain interconnects the surface anchoring domain and the first cohesin domain.

4. The enzymatic polypeptide scaffold of claim 2, further comprising:
   a first polypeptide linker between the first dockerin domain and the acetolactate synthase catalytic domain, wherein the acetolactate synthase catalytic domain has a sequence identity of at least 90% to the polypeptide of SEQ ID NO: 21,
   a second polypeptide linker between the second dockerin domain and the acetolactate decarboxylase catalytic domain, wherein the acetolactate decarboxylase catalytic domain has a sequence identity of at least 90% to the polypeptide of SEQ ID NO: 22, and
   a third polypeptide linker between the third dockerin domain and the butanediol dehydrogenase catalytic domain, wherein the butanediol dehydrogenase catalytic domain has a sequence identity of at least 90% to the polypeptide of SEQ ID NO: 23.

5. The enzymatic polypeptide scaffold of claim 3, wherein the surface anchoring domain is a cellulose binding domain.

6. The enzymatic polypeptide scaffold of claim 2, wherein the first linker and the second linker are each independently a synthetic linker, the first linker has an amino acid sequence that is 95% identical to SEQ ID NO: 4, and the second linker has an amino acid sequence that is 95% identical to SEQ ID NO: 6.

7. An enzymatic polypeptide scaffold array comprising:
a first enzymatic polypeptide scaffold according to claim 1, further comprising a first adapter linker and a first adapter dockerin, wherein the first adapter linker interconnects the first adapter dockerin and the first cohesin domain of the first scaffold;
a second enzymatic polypeptide scaffold according to claim 1, further comprising a second adapter linker and a second adapter dockerin, wherein the second adapter linker interconnects the second adapter dockerin and the first cohesin domain of the second scaffold; and
an adapter scaffold comprising two adapter cohesin domains and an adapter linker domain that interconnects the adapter cohesins,
wherein the first and second adapter dockerins selectively bind to the adapter cohesin domains; and
wherein the adapter scaffold interconnects the first and second enzymatic polypeptide scaffolds.

8. A method for producing 2,3 butanediol from pyruvate, comprising:
(i) contacting pyruvate with the enzymatic polypeptide scaffold of claim 1, and
(ii) recovering 2,3 butanediol.

\* \* \* \* \*

UNITED STATES PATENT AND TRADEMARK OFFICE
CERTIFICATE OF CORRECTION

PATENT NO. : 10,577,633 B2
APPLICATION NO. : 15/467340
DATED : March 3, 2020
INVENTOR(S) : Yannick J. Bomble et al.

Page 1 of 1

It is certified that error appears in the above-identified patent and that said Letters Patent is hereby corrected as shown below:

In the Specification

Column 1, Line 7 should read:
CROSS-REFERENCE TO RELATED APPLICATIONS
This application claims priority to United States Provisional Application No. 62/312,158, filed on March 23, 2016, the entire disclosure of which is expressly incorporated herein by reference for all purposes.

Signed and Sealed this
Twenty-sixth Day of May, 2020

Andrei Iancu
*Director of the United States Patent and Trademark Office*